United States Patent
Otake et al.

(10) Patent No.: US 7,589,096 B2
(45) Date of Patent: Sep. 15, 2009

(54) AZOLE DERIVATIVES

(75) Inventors: Norikazu Otake, Tsukuba (JP); Yuji Haga, Tsukuba (JP); Makoto Jitsuoka, Tsukuba (JP); Akio Kanatani, Tsukuba (JP)

(73) Assignee: Banyu Pharmaceutical Co., Ltd., Tokyo (JP)

( * ) Notice: Subject to any disclaimer, the term of this patent is extended or adjusted under 35 U.S.C. 154(b) by 34 days.

(21) Appl. No.: 12/071,808

(22) Filed: Feb. 26, 2008

(65) Prior Publication Data

US 2008/0188507 A1 Aug. 7, 2008

Related U.S. Application Data

(62) Division of application No. 10/536,360, filed as application No. PCT/JP03/15018 on Nov. 25, 2003, now Pat. No. 7,365,079.

(30) Foreign Application Priority Data

Nov. 29, 2002 (JP) .............................. 2002-346997

(51) Int. Cl.
| | |
|---|---|
| A61K 31/438 | (2006.01) |
| A61K 31/506 | (2006.01) |
| A61K 31/4545 | (2006.01) |
| C07D 233/96 | (2006.01) |
| C07D 401/14 | (2006.01) |
| C07D 401/02 | (2006.01) |

(52) U.S. Cl. .................. 514/256; 514/278; 544/230; 546/17

(58) Field of Classification Search ............ 514/256, 514/278; 544/230; 546/17
See application file for complete search history.

(56) References Cited

U.S. PATENT DOCUMENTS 7,105,526 B2 * 9/2006 Otake et al. ............ 514/263.22

FOREIGN PATENT DOCUMENTS

| WO | 00/27845 | 5/2000 |
|---|---|---|
| WO | 01-14376 | 3/2001 |
| WO | 02-48152 | 6/2002 |
| WO | 2004/002986 | 1/2004 |

OTHER PUBLICATIONS

Turnbull et al., Diabetes, 51, pp. 2441-2449, Aug. 2002.
Promising antiobesity drug fails to produce clinically meaningful weight loss, retrieved from Internet on Feb. 22, 2007, <http://www. http://www.physorg.com/printnews.php?newsid=79101505>.
International Search Report issued Apr. 20, 2004 in the International (PCT) Application of which the present application is a divisional of the U.S National Stage.

* cited by examiner

*Primary Examiner*—Rebecca L Anderson
*Assistant Examiner*—Jason Nolan
(74) *Attorney, Agent, or Firm*—Wenderoth, Lind & Ponack, L.L.P.

(57) ABSTRACT

The present invention relates to a compound of the formula (I):

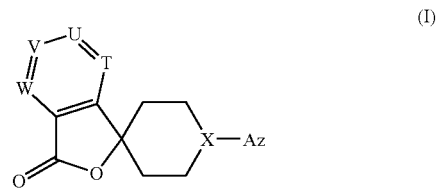

wherein Az is a group comprising a monocyclic azole or a bicyclic aromatic ring of the same or different fused azoles; T, U, V and W are independently methine or nitrogen, wherein a methine may be optionally substituted by a substituent, and at least two of T, U, V and W are methine groups; and X is nitrogen or methine.

The compounds of the present invention are useful as agents for the treatment of various kinds of diseases related to NPY, for example, cardiovascular disorders, nervous system disorders, genitative diseases, metabolic diseases, genital or reproductive disorders, gastro-intestinal disorders, respiratory disorders, inflammatory diseases or glaucoma, and the like.

23 Claims, No Drawings

AZOLE DERIVATIVES

CROSS REFERENCES TO RELATED APPLICATIONS

This application is a divisional of application Ser. No. 10/536,360, now U.S. Pat. No. 7,365,079, which was a U.S. national stage of International Application No. PCT/JP2003/015018, filed Nov. 25, 2003.

TECHNICAL FIELD

The present invention is useful in medical fields. In more detail, novel azole derivatives of the present invention have an effect as neuropeptide Y receptor antagonists and are useful as agents for the treatment of various kinds of cardiovascular disorders, nervous system disorders, metabolic diseases, genital or reproductive disorders, gastro-intestinal disorders, respiratory disorders, inflammatory diseases or glaucoma, and the like.

BACKGROUND ART

Neuropeptide Y (hereinafter referred to as NPY), a peptide consisting of 36 amino acids, was first isolated from porcine brain by Tatemoto et al in 1982 (NATURE, vol. 296, p. 659 (1982)). NPY is widely distributed in central nervous system and peripheral nervous system, and plays various roles as one of the most abundant peptides in the nervous system. That is, NPY acts as an orexigenic substance in the central nervous system and markedly promotes fat accumulation via the mediation of secretion of various hormones or the action of the nervous system. It is known that, continuous intracerebroventricular administration of NPY induces obesity and insulin resistance due to these actions (INTERNATIONAL JOURNAL OF OBESITY, vol. 19, p. 517 (1995); Endocrinology, vol. 133, p. 1753 (1993)). It is also known that NPY has central actions such as depression, anxiety, schizophrenia, pain, dementia, circadian rhythm control and the like (DRUGS, vol. 52, p. 371 (1996); THE JOURNAL OF NEUROSCIENCE, vol. 18, p. 3014 (1998)). Furthermore, in the periphery, NPY coexists with norepinephrine in sympathetic-nerve terminals and is related to the tonicity of the sympathetic nervous system. It is known that peripheral administration of NPY causes vasoconstriction and enhances the activities of other vasoconstrictive substances such as norepinephrine (BRITISH JOURNAL OF PHARMACOLOGY, vol. 95, p. 419 (1988)). It is also reported that NPY could participate in the development of cardiac hypertrophy as a result of the sympathetic stimulation (PROCEEDINGS OF THE NATIONAL ACADEMY OF SCIENCES OF THE UNITED STATES OF AMERICA, vol. 97, p. 1595 (2000)).

On the other hand, it is reported that NPY is also involved in the secretory function of sexual hormones and growth hormone, sexual behavior and reproductive function, gastro-intestinal motility, bronchoconstriction, inflammation and alcohol preference (LIFE SCIENCE, vol. 55, p. 551 (1994); THE JOURNAL OF ALLERGY AND CLINICAL IMMUNOLOGY, vol. 101, p. S345 (1998); NATURE, vol. 396, p. 366 (1998)).

NPY has, a variety of pharmacological effects resulting from NPY binding to some NPY receptors to which peptide YY and pancreatic polypeptide, which are the analogs of NPY, also bind. It is known that these pharmacological effects of NPY are mediated by the action of at least five receptors with or without synergistic interactions (TRENDS IN NEUROSCIENCES, vol. 20, p. 294 (1997)).

It is reported that the central effects mediated by NPY 1 receptor include remarkable orexigenic effect (ENDOCRINOLOGY, vol. 137, p. 3177 (1996); ENDOCRINOLOGY, vol. 141, p. 1011 (2000)). Further, NPY Y1 receptor is reported to be involved in anxiety and pain (NATURE, vol. 259, p. 528 (1993); BRAIN RESEARCH, vol. 859, p. 361 (2000). In addition, the pressor effect mediated by the strong vasoconstrictor action in the periphery is also reported (FEBS LETTERS, vol. 362, p. 192 (1995); NATURE MEDICINE, vol. 4, p. 722 (1998)).

It is known that the effects mediated by NPY Y2 receptor include an inhibitory effect on the release of various neurotransmitters in the sympathetic nerve endings (BRITISH JOURNAL OF PHARMACOLOGY, vol. 102, p. 41 (1991); SYNAPSE, vol. 2, p. 299 (1988)). In periphery, NPY Y2 causes constriction of blood vessel or vas deferens directly or via the control of release of various neurotransmitters (THE JOURNAL OF PHARMACOLOGY AND EXPERIMENTAL THERAPEUTICS, vol. 261, p. 863 (1992); BRITISH JOURNAL OF PHARMACOLOGY, vol. 100, p. 190 (1990)). Inhibition of lipolysis in adipose tissues is also known (ENDOCRINOLOGY, vol. 131, p. 1970 (1992)). Further, inhibition of ion secretion in the gastro-intestinal tract is reported (BRITISH JOURNAL OF PHARMACOLOGY, vol. 101, p. 247 (1990)). On the other hand, the effects on the central nervous system functions such as memory, anxiety and the like are also known (BRAIN RESEARCH, vol. 503, p. 73 (1989); PEPTIDES, vol. 19, p. 359 (1998)).

It is reported that NPY Y3 receptor exists mainly in brain-stem and heart, and is related to the regulation of blood pressure and heart rate (THE JOURNAL OF PHARMACOLOGY AND EXPERIMENTAL THERAPEUTICS, vol. 258, p. 633 (1991); PEPTIDES, vol. 11, p. 545 (1990)). It is also known that NPY Y3 is involved in the control of catecholamine secretion in adrenal gland (THE JOURNAL OF PHARMACOLOGY AND EXPERIMENTAL THERAPEUTICS, vol. 244, p. 468 (1988); LIFE SCIENCE, vol. 50, p. PL7 (1992)).

NPY Y4 receptor has high affinity for pancreatic polypeptide in particular. As for the pharmacological effects of NPY Y4, inhibition of pancreatic exocrine secretion and gastro-intestinal motility is reported (GASTROENTEROLOGY, vol. 85, p. 1411 (1983)). Further, it is reported that NPY enhances the secretion of sexual hormones in the central nervous system (ENDOCRINOLOGY, vol. 140, p. 5171 (1999)).

As for the effects mediated by NPY Y5 receptor, fat accumulation effects including orexigenic effect are prominent (NATURE, vol. 382, p. 168 (1996); AMERICAN JOURNAL OF PHYSIOLOGY, vol. 277, p. R1428 (1999)). It is also reported that the NPY Y5 receptor mediates some CNS effects, such as seizure and epilepsy, or pain and morphine withdrawal symptoms, and the control of circadian rhythm (NATURE MEDICINE, vol. 3, p. 761 (1997); PROCEEDINGS OF THE NATIONAL ACADEMY OF SCIENCES OF THE UNITED STATES OF AMERICA, vol. 96, p. 13518 (1999); THE JOURNAL OF PHARMACOLOGY AND EXPERIMENTAL THERAPEUTICS, vol. 284, p. 633 (1998); THE JOURNAL OF NEUROSCIENCE, vol. 21, p. 5367 (2001). In addition, diuretic effect and hypoglycemic effect in the periphery are reported (BRITISH JOURNAL OF PHARMACOLOGY, vol. 120, p. 1335 (1998); ENDOCRINOLOGY, vol. 139, p. 3018 (1998)). NPY is also reported to enhance cardiac hypertrophy as a result of the sympathetic accentuation (PROCEEDINGS OF THE NATIONAL ACADEMY OF SCIENCES OF THE UNITED STATES OF AMERICA, vol. 97, p. 1595 (2000)).

The effects of NPY are expressed when NPY binds to the NPY receptors in the central or peripheral nervous system. Therefore, the action of NPY can be prevented by blocking its binding to NPY receptors. For this reason, it is expected that substances antagonize NPY binding to NPY receptors may be useful for the prophylaxis or treatment of various diseases related to NPY, for example cardiovascular disorders such as angina, acute or congestive heart failure, myocardial infarction, hypertension, nephropathy, electrolyte abnormality, vasospasm, etc., central nervous system disorders such as bulimia, depression, anxiety, seizure, epilepsy, dementia, pain, alcoholism, drug withdrawal, circadian rhythm disorders, schizophrenia, memory impairment, sleep disorders, cognitive impairment, etc., metabolic diseases such as obesity, diabetes, hormone abnormality, gout, fatty liver, etc., genital or reproductive disorders such as infertility, preterm labor, sexual dysfunction, etc., gastro-intestinal disorders, respiratory disorders, inflammatory diseases or glaucoma, and the like. (TRENDS IN PHARMACOLOGICAL SCIENCES, vol. 15, p. 153 (1994); LIFE SCIENCE, vol. 55, p. 551 (1994); DRUGS, vol. 52, p. 371 (1996); THE JOURNAL OF ALLERGY AND CLINICAL IMMUNOLOGY, vol. 101, p. S345 (1998); NATURE, vol. 396, p. 366 (1998); THE JOURNAL OF PHARMACOLOGY AND EXPERIMENTAL THERAPEUTICS, vol. 284, p. 633 (1998); TRENDS IN PHARMACOLOGICAL SCIENCES, vol. 20, p. 104 (1999); PROCEEDINGS OF THE NATIONAL ACADEMY OF SCIENCES OF THE UNITED STATES OF AMERICA, vol. 97, p. 1595 (2000); THE JOURNAL OF NEUROSCIENCE, vol. 21, p. 5367 (2001); PHARMACOLOGY & THERAPEUTICS, vol. 65, p. 397 (1995); ENDOCRINOLOGY, vol. 140, p. 4046 (1999); AMERICAN JOURNAL OF PHYSIOLOGY, vol. 280, p. R1061 (2001); AMERICAN JOURNAL OF PHYSIOLOGY, vol. 278, p. R1627 (2000); CURRENT OPINION IN CLINICAL NUTRITION AND METABOLIC CARE, vol. 2, p. 425 (1999); CURRENT RHEUMATOLOGY REPORTS, vol. 3, p. 101 (2001), AMERICAN JOURNAL OF RESPIRATORY AND CRITICAL CARE MEDICINE, vol. 165, p. 1217 (2002).

It was recently found that, as a result of the study by the present inventors, certain NPY receptor antagonists are useful for the prophylaxis or treatment of hypercholesterolemia, hyperlipidemia and arteriosclerosis (International application publication WO99/27965).

International application publications WO00/27845 (Patent literature 1) and WO01/14376 (Patent literature 2) disclose a variety of carboxamide derivatives, and mentions that the derivatives have excellent NPY receptor antagonistic actions. In addition, international application publication WO02/48152 (Patent literature 3) discloses a variety of spiro [isobenzofuran-1,4'-piperidin]-3-one derivatives, and reports that the derivatives regulate NPY binding to NPY receptor. In those publications, however, there, is no description of the compounds of the present invention.

DISCLOSURE OF THE INVENTION

An object of the present invention is to provide a medicine having an NPY antagonist activity.

The present inventors have found that a compound of the formula (I):

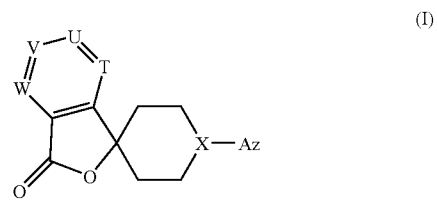

(wherein Az is a group comprising a monocyclic azole or a bicyclic aromatic ring of the same or different fused azoles, which is optionally substituted by a substituent selected from the group consisting of halogen, cyano, lower alkyl, halo-lower alkyl, hydro x, lower alkoxy, halo-lower alkoxy, lower alkoxycarbonyl, lower alkylsulfonyl, lower alkylsulfonyloxy, —N(R$^1$)R$^2$ and -Q$^1$-Ar$^1$;

Ar$^1$ is aryl or heteroaryl, any of which is optionally substituted by a substituent selected from the group consisting of halogen, nitro, oxo, hydroxy, lower alkyl, halo-lower alkyl, hydroxy-lower alkyl, cyclo-lower alkyl, lower alkenyl, lower alkoxy, halo-lower alkoxy, lower alkylthio, lower alkylsulfonyl, carboxyl, lower alkanoyl, lower alkoxycarbonyl, lower alkanoylamino and -Q$^2$-Ar$^2$;

Ar$^2$ is aryl or heteroaryl, any of which is optionally substituted by a substituent selected from the group consisting of halogen, cyano, lower alkyl, halo-lower alkyl, hydroxy-lower alkyl, hydroxy, lower alkoxy, halo-lower alkoxy, lower alkylamino, di-lower alkylamino, lower alkanoyl and aryl;

Q$^1$ and Q$^2$ are independently a single bond, oxygen atom, carbonyl or —N(R$^3$)—;

R$^1$ and R$^2$ are independently hydrogen atom or lower alkyl, or R$^1$ and R$^2$, taken together, form lower alkylene which may be interrupted by oxygen atom, sulfur atom or imino;

R$^3$ is hydrogen atom or lower alkyl;

T, U, V and W are independently methine or nitrogen atom, said methane being optionally substituted by a substituent selected from the group consisting of halogen, lower alkyl, halo-lower alkyl, hydroxy, lower alkoxy and halo-lower alkoxy, and at least two of T, U, V and W are said methine groups; and X is nitrogen atom or methine), or a salt or ester thereof, has an NPY antagonist activity, particularly antagonist activity against NPY Y5 receptor, and show excellent pharmacokinetics such as transport into brain or transport to cerebrospinal fluid. Based on these findings, the present invention has been completed.

Compounds of the present invention (I) exhibit NPY antagonist effects especially on NPY Y5 receptors and show excellent pharmacokinetics such as transport into brain or transport to cerebrospinal fluid, etc., and they are highly safe. Thus, they are useful for the treatment of various diseases related to NPY, for example, cardiovascular disorders such as angina, acute or congestive heart failure, myocardial infarction, hypertension, nephropathy, electrolyte abnormality, vasospasm, arteriosclerosis, etc.; central nervous system disorders such as bulimia, depression, anxiety, seizure, epilepsy, dementia, pain, alcoholism, drug withdrawal, circadian rhythm disorders, schizophrenia, memory impairment, sleep disorders, cognitive impairment, etc.; metabolic diseases such as obesity, diabetes, hormone abnormality, hypercholesterolemia, hyperlipemia, gout, fatty liver, etc.; genital or reproductive disorders such as infertility, preterm labor, sexual dysfunction, etc.; gastro-intestinal disorders; respiratory disorder; inflammatory diseases or glaucoma, and the like; also for example, atherosclerosis; hypogonadism; hyperandrogenism; polycystic ovary syndrome; hirsutism; gastro-intestinal motility disorder; obesity-related gastroesophageal reflux; obesity hypoventilation (Pickwickian syndrome); sleep apnea; inflammation; systemic inflammation of the vasculature; osteoarthritis; insulin resistance; bronchoconstriction; alcohol preference; metabolic syndrome (syndrome X); Alzheimer's disease; cardiac hypertrophy; left ventricular hypertrophy; hypertriglyceridemia; low HDL cholesterol; cardiovascular disorders such as coronary heart disease (CHD), cerebrovascular disease, stroke, peripheral vascular disease, and sudden death; gallbladder diseases; cancer (breast, endometrial, colon); breathlessness; hyperuricemia; impaired fertility; low back pain; increased anesthetic risk, and the like; renal system diseases; renal abnormalities such as dysfunction in body fluid flow, abnormalities of material transportation, and renal failure; shock; arrhythmia; symptoms related to surge in sympathomimetic activity during or after operation on coronary artery or gastrointestinal tracts; diseases related to brain or central nervous system, such as cerebral infarction, neurodegeneration, cerebral stroke, cerebrovascular spasm or cerebral hemorrhage; symptoms related to pain or nociception; diseases related to abnormalities in gastrointestinal motility or secretion, such as various ileuses, urinary incontinence, and Crohn's disease; eating disorders such as anorexia and bulimia; inflammatory symptoms or diseases; asthma; bronchiole constriction; or diseases related to abnormal secretion of hormones such as luteinizing hormone, growth hormone, insulin, and luteotropic hormone.

Particularly, the compounds (I) of the present invention are useful for the treatment of, for example, bulimia, obesity, diabetes.

The present invention relates to compounds of the formula (I), salts thereof, esters thereof and their production or use.

The means of terms used in the present specification are defined and more detailed description of this invention is described in the following.

"Monocyclic azole" refers to a monocyclic azole comprising pyrrole, imidazole, pyrazole, triazole and tetrazole.

"Bicyclic aromatic ring of the same or different fused azoles" refers to a bicyclic aromatic ring wherein the said same or different azoles are ortho-fused, including, for example, 1,5-dihydropyrrolo[2,3-c]pyrrole, 1H-pyrrolo[1,2-b]pyrazole, 1,6-dihydropyrrolo[2,3-c]pyrazole, 1,4-dihydropyrrolo[3,2-c]pyrazole, 1H-pyrrolo[1,2-a]imidazole, 1,5-dihydropyrrolo[3,4-d]imidazole, 1,4-dihydropyrrolo[2,3-d][1,2,3]triazole, 1H-pyrrolo[1,2-b][1,2,4]triazole, 1H-imidazo[1,2-b]pyrazole, 1,4-dihydroimidazo[4,5-c]pyrazole, 1H-imidazo[1,2-a]imidazole, 1,4-dihydroimidazo[4,5-d][1,2,3]triazole, 1H-imidazo[1,2-b][1,2,4]triazole, 1H-pyrazolo[2,3-b]pyrazole, 1H-pyrazolo[2,3-b][1,2,4]triazole, 1H-1,2,4-triazolo[2,3-b][1,2,4]triazole or a tautomer thereof.

"Halogen" refers to fluorine, chlorine, bromine and iodine.

"Lower alkyl" refers to a straight- or branched-chain alkyl group having one to six carbon atoms, and its examples are methyl, ethyl, propyl, isopropyl, butyl, isobutyl, sec-butyl, tert-butyl, pentyl, isopentyl, hexyl, isohexyl and the like.

"Halo-lower alkyl" refers to said lower alkyl substituted by identically or differently one, two or more, preferably one to three said halogen atom(s) at the substitutable, arbitrary position(s), and its examples are fluoromethyl, difluoromethyl, trifluoromethyl, 2-fluoroethyl, 1,2-difluoroethyl, chloromethyl, 2-chloroethyl, 1,2-dichloroethyl, bromomethyl, iodomethyl and the like.

"Lower alkoxy" refers to straight- or branched-chain alkoxy having one to six carbon atoms and its examples are methoxy, ethoxy, propoxy, isopropoxy, butoxy, sec-butoxy, isobutoxy, tert-butoxy, pentyloxy, isopentyloxy, hexyloxy, isohexyloxy and the like.

"Halo-lower alkoxy" refers to said lower alkoxy substituted by identically or differently one, two or more, preferably one to, three said halogen atom(s) at substitutable, arbitrary position(s), and its examples are fluoromethoxy, difluoromethoxy, trifluoromethoxy, 2-fluoroethoxy, 1,2-difluoroethoxy, chloromethoxy, 2-chloroethoxy, 1,2-dichloroethoxy, bromomethoxy, iodomethoxy and the like.

"Lower alkoxycarbonyl" refers to an alkoxycarbonyl group containing said lower alkoxy, that is, an alkoxycarbonyl group having two to seven carbon atoms, and its examples are methoxycarbonyl, ethoxycarbonyl, propoxycarbonyl, isopropoxycarbonyl, butoxycarbonyl, isobutoxycarbonyl, tert-butoxycarbonyl, pentyloxycarbonyl and the like.

"Lower alkylsulfonyl" refers to a straight- or branched-chain alkylsulfonyl group having one to six carbon atoms, and its examples are methylsulfonyl, ethylsulfonyl, propylsulfonyl, isopropylsulfonyl, butylsulfonyl, sec-butylsulfonyl, isobutylsulfonyl, tert-butylsulfonyl, pentylsulfonyl, isopentylsulfonyl, hexylsulfonyl, isohexylsulfonyl and the like.

"Lower alkylsulfonyloxy" refers to a straight- or branched-chain alkylsulfonyloxy group having one to six carbon atoms, and its examples are methylsulfonyloxy, ethylsulfonyloxy, propylsulfonyloxy, isopropylsulfonyloxy, butylsulfonyloxy, sec-butylsulfonyloxy, isobutylsulfonyloxy, tert-butylsulfonyloxy, pentylsulfonyloxy, isopentylsulfonyloxy, hexylsulfonyloxy, isohexylsulfonyloxy and the like.

"Hydroxy-lower alkyl" refers to said lower alkyl substituted by one, two or more, preferably one or two hydroxy at substitutable, arbitrary position(s), and its examples are hydroxymethyl, 2-hydroxyethyl, 1-hydroxy-1-methylethyl, 1,2-dihydroxyethyl, 3-hydroxypropyl and the like.

"Cyclo-lower alkyl" refers to a cycloalkyl group having three to six carbon atoms, and its examples are cyclopropyl, cyclobutyl, cyclopentyl, cyclohexyl and the like.

"Lower alkenyl" refers to a straight- or branched-chain alkenyl group having two to six carbon atoms, and its examples are vinyl, 1-propenyl, 2-propenyl, isopropenyl, 3-butenyl, 2-butenyl, 1-butenyl, 1-methyl-2-propenyl, 1-methyl-1-propenyl, 1-ethyl-1-ethenyl, 2-methyl-2-propenyl, 2-methyl-1-propenyl, 3-methyl-2-butenyl, 4-pentenyl and the like.

"Lower alkylthio" refers to straight- or branched-chain alkylthio having one to six carbon atoms, and its examples are methylthio, ethylthio, propylthio, isopropylthio, butylthio, sec-butylthio, isobutylthio, tert-butylthio, pentylthio, isopentylthio, hexylthio, isohexylthio and the like.

"Lower alkanoyl" refers to an alkanoyl group containing said lower alkyl, that is, an alkanoyl group having two to seven carbon atoms, and its examples are acetyl, propionyl, butyryl, isobutyryl, valeryl, isovaleryl, pivaloyl and the like.

"Lower alkanoylamino" refers to an amino group mono-substituted by said lower alkanoyl, and its examples are acetylamino, propionylamino, butyrylamino, isobutyrylamino, valerylamino, isovalerylamino, pivaloylamino and the like.

"Aryl" refers to phenyl, naphthyl and the like.

"Heteroaryl" refers to 5- or 6-membered monocyclic heteroaromatic group which contains one, two or more, preferably one to three hetero atom(s) identically or differently selected from the group consisting of oxygen atom, nitrogen atom and sulfur atom; or fused cyclic heteroaromatic group, where said monocyclic heteroaromatic group is fused with said aryl group or fused each other with the same or different said monocyclic heteroaromatic group, and its examples are pyrrolyl, furyl, thienyl, imidazolyl, pyrazolyl, thiazolyl, isothiazolyl, oxazolyl, isoxazolyl, 1,2,3-triazolyl, 1,2,4-triazolyl, tetrazolyl, 1,2,3-oxadiazolyl, 1,2,4-oxadiazolyl, 1,2,3-thiadiazolyl, 1,2,4-thiadiazolyl, 1,3,4-thiadiazolyl, pyridyl, pyrazinyl, pyrimidinyl, pyridazinyl, 1,2,4-triazinyl, 1,3,5-triazinyl, indolyl, benzofuranyl, benzothienyl, benzoimidazolyl, benzoxazolyl, benzoisoxazolyl, benzothiazolyl, benzoisothiazolyl, indazolyl, purinyl, quinolyl, isoquinolyl, phthalazinyl, naphthylidinyl, quinoxalinyl, quinazolinyl, cinnolinyl, pteridinyl, pyrido[3,2-b]pyridyl and the like.

"Lower alkylamino" refers to an amino group mono-substituted by said lower alkyl, and its examples are methylamino, ethylamino, propylamino, isopropylamino, butylamino, sec-butylamino, tert-butylamino and the like.

"Di-lower alkylamino" refers to an amino group di-substituted by the same or different said lower alkyl, and its examples are dimethylamino, diethylamino, ethylmethylamino, dipropylamino, methylpropylamino, diisopropylamino and the like.

"Lower alkylene which may be interrupted by oxygen atom, sulfur atom or imino" refers to an alkylene group of C2 to C5, which is not intervened or interrupted by one, two or more, preferably one oxygen atom, sulfur atom or imino at optional and intervention capable position(s) of, said alkylene chain, and its examples, are ethylene, trimethylene, tetramethylene, pentamethylene, 2-oxatetramethylene, 2-oxapentamethylene, 3-oxapentamethylene, 2-thiatetramethylene, 2-thiapentamethylene, 3-thiapentamethylene, 2-azatetramethylene, 2-azapentamethylene, 3-azapentamethylene and the like.

"Aralkyl" refers to said lower alkyl substituted by one, two or more, preferably one said aryl at substitutable, arbitrary position(s), and its examples are benzyl, 1-phenylethyl, phenethyl, 1-naphthylmethyl, 2-naphthylmethyl and the like. The esters of compounds of formula (I) refer to, for example, the pharmaceutically acceptable, common esters of said carboxyl group when the compound has a carboxyl group, and examples thereof are esters with lower alkyl (e.g. methyl, ethyl, propyl, isopropyl, butyl, sec-butyl, tert-butyl, pentyl, isopentyl, neopentyl, cyclopropyl, cyclobutyl, cyclopentyl), esters with aralkyl (e.g. benzyl, phenethyl), esters with lower alkenyl (e.g. allyl, 2-butenyl), esters with lower alkoxy-lower alkyl (e.g. methoxymethyl, 2-methoxyethyl, 2-ethoxyethyl), esters with lower alkanoyloxy-lower alkyl (e.g. acetoxymethyl, pivaloyloxymethyl, 1-pivaloyloxyethyl), esters with lower alkoxycarbonyl-lower-alkyl (e.g. methoxycarbonylmethyl, isopropoxycarbonylmethyl), esters with carboxy-lower alkyl (e.g. carboxymethyl), esters with lower alkoxycarbonyloxy-lower alkyl (e.g. 1-(ethoxycarbonyloxy)ethyl 1-(cyclohexyloxycarbonyloxy)ethyl), esters with carbamoyloxy-lower alkyl (e.g. carbamoyloxymethyl), esters with phthalidyl, esters with (5-substituted-2-oxo-1,3-dioxol-4-yl) methyl (e.g. (5-methyl-2-oxo-1,3-dioxol-4-yl)methyl) and the like.

The salts of, compounds of formula (I) refer to the pharmaceutically acceptable, common salts, and examples thereof are base addition salt to said carboxyl group when the compound has a carboxyl group, or acid addition salt to said amino or basic heterocyclyl when the compound has an amino or basic heterocyclyl group and the like.

Said base addition salts include salts with alkali metals (e.g. sodium, potassium); salts with alkaline earth metals (e.g. calcium, magnesium); ammonium salts; salts with organic amines (e.g. trimethylamine, triethylamine, dicyclohexylamine, ethanolamine, diethanolamine, triethanolamine, procaine, N,N'-dibenzylethylenediamine) and the like.

Said acid addition salts include salts with inorganic acids (e.g. hydrochloric acid, sulfuric acid, nitric acid, phosphoric acid, perchloric acid), salts with organic acids (e.g. maleic acid, fumaric acid, tartaric acid, citric acid, ascorbic acid, trifluoroacetic acid), salts with sulfonic acids (e.g. methanesulfonic acid, isethionic acid, benzenesulfonic acid, p-toluenesulfonic acid) and the like.

"An agent for treatment" refers to a medicament which is employed for the treatment and/or prophylaxis of various diseases.

In order to disclose the aforesaid compounds of the general formula (I) of the present invention more specifically, the various symbols used in the formula (I) are explained in more detail by presenting preferred embodiments.

Az is a group comprising a monocyclic azole or a bicyclic aromatic ring of the same or different fused azoles, which is optionally substituted by a substituent selected from the group consisting of halogen, cyano, lower alkyl, halo-lower alkyl, hydroxy, lower alkoxy, halo-lower alkoxy, lower alkoxycarbonyl, lower alkylsulfonyl, lower alkylsulfonyloxy, —N($R^1$)$R^2$ and -$Q^1$-$Ar^1$.

"A group comprising a monocyclic azole or bicyclic aromatic ring of the same or different azoles, which is optionally substituted by a substituent selected from the group consisting of halogen, cyano, lower alkyl, halo-lower alkyl, hydroxy, lower alkoxy, halo-lower alkoxy, lower alkoxycarbonyl, lower alkylsulfonyl, lower alkylsulfonyloxy, —N($R^1$)$R^2$ and -$Q^1$-$Ar^{1}$'" means an unsubstituted monocyclic azole described above, a monocyclic azole having a substituent at substitutable, arbitrary position(s), a bicyclic aromatic ring of said unsubstituted same or different fused azoles, or a bicyclic aromatic ring of said same or different fused azoles having one, two or more substituent(s), preferably one or two substituents, selected from the group consisting of halogen, cyano, lower alkyl, halo-lower alkyl, hydroxy, lower alkoxy, halo-lower alkoxy, lower alkoxycarbonyl, lower alkylsulfonyl, lower alkylsulfonyloxy, —N($R^1$)$R^2$ and -$Q^1$-$Ar^{1}$''' at substitutable, arbitrary position(s).

Halogen as said substituent preferably includes, for example, fluorine, chlorine and; the like.

Lower alkyl as said substituent preferably includes, for example, methyl, ethyl and the like.

Halo-lower alkyl as said substituent preferably includes, for example, difluoromethyl, trifluoromethyl and the like.

Lower alkoxy as said substituent preferably includes, for example, methoxy, ethoxy and the like.

Halo-lower alkoxy as said substituent preferably includes, for example, difluoromethoxy, trifluoromethoxy and the like.

Lower alkoxycarbonyl as said substituent preferably includes, for example, methoxycarbonyl, ethoxycarbonyl and the like.

Lower alkylsulfonyl as said substituent preferably includes, for example, methylsulfonyl, ethylsulfonyl and the like.

Lower alkylsulfonyloxy as said substituent preferably includes, for example, methylsulfonyloxy, ethylsulfonyloxy and the like.

In a group of the formula: —N($R^1$)$R^2$ as said substituent, $R^1$ and $R^2$ are independently hydrogen atom or lower alkyl, or $R^1$ and $R^2$, taken together, form lower alkylene which may be interrupted by oxygen atom, sulfur atom or imino.

Lower alkyl as $R^1$ or $R^2$ preferably includes, for example, methyl, ethyl, propyl and the like.

"Lower alkylene which may be interrupted by oxygen atom, sulfur atom or imino" formed by taking $R^1$ and $R^2$ together preferably includes pentamethylene, 3-oxapentamethylene and the like, and when taken together with the adjacent nitrogen atom, it forms piperidino, morpholino and the like.

The preferred embodiment of $R^1$ and $R^2$ includes the case where at least one of $R^1$ or $R^2$ is lower alkyl, or the case where $R^1$ and $R^2$, taken together, form lower alkylene which may be interrupted by oxygen atom, sulfur atom or imino.

Thus, a group of the formula: —N($R^1$)$R^2$ as said substituent includes, for; example, amino, methylamino, ethylamino, propylamino, dimethylamino, diethylamino, ethylmethylamino, 1-azetidinyl, 1-pyrrolidinyl, piperidino, morpholino, thiomorpholino, 1-piperazinyl and the like, among which preferred are methylamino, dimethylamino, piperidino, morpholino and the like.

In a group of the formula: -$Q^1$-$Ar^1$ as said substituent, $Ar^1$ is aryl or heteroaryl, any of which is optionally substituted by a substituent selected from the group consisting of halogen, nitro, oxo, hydroxy, lower alkyl, halo-lower alkyl, hydroxy-lower alkyl, cyclo-lower alkyl, lower alkenyl, lower alkoxy, halo-lower alkoxy, lower alkylthio, lower alkylsulfonyl, carboxyl, lower alkanoyl, lower alkoxycarbonyl, lower alkanoylamino and -$Q^2$-$Ar^2$; and $Q^1$ is a single bond, oxygen atom, carbonyl or —N($R^3$)—.

"Aryl or heteroaryl, any of which is optionally substituted by a substituent selected from the group consisting of halogen, nitro, oxo, hydroxy, lower alkyl, halo-lower alkyl, hydroxyl-lower alkyl, cyclo-lower alkyl, lower alkenyl, lower alkoxy, halo-lower alkoxy, lower alkylthio, lower alkyl sulfonyl, carboxyl, lower alkanoyl, lower alkoxycarbonyl, lower alkanoylamino and -$Q^2$-$Ar^2$" includes an unsubstituted aryl group described above, an unsubstituted heteroaryl group described above, an aryl group described above or a heteroaryl group, the last two groups optionally having one, two or more, preferably one or two substituents, which are the same or different, selected from the group consisting of halogen, nitro, oxo, hydroxy, lower alkyl, halo-lower alkyl, hydroxy-lower alkyl, cyclo-lower alkyl, lower alkenyl, lower alkoxy, halo-lower alkoxy, lower alkylthio, lower alkylsulfonyl, carboxyl, lower alkanoyl, lower alkoxycarbonyl, lower alkanoylamino and -$Q^2$-$Ar^2$.

Halogen as said substituent preferably includes, for example, fluorine, chlorine, bromine and the like.

Lower alkyl as said substituent preferably includes, for example, methyl, ethyl, propyl, isopropyl and the like.

Halo-lower alkyl as said substituent preferably includes, for example, difluoromethyl, trifluoromethyl and the like.

Hydroxy-lower alkyl as said substituent preferably includes, for example, hydroxymethyl, 2-hydroxyethyl, 1-hydroxy-1-methylethyl and the like.

Cyclo-lower alkyl as said substituent preferably includes, for example, cyclopropyl, cyclobutyl and the like.

Lower alkenyl as said substituent preferably includes, for example, vinyl, 1-propenyl, 2-methyl-1-propenyl and the like.

Lower alkoxy as said substituent preferably includes, for example, methoxy, ethoxy and the like.

Halo-lower alkoxy as said substituent preferably includes, for example, fluoromethoxy, difluoromethoxy, trifluoromethoxy and the like.

Lower alkylthio as said substituent preferably includes, for example, methylthio, ethylthio and the like.

Lower alkylsulfonyl as said substituent preferably includes, for example, methylsulfony, ethylsulfonyl, propylsulfonyl and the like.

Lower alkanoyl as said substituent preferably includes, for example, acetyl, propionyl and the like.

Lower alkoxycarbonyl as said substituent preferably includes, for example, methoxycarbonyl, ethoxycarbonyl and the like.

Lower alkanoylamino as said substituent preferably includes, for example, acetylamino, propanoylamino and the like.

In a group of the formula: -$Q^2$-$Ar^2$ as said substituent, $Ar^2$ is aryl or heteroaryl, any of which is optionally substituted by a substituent selected from the group consisting of halogen, cyano, lower alkyl, halo-lower alkyl, hydroxy-lower alkyl, hydroxy, lower alkoxy, halo-lower alkoxy, lower alkylamino, di-lower alkylamino, lower alkanoyl and aryl; and $Q^2$ is a single bond, oxygen atom, carbonyl or —N($R^3$)—.

"Aryl or heteroaryl, any of which is optionally substituted by a substituent selected from the group consisting of halogen, cyano, lower alkyl, halo-lower alkyl, hydroxyl-lower alkyl, hydroxy, lower alkoxy, halo-lower alkoxy, lower alkylamino, di-lower alkylamino, lower alkanoyl and aryl" refers to an unsubstituted aryl group described above, an unsubstituted heteroaryl group described above, an aryl group described above or a heteroaryl group described above, the last two groups being optionally substituted by one, two or more, preferably one or two substituent(s) identically or differently selected from the group consisting of halogen, cyano, lower alkyl, halo-lower alkyl, hydroxy-lower alkyl, hydroxy, lower alkoxy, halo-lower alkoxy, lower alkylamino, di-lower alkylamino, lower alkanoyl and aryl at substitutable, arbitrary position(s).

Halogen as said substituent preferably includes, for example, fluorine, chlorine and the like.

Lower alkyl as said substituent preferably includes, for example, methyl, ethyl, propyl, isopropyl and the like.

Halo-lower alkyl as said substituent preferably includes, for example, difluoromethyl, trifluoromethyl and the like.

Hydroxy-lower alkyl as said substituent preferably includes, for example, hydroxymethyl, 2-hydroxyethyl, 1-hydroxy-1-methylethyl and the like.

Lower alkoxy as said substituent preferably includes, for example, methoxy, ethoxy and the like.

Halo-lower alkoxy as said substituent preferably includes, for example, fluoromethoxy, difluoromethoxy, trifluoromethoxy and the like.

Lower alkylamino as said substituent preferably includes, for example, methylamino, ethylamino and the like.

Di-lower alkylamino as said substituent preferably includes, for example, dimethylamino, diethylamino and the like.

Lower alkanoyl as said substituent preferably includes, for example, acetyl, proionyl and the like.

Aryl as said substituent preferably includes, for example, phenyl.

Substituent of $Ar^2$ preferably includes, for example, halogen, cyano, lower alkyl, halo-lower alkyl, hydroxyl-lower alkyl, hydroxy, halo-lower alkoxy and the like.

Aryl represented by $Ar^2$ preferably includes, for example, phenyl, and heteroaryl represented by $Ar^2$ preferably includes pyridyl, quinolyl and the like.

In a group of the formula —N($R^3$)— of $Q^1$ and $Q^2$, $R^3$ is hydrogen atom or lower alkyl.

$R^3$ preferably includes, for example, hydrogen atom, methyl, ethyl and the like.

$Q^2$ preferably includes, for example, a single bond.

Substituent of $Ar^1$ includes, for example, halogen, hydroxy, lower alkyl, halo-lower alkyl, lower alkenyl, lower alkoxy, lower alkanoyl, -$Q^2$-$Ar^2$ and the like, more preferably halogen, hydroxy, halo lower alkyl, lower alkoxy, -$Q^2$-$Ar^2$- and the like.

Aryl as $Ar^1$ preferably includes, for example, phenyl, naphthyl and the like, and heteroaryl as $Ar^1$ preferably includes, for example, imidazolyl, furyl, thienyl, pyrazolyl, 1,2,3-triazolyl, 1,2,4-triazolyl, thiazolyl, oxazolyl, isoxazolyl, 1,2,4-oxadiazolyl, 1,3,4-oxadiazolyl, 1,2,4-thiadiazolyl, 1,3,4-thiadiazolyl, pyridyl, pyrazinyl, pyrimidinyl, benzofuranyl, quinolyl, isoquinolyl, and the like, more preferably pyrazolyl, pyridyl, pyrimidinyl, pyrazinyl, quinolyl, isoquinolyl and the like.

Consequently, $Ar^1$ includes, for example, phenyl, 2-fluorophenyl, 3-fluorophenyl, 4-fluorophenyl, 2,3-difluorophenyl, 2,4-difluorophenyl, 2,5-difluorophenyl, 2,6-difluorophenyl, 3,5-difluorophenyl, 2-chlorophenyl, 3-chlorophenyl, 4-chlorophenyl, 2-bromophenyl, 3-bromophenyl, 4-bromophenyl, 2-chloro-4-fluorophenyl, 2-chloro-5-fluorophenyl, 2-chloro-6-fluorophenyl, 2-bromo-4-fluorophenyl, 2-bromo-5-fluorophenyl, 2-methylphenyl, 3-methylphenyl, 4-methylphenyl, 5-fluoro-2-methylphenyl, 3-fluoromethylphenyl, 2-trifluoromethylphenyl, 3-trifluoromethylphenyl, 4-trifluoromethylphenyl, 2-methoxyphenyl, 3-methoxyphenyl, 4-methoxyphenyl, 5-fluoro-2-methoxyphenyl, 3-fluoromethoxyphenyl, 2-difluoromethoxyphenyl, 3-difluoromethoxyphenyl, 3-hydroxy-4-fluorophenyl, 2-hydroxymethylphenyl, 3-hydroxymethylphenyl, 3-hydroxyphenyl, 4-hydroxyphenyl, 1-naphthyl, 2-fluoro-1-naphthyl, 3-fluoro-1-naphthyl, 4-fluoro-1-naphthyl, 5-fluoro-1-naphthyl, 6-fluoro-1-naphthyl, 7-fluoro-1-naphthyl, 8-fluoro-1-naphthyl, 2-naphthyl, 1-fluoro-2-naphthyl, 3-fluoro-2-naphthyl, 4-fluoro-2-naphthyl, 5-fluoro-2-naphthyl, 6-fluoro-2-naphthyl, 7-fluoro-2-naphthyl, 8-fluoro-2-naphthyl, 2-imidazolyl, 4-phenylimidazol-2-yl, 4-(2-fluorophenyl)imidazol-2-yl, 4-(3-fluorophenyl)imidazol-2-yl, 4-(4-fluorophenyl)imidazol-2-yl, 2-furyl, 4-phenylfuran-2-yl, 4-(2-fluorophenyl)furan-2-yl, 4-(3-fluorophenyl)furan-2-yl, 4-(4-fluorophenyl)furan-2-yl, 2-thienyl, 4-phenylthiophen-2-yl, 4-(2-fluorophenyl)thiophen-2-yl, 4-(3-fluorophenyl)thiophen-2-yl, 4-(4-fluorophenyl)thiophen-2-yl, 3-pyrazolyl, 1-phenylpyrazol-3-yl, 1-(2-fluorophenyl)pyrazol-3-yl, 1-(3-fluorophenyl)pyrazol-3-yl, 1-(4-fluorophenyl)pyrazol-3-yl, 5-phenylpyrazol-3-yl, 5-(2-fluorophenyl)pyrazol-3-yl, 5-(3-fluorophenyl)pyrazol-3-yl, 5-(4-fluorophenyl)pyrazol-3-yl, 4-pyrazolyl, 1-phenylpyrazol-4-yl, 1-(2-fluorophenyl)pyrazol-4-yl, 1-(3-fluorophenyl)pyrazol-4-yl, 1-(4-fluorophenyl)pyrazol-4-yl, 1,2,4-oxadiazol-5-yl, 3-phenyl-1,2,4-oxadiazol-5-yl, 1,3,4-oxadiazol-2-yl, 2-phenyl-1,3,4-oxadiazol-5-yl, 1,2,4-thiadiazol-5-yl, 3-phenyl-1,2,4-thiadiazol-5-yl, 1,3,4-thiadiazol-2-yl, 2-phenyl-1,3,4-thiadiazol-5-yl, 2-pyridyl, 3-phenylpyridin-2-yl, 4-phenylpyridin-2-yl, 5-phenylpyridin-2-yl, 6-phenylpyridin-2-yl, 3-pyridyl, 2-phenylpyridin-3-yl, 4-phenylpyridin-3-yl, 5-phenylpyridin-3-yl, 4-pyridyl, 2-phenylpyridin-4-yl, 3-phenylpyridin-4-yl, 2-phenylpyridin-5-yl, 6-fluoro-2-pyridyl, 2-fluoro-4-pyridyl, 2-fluoro-5-pyridyl, 5-fluoro-2-pyridyl, 2-pyrimidinyl, 4-phenylpyrimidin-2-yl, 5-phenylpyrimidin-2-yl, 4-pyrimidinyl, 2-phenylpyrimidin-4-yl, 2-(2-fluorophenyl)pyrimidin-4-yl, 2-(4-fluorophenyl)pyrimidin-4-yl, 5-phenylpyrimidin-4-yl, 6-phenylpyrimidin-4-yl, 5-pyrimidinyl, 2-phenylpyrimidin-5-yl, 4-phenylpyrimidin-5-yl, 2-pyrazinyl, 3-phenylpyrazin-2-yl, 5-phenylpyrazin-2-yl, 6-phenylpyrazin-2-yl, 4-benzo[b]furanyl, 5-benzo[b]furanyl, 7-benzo[b]furanyl, 2-quinolyl, 3-quinolyl, 4-quinolyl, 5-quinolyl, 6-quinolyl, 7-quinolyl, 8-quinolyl, 1-isoquinolyl, 3-isoquinolyl, 4-isoquinolyl, 5-isoquinolyl, 6-isoquinolyl, 7-isoquinolyl, 8-isoquinolyl, 2-biphenylyl, 3-biphenylyl, 4-biphenylyl, and the like, and among those, $Ar^1$ preferably includes phenyl, 2-fluorophenyl, 3-fluorophenyl, 4-fluorophenyl, 2,4-difluorophenyl, 2,5-difluorophenyl, 3,5-difluorophenyl, 2-chlorophenyl, 3-chlorophenyl, 3-bromophenyl, 4-bromophenyl, 2-trifluoromethylphenyl, 3-trifluoromethylphenyl, 4-trifluoromethylphenyl, 3-methoxyphenyl, 2-difluoromethoxyphenyl, 3-difluoromethoxyphenyl, 3-hydroxyphenyl, 4-hydroxyphenyl, 2-naphthyl, 3-biphenylyl, 4-biphenylyl, 1-phenylpyrazol-3-yl, 1-phenylpyrazol-4-yl, 4-phenylpyridin-2-yl, 6-phenylpyridin-2-yl, 5-phenylpyridin-3-yl, 2-phenylpyridin-4-yl, 6-fluoro-2-pyridyl, 2-fluoro-5-pyridyl, 5-fluoro-2-pyridyl, 2-phenylpyrimidin-4-yl, 2-(2-fluorophenyl)pyrimidin-4-yl, 2-(4-fluorophenyl)pyrimidin-4-yl, 6-phenylpyrimidin-4-yl, 6-phenylpyrazin-2-yl, 2-quinolyl, 3-quinolyl, 3-isoquinolyl, 3-biphenylyl, 4-biphenylyl, and the like.

$Q^1$ includes, for example, a single bond, an oxygen atom, —$N(R^3)$— and the like, preferably a single bond.

Substituent of a monocyclic azole, or a bicyclic aromatic ring of the same or different fused azoles, represented by Az, includes, for example, halogen, halo-lower alkyl, lower alkoxycarbonyl, —$N(R^1)R^2$, -$Q^1$-$Ar^1$ and the like, preferably -$Q^1$-$Ar^1$ and the like. Az is preferably a monocyclic azole or a bicyclic aromatic ring of the heretofore mentioned same or different fused azoles, which bears -$Q^1$-$Ar^1$.

The monocyclic azole of Az preferably includes, for example, 2-imidazolyl, 4-imidazolyl, 3-pyrazolyl, 4-pyrazolyl, 1,2,4-triazol-3-yl and the like, represented by the following formulae (a).

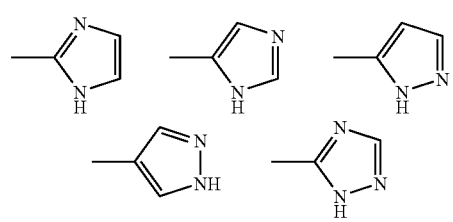

(a)

The bicyclic aromatic ring group of the same or different fused azoles represented by Az preferably includes, for example, groups represented by the following formulae (b);

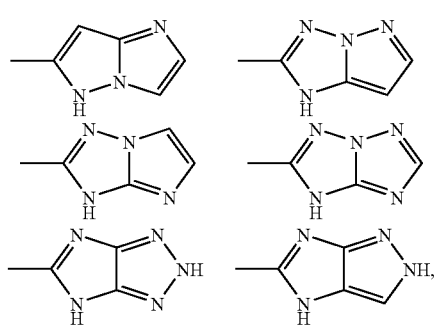

(b)

that is, 5H-imidazo[1,2-b]pyrazol-6-yl, 1H-pyrazolo[2,3-b][1,2,4]triazol-2-yl, 3H-imidazo[1,2-b][1,2,4]triazol-2-yl, 1H-1,2,4-triazolo[2,3-b][1,2,4]triazol-2-yl, 2,4-dihydroimidazo[4,5-d][1,2,3]triazol-5-yl, 2,4-dihydroimidazo[4,5-c]pyrazol-5-yl and the like, preferably 1H-pyrazolo[2,3-b][1,2,4]triazol-2-yl, 2,4-dihydroimidazo[4,5-d][1,2,3]triazol-5-yl, 2,4-dihydroimidazo[4,5-c]pyrazol-5-yl and the like.

More specifically, an optionally substituted monocyclic azole of Az in the formula (I) preferably includes, for example, groups represented by the formulae (a₁):

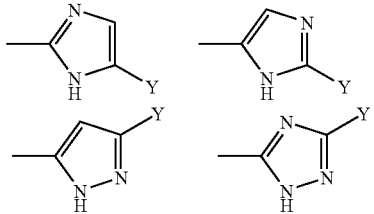

(a₁)

wherein Y is hydrogen atom, halogen, cyano, lower alkyl, halo-lower alkyl, hydroxy, lower alkoxy, halo-lower alkoxy, lower alkoxycarbonyl, lower alkylsulfonyl, lower alkylsulfonyloxy, —N(R¹)R² or -Q¹-Ar¹; and Ar¹, Q¹, R¹ and R² have each the same meaning as defined above.

An optionally substituted bicyclic aromatic ring group of the same or different fused azoles represented by Az in the formula (I) preferably includes, for example, groups represented by the formulae (b₁):

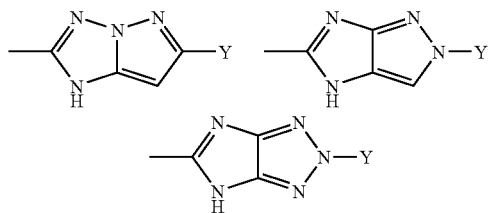

(b₁)

wherein Y has the same meaning as defined above, and the like.

In the above formula (a₁) or (b₁), Y preferably includes -Q¹-Ar¹.

In more detail, Az preferably includes, for example,
4-phenyl-1H-imidazol-2-yl,
4,5-diphenyl-1H-imidazol-2-yl,
4-methyl-5-phenyl-1H-imidazol-2-yl,
4-(2-fluorophenyl)-1H-imidazol-2-yl,
4-(3-fluorophenyl)-1H-imidazol-2-yl,
4-(4-fluorophenyl)-1H-imidazol-2-yl,
4-(2,4-difluorophenyl)-1H-imidazol-2-yl,
4-(2,5-difluorophenyl)-1H-imidazol-2-yl,
4-(3,5-difluorophenyl)-1H-imidazol-2-yl,
4-(2-chlorophenyl)-1H-imidazol-2-yl,
4-(3-chlorophenyl)-1H-imidazol-2-yl,
4-(3-bormophenyl)-1H-imidazol-2-yl,
4-(4-bormophenyl)-1H-imidazol-2-yl,
4-(2-trifluoromethylphenyl)-1H-imidazol-2-yl,
4-(3-trifluoromethylphenyl)-1H-imidazol-2-yl,
4-(4-trifluoromethylphenyl)-1H-imidazol-2-yl,
4-(3-methoxyphenyl)-1H-imidazol-2-yl,
4-(2-difluoromethoxyphenyl)-1H-imidazol-2-yl
4-(3-difluoromethoxyphenyl)-1H-imidazol-2-yl,
4-(3-hydroxyphenyl)-1H-imidazol-2-yl,
4-(4-hydroxyphenyl)-1H-imidazol-2-yl,
4-(2-naphthyl)-1H-imidazol-2-yl,
4-(1-phenylpyrazol-3-yl)-1H-imidazol-2-yl,
4-(1-phenylpyrazol-4-yl)-1H-imidazol-2-yl,
4-(4-phenylpyridin-2-yl)-1H-imidazol-2-yl,
4-(6-phenylpyridin-2-yl)-1H-imidazol-2-yl,
4-(5-phenylpyridin-3-yl)-1H-imidazol-2-yl,
4-(2-phenylpyridin-4-yl)-1H-imidazol-2-yl,
4-(6-fluoropyridin-2-yl)-1H-imidazol-2-yl,
4-(2-fluoropyridin-5-yl)-1H-imidazol-2-yl,
4-(5-fluoropyridin-2-yl)-1H-imidazol-2-yl,
4-(4-fluorophenyl)-5-(3-pyridyl)-1H-imidazol-2-yl,
4-(2-phenylpyrimidin-4-yl)-1H-imidazol-2-yl,
4-(6-phenylpyrimidin-4-yl)-1H-imidazol-2-yl,
4-(6-phenylpyrazin-2-yl)-1H-imidazol-2-yl,
4-(2-quinolyl)-1H-imidazol-2-yl,
4-(3-quinolyl)-1H-imidazol-2-yl,
4-(3-isoquinolyl)-1H-imidazol-2-yl,
4-(3-biphenylyl)-1H-imidazol-2-yl,
4-(4-biphenylyl)-1H-imidazol-2-yl,
2-phenyl-1H-imidazol-4-yl,
2-(2-fluorophenyl)-1H-imidazol-4-yl,
2-(3-fluorophenyl)-1H-imidazol-4-yl,
2-(4-fluorophenyl)-1H-imidazol-4-yl,
2-(2,4-difluorophenyl)-1H-imidazol-4-yl,
2-(2,5-difluorophenyl)-1H-imidazol-4-yl,
2-(3,5-difluorophenyl)-1H-imidazol-4-yl,
2-(2-chlorophenyl)-1H-imidazol-4-yl,
2-(3-chlorophenyl)-1H-imidazol-4-yl,
2-(3-bromophenyl)-1H-imidazol-4-yl,
2-(4-bromophenyl)-1H-imidazol-4-yl,
2-(2-trifluoromethylphenyl)-1H-imidazol-4-yl,
2-(3-trifluoromethylphenyl)-1H-imidazol-4-yl,
2-(4-trifluoromethylphenyl)-1H-imidazol-4-yl,
2-(3-methoxyphenyl)-1H-imidazol-4-yl,
2-(2-difluoromethoxyphenyl)-1H-imidazol-4-yl,
2-(3-difluoromethoxyphenyl)-1H-imidazol-4-yl,
2-(3-hydroxyphenyl)-1H-imidazol-4-yl,
2-(4-hydroxyphenyl)-1H-imidazol-4-yl,
2-(2-naphthyl)-1H-imidazol-4-yl,
2-(1-phenylpyrazol-3-yl)-1H-imidazol-4-yl,
2-(1-phenylpyrazol-4-yl)-1H-imidazol-4-yl,
2-(4-phenylpyridin-2-yl)-1H-imidazol-4-yl,
2-(6-phenylpyridin-2-yl)-1H-imidazol-4-yl,
2-(5-phenylpyridin-3-yl)-1H-imidazol-4-yl,
2-(2-phenylpyridin-4-yl)-1H-imidazol-4-yl,
2-(6-fluoropyridin-2-yl)-1H-imidazol-4-yl,
2-(2-fluoropyridin-5-yl)-1H-imidazol-4-yl,
2-(5-fluoropyridin-2-yl)-1H-imidazol-4-yl,
2-(2-phenylpyrimidin-4-yl)-1H-imidazol-4-yl,
2-(6-phenylpyrimidin-4-yl)-1H-imidazol-4-yl,
2-(6-phenylpyrazin-2-yl)-1H-imidazol-4-yl,
2-(2-quinolyl)-1H-imidazol-4-yl,
2-(3-quinolyl)-1H-imidazol-4-yl,
2-(3-isoquinolyl)-1H-imidazol-4-yl,
2-(3-biphenylyl)-1H-imidazol-4-yl,
2-(4-biphenylyl)-1H-imidazol-4-yl,
5-phenyl-1H-pyrazol-3-yl,
5-(2-fluorophenyl)-1H-pyrazol-3-yl,
5-(3-fluorophenyl)-1H-pyrazol-3-yl,
5-(4-fluorophenyl)-1H-pyrazol-3-yl,
5-(2,4-difluorophenyl)-1H-pyrazol-3-yl,
5-(2,5-difluorophenyl)-1H-pyrazol-3-yl,
5-(3,5-difluorophenyl)-1H-pyrazol-3-yl,
5-(2-chlorophenyl)-1H-pyrazol-3-yl,
5-(3-chlorophenyl)-1H-pyrazol-3-yl,
5-(3-bromophenyl)-1H-pyrazol-3-yl,
5-(4-bromophenyl)-1H-pyrazol-3-yl,
5-(2-trifluoromethylphenyl)-1H-pyrazol-3-yl,
5-(3-trifluoromethylphenyl)-1H-pyrazol-3-yl,
5-(4-trifluoromethylphenyl)-1H-pyrazol-3-yl, 5-(3-methoxyphenyl)-1H-pyrazol-3-yl,
5-(2-difluoromethoxyphenyl)-1H-pyrazol-3-yl,
5-(3-difluoromethoxyphenyl)-1H-pyrazol-3-yl,
5-(3-hydroxyphenyl)-1H-pyrazol-3-yl,
5-(4-hydroxyphenyl)-1H-pyrazol-3-yl,
5-(2-naphthyl)-1H-pyrazol-3-yl,
5-(1-phenylpyrazol-3-yl)-1H-pyrazol-3-yl,
5-(4-phenylpyrazol-4-yl)-1H-pyrazol-3-yl,
5-(4-phenylpyridin-2-yl)-1H-pyrazol-3-yl,
5-(6-phenylpyridin-2-yl)-1H-pyrazol-3-yl,
5-(5-phenylpyridin-3-yl)-1H-pyrazol-3-yl,
5-(2-phenylpyridin-4-yl)-1H-pyrazol-3-yl,
5-(6-fluoropyridin-2-yl)-1H-pyrazol-3-yl,
5-(2-fluoropyridin-5-yl)-1H-pyrazol-3-yl,
5-(5-fluoropyridin-2-yl)-1H-pyrazol-3-yl,
5-(2-phenylpyrimidin-4-yl)-1H-pyrazol-3-yl,
5-[2-(2-fluorophenyl)pyrimidin-4-yl]-1H-pyrazol-3-yl,
5-[2-(4-fluorophenyl)pyrimidin-4-yl]-1H-pyrazol-3-yl,
5-(6-phenylpyrimidin-4-yl)-1H-pyrazol-3-yl,
5-(6-phenylpyrazin-2-yl)-1H-pyrazol-3-yl,
5-(2-quinolyl)-1H-pyrazol-3-yl,
5-(3-quinolyl)-1H-pyrazol-3-yl,
5-(3-isoquinolyl)-1H-pyrazol-3-yl,
5-(3-biphenylyl)-1H-pyrazol-3-yl,
5-(4-biphenylyl)-1H-pyrazol-3-yl,
5-phenyl-1H-1,2,4-triazol-3-yl,
5-(2-fluorophenyl)-1H-1,2,4-triazol-3-yl,
5-(3-fluorophenyl)-1H-1,2,4-triazol-3-yl,
5-(4-fluorophenyl)-1H-1,2,4-triazol-3-yl,
5-(2,4-difluorophenyl)-1H-1,2,4-triazol-3-yl,
5-(2,5-difluorophenyl)-1H-1,2,4-triazol-3-yl,
5-(3,5-difluorophenyl)-1H-1,2,4-triazol-3-yl,
5-(2-chlorophenyl)-1H-1,2,4-triazol-3-yl,
5-(3-chlorophenyl)-1H-1,2,4-triazol-3-yl,
5-(3-bromophenyl)-1H-1,2,4-triazol-3-yl,
5-(4-bromophenyl)-1H-1,2,4-triazol-3-yl,
5-(2-trifluoromethylphenyl)-1H-1,2,4-triazol-3-yl,
5-(3-trifluoromethylphenyl)-1H-1,2,4-triazol-3-yl,
5-(4-trifluoromethylphenyl)-1H-1,2,4-triazol-3-yl,
5-(3-methoxyphenyl)-1H-1,2,4-triazol-3-yl,
5-(2-difluoromethoxyphenyl)-1H-1,2,4-triazol-3-yl,
5-(3-difluoromethoxyphenyl)-1H-1,2,4-triazol-3-yl,
5-(3-hydroxyphenyl)-1H-1,2,4-triazol-3-yl,
5-(4-hydroxyphenyl)-1H-1,2,4-triazol-3-yl,
5-(2-naphthyl)-1H-1,2,4-triazol-3-yl,
5-(1-phenylpyrazol-3-yl)-1H-1,2,4-triazol-3-yl,
5-(1-phenylpyrazol-4-yl)-1H-1,2,4-triazol-3-yl,
5-(4-phenylpyridin-2-yl)-1H-1,2,4-triazol-3-yl,
5-(6-phenylpyridin-2-yl)-1H-1,2,4-triazol-3-yl,
5-(5-phenylpyridin-3-yl)-1H-1,2,4-triazol-3-yl,
5-(2-phenylpyridin-4-yl)-1H-1,2,4-triazol-3-yl,
5-(6-fluoropyridin-2-yl)-1H-1,2,4-triazol-3-yl,
5-(2-fluoropyridin-5-yl)-1H-1,2,4-triazol-3-yl,
5-(5-fluoropyridin-2-yl)-1H-1,2,4-triazol-3-yl,
5-(2-phenylpyrimidin-4-yl)-1H-1,2,4-triazol-3-yl,
5-(6-phenylpyrimidin-4-yl)-1H-1,2,4-triazol-3-yl,
5-(6-phenylpyrazin-2-yl)-1H-1,2,4-triazol-3-yl,
5-(2-quinolyl)-1H-1,2,4-triazol-3-yl,
5-(3-quinolyl)-1H-1,2,4-triazol-3-yl,
5-(3-isoquinolyl)-1H-1,2,4-triazol-3-yl,
5-(3-biphenylyl)-1H-1,2,4-triazol-3-yl,
5-(4-biphenylyl)-1H-1,2,4-triazol-3-yl,
6-phenyl-1H-pyrazolo[2,3-b][1,2,4]triazol-2-yl,
6-(2-fluorophenyl)-1H-pyrazolo[2,3-b][1,2,4]triazol-2-yl,
6-(3-fluorophenyl)-1H-pyrazolo[2,3-b][1,2,4]triazol-2-yl,
6-(4-fluorophenyl)-1H-pyrazolo[2,3-b][1,2,4]triazol-2-yl,
6-(2,4-difluorophenyl)-1H-pyrazolo[2,3-b][1,2,4]triazol-2-yl,
6-(2,5-difluorophenyl)-1H-pyrazolo[2,3-b][1,2,4]triazol-2-yl,
6-(3,5-difluorophenyl)-1H-pyrazolo[2,3-b][1,2,4]triazol-2-yl,
6-(2-chlorophenyl)-1H-pyrazolo[2,3-b][1,2,4]triazol-2-yl,
6-(3-chlorophenyl)-1H-pyrazolo[2,3-b][1,2,4]triazol-2-yl,
6-(3-bromophenyl)-1H-pyrazolo[2,3-b][1,2,4]triazol-2-yl,
6-(4-bromophenyl)-1H-pyrazolo[2,3-b][1,2,4]triazol-2-yl,
6-(2-trifluoromethylphenyl)-1H-pyrazolo[2,3-b][1,2,4]triazol-2-yl,
6-(3-trifluoromethylphenyl)-1H-pyrazolo[2,3-b][1,2,4]triazol-2-yl,
6-(4-trifluoromethylphenyl)-1H-pyrazolo[2,3-b][1,2,4]triazol-2-yl,
6-(3-methoxyphenyl)-1H-pyrazolo[2,3-b][1,2,4]triazol-2-yl,
6-(2-difluoromethoxyphenyl)-1H-pyrazolo[2,3-b][1,2,4]triazol-2-yl,
6-(3-difluoromethoxyphenyl)-1H-pyrazolo[2,3-b][1,2,4]triazol-2-yl,
6-(3-hydroxyphenyl)-1H-pyrazolo[2,3-b][1,2,4]triazol-2-yl,
6-(4-hydroxyphenyl)-1H-pyrazolo[2,3-b][1,2,4]triazol-2-yl,
6-(6-fluoropyridin-2-yl)-1H-pyrazolo[2,3-b][1,2,4]triazol-2-yl,
6-(2-fluoropyridin-5-yl)-1H-pyrazolo[2,3-b][1,2,4]triazol-2-yl,
6-(5-fluoropyridin-2-yl)-1H-pyrazolo[2,3-b][1,2,4]triazol-2-yl,
5-phenyl-1H-imidazo[1,2-b][1,2,4]triazol-2-yl,
2-phenyl-2,4-dihydroimidazo[4,5-d][1,2,3]triazol-5-yl,
2-(2-fluorophenyl)-2,4-dihydroimidazo[4,5-d][1,2,3]triazol-5-yl,
2-(3-fluorophenyl)-2,4-dihydroimidazo[4,5-d][1,2,3]triazol-5-yl,
2-(4-fluorophenyl)-2,4-dihydroimidazo[4,5-d][1,2,3]triazol-5-yl,
2-(2,4-difluorophenyl)-2,4-dihydroimidazo[4,5-d][1,2,3]triazol-5-yl,
2-(2,5-difluorophenyl)-2,4-dihydroimidazo[4,5-d][1,2,3]triazol-5-yl,
2-(3,5-difluorophenyl)-2,4-dihydroimidazo[4,5-d][1,2,3]triazol-5-yl,
2-(2-chlorophenyl)-2,4-dihydroimidazo[(4,5-d][1,2,3]triazol-5-yl,
2-(3-chlorophenyl)-2,4-dihydroimidazo[4,5-d][1,2,3]triazol-5-yl,
2-(3-bromophenyl)-2,4-dihydroimidazo[4,5-d][1,2,3]triazol-5-yl,
2-(4-bromophenyl)-2,4-dihydroimidazo[4,5-d][1,2,3]triazol-5-yl,
2-(2-trifluoromethylphenyl)-2,4-dihydroimidazo[4,5-d][1,2,3]triazol-5-yl,
2-(3-trifluoromethylphenyl)-2,4-dihydroimidazo[4,5-d][1,2,3]triazol-5-yl,
2-(4-trifluoromethylphenyl)-2,4-dihydroimidazo[4,5-d][1.2.3]triazol-5-yl,
2-(3-methoxyphenyl)-2,4-dihydroimidazo[4,5-d][1,2,3]triazol-5-yl,
2-(2-difluoromethoxyphenyl)-2,4-dihydroimidazo[4,5-d][1,2,3]triazol-5-yl,
2-(3-difluoromethoxyphenyl)-2,4-dihydroimidazo[4,5-d][1,2,3]triazol-5-yl,
2-(3-hydroxyphenyl)-2,4-dihydroimidazo[4,5-d][1,2,3]triazol-5-yl, 2-(4-hydroxyphenyl)-2,4-dihydroimidazo[4,5-d][1,2,3]triazol-5-yl,
2-(6-fluoropyridin-2-yl)-2,4-dihydroimidazo[4,5-d][1,2,3]triazol-5-yl,
2-(2-fluoropyridin-5-yl)-2,4-dihydroimidazo[4,5-d][1,2,3]triazol-5-yl,
2-(5-fluoropyrdin-2-yl)-2,4-dihydroimidazo[4,5-d][1,2,3]triazol-5-yl,
2-phenyl-1H-imidazo[1,2-b]pyrazol-6-yl,
2-phenyl-2,4-dihydroimidazo[4,5-c]pyrazol-5-yl,
2-(2-fluorophenyl)-2,4-dihydroimidazo[4,5-c]pyrazol-5-yl,
2-(3-fluorophenyl)-2,4-dihydroimidazo[4,5-c]pyrazol-5-yl,
2-(4-fluorophenyl)-2,4-dihydroimidazo[4,5-c]pyrazol-5-yl,
2-(2,4-difluorophenyl)-2,4-dihydroimidazo[4,5-c]pyrazol-5-yl,
2-(2,5-difluorophenyl)-2,4-dihydroimidazo[4,5-c]pyrazol-5-yl,
2-(3,5-difluorophenyl)-2,4-dihydroimidazo[4,5-c]pyrazol-5-yl,
2-(2-chlorophenyl)-2,4-dihydroimidazo[4,5-c]pyrazol-5-yl,
2-(3-chlorophenyl)-2,4-dihydroimidazo[4,5-c]pyrazol-5-yl,
2-(3-bromophenyl)-2,4-dihydroimidazo[4,5-c]pyrazol-5-yl,
2-(4-bromophenyl)-2,4-dihydroimidazo[4,5-c]pyrazol-5-yl,
2-(2-trifluoromethylphenyl)-2,4-dihydroimidazo[4,5-c]pyrazol-5-yl,
2-(3-trifluoromethylphenyl)-2,4-dihydroimidazo[4,5-c]pyrazol-5-yl,
2-(4-trifluoromethylphenyl)-2,4-dihydroimidazo[4,5-c]pyrazol-5-yl,
2-(3-methoxyphenyl)-2,4-dihydroimidazo[4,5-c]pyrazol-5-yl,
2-(2-difluoromethoxyphenyl)-2,4-dihydroimidazo[4,5-c]pyrazol-5-yl,
2-(3-difluoromethoxyphenyl)-2,4-dihydroimidazo[4,5-c]pyrazol-5-yl,
2-(3-hydroxyphenyl)-2,4-dihydroimidazo[4,5-c]pyrazol-5-yl,
2-(4-hydroxyphenyl)-2,4-dihydroimidazo[4,5-c]pyrazol-5-yl,
2-(6-fluoropyridin-2-yl)-2,4-dihydroimidazo[4,5-c]pyrazol-5-yl,
2-(2-fluoropyridin-5-yl)-2,4-dihydroimidazo[4,5-c]pyrazol-5-yl,
2-(5-fluoropyridin-2-yl)-2,4-dihydroimidazo[4,5-c]pyrazol-5-yl,
6-phenyl-1H-[1,2,4]triazolo[2,3-b][1,2,4]triazol-2-yl, and the like Among those groups mentioned above, more preferable examples of Az are
4,5-diphenyl-1H-imidazol-2-yl,
4-methyl-5-phenyl-1H-imidazol-2-yl,
4-(3,5-difluorophenyl)-1H-imidazol-2-yl,
4-(3-chlorophenyl)-1H-imidazol-2-yl,
4-(3-bormophenyl)-1H-imidazol-2-yl,
4-(4-bormophenyl)-1H-imidazol-2-yl,
4-(3-trifluoromethylphenyl)-1H-imidazol-2-yl,
4-(3-methoxyphenyl)-1H-imidazol-2-yl,
4-(3-difluoromethoxyphenyl)-1H-imidazol-2-yl,
4-(2-naphthyl)-1H-imidazol-2-yl,
4-(1-phenylpyrazol-3-yl)-1H-imidazol-2-yl,
4-(2-phenylpyridin-4-yl)-1H-imidazol-2-yl,
4-(4-fluorophenyl)-5-(3-pyridyl)-1H-imidazol-2-yl,
4-(2-phenylpyrimidin-4-yl)-1H-imidazol-2-yl,
4-(6-phenylpyrazin-2-yl)-1H-imidazol-2-yl,
4-(2-quinolyl)-1H-imidazol-2-yl,
4-(3-quinolyl)-1H-imidazol-2-yl,
4-(3-isoquinolyl)-1H-imidazol-2-yl,
4-(3-biphenylyl)-1H-imidazol-2-yl,
4-(4-biphenylyl)-1H-imidazol-2-yl,
2-(3,5-difluorophenyl)-1H-imidazol-4-yl,
2-(3-chlorophenyl)-1H-imidazol-4-yl
2-(3-bromophenyl)-1H-imidazol-4-yl,
2-(4-bromophenyl)-1H-imidazol-4-yl,
2-(3-trifluoromethylphenyl)-1H-imidazol-4-yl,
2-(3-difluoromethoxyphenyl)-1H-imidazol-4-yl,
2-(2-naphthyl)-1H-imidazol-4-yl,
2-(1-phenylpyrazol-3-yl)-1H-imidazol-4-yl,
2-(2-phenylpyridin-4-yl)-1H-imidazol-4-yl,
2-(2-phenylpyrimidin-4-yl)-1H-imidazol-4-yl,
2-(6-phenylpyrazin-2-yl)-1H-imidazol-4-yl,
2-(2-quinolyl)-1H-imidazol-4-yl,
2-(3-quinolyl)-1H-imidazol-4-yl,
2-(3-isoquinolyl)-1H-imidazol-4-yl,
2-(3-biphenylyl)-1H-imidazol-4-yl,
5-(3,5-difluorophenyl)-1H-pyrazol-3-yl,
5-(3-chlorophenyl)-1H-pyrazol-3-yl,
5-(3-bromophenyl)-1H-pyrazol-3-yl,
5-(4-bromophenyl)-1H-pyrazol-3-yl,
5-(3-trifluoromethylphenyl)-1H-pyrazol-3-yl,
5-(3-difluoromethoxyphenyl)-1H-pyrazol-3-yl,
5-(2-naphthyl)-1H-pyrazol-3-yl,
5-(1-phenylpyrazol-3-yl)-1H-pyrazol-3-yl,
5-(2-phenylpyridin-4-yl)-1H-pyrazol-3-yl,
5-(2-phenylpyrimidin-4-yl)-1H-pyrazol-3-yl,
5-(6-phenylpyrazin-2-yl)-1H-pyrazol-3-yl,
5-(2-quinolyl)-1H-pyrazol-3-yl,
5-(3-quinolyl)-1H-pyrazol-3-yl,
5-(3-isoquinolyl)-1H-pyrazol-3-yl,
5-(3-biphenylyl)-1H-pyrazol-3-yl,
5-(3,5-difluorophenyl)-1H-1,2,4-triazol-3-yl,
5-(3-chlorophenyl)-1H-1,2,4-triazol-3-yl,
5-(3-bromophenyl)-1H-1,2,4-triazol-3-yl,
5-(4-bromophenyl)-1H-1,2,4-triazol-3-yl,
5-(3-trifluoromethylphenyl)-1H-1,2,4-triazol-3-yl,
5-(3-difluoromethoxyphenyl)-1H-1,2,4-triazol-3-yl,
5-(2-naphthyl)-1H-1,2,4-triazol-3-yl,
5-(1-phenylpyrazol-3-yl)-1H-1,2,4-triazol-3-yl,
5-(2-phenylpyridin-4-yl)-1H-1,2,4-triazol-3-yl,
5-(2-phenylpyrimidin-4-yl)-1H-1,2,4-triazol-3-yl,
5-(6-phenylpyrazin-2-yl)-1H-1,2,4-triazol-3-yl,
5-(2-quinolyl)-1H-1,2,4-triazol-3-yl,
5-(3-quinolyl)-1H-1,2,4-triazol-3-yl,
5-(3-isoquinolyl)-1H-1,2,4-triazol-3-yl,
5-(3-biphenylyl)-1H-1,2,4-triazol-3-yl,
6-phenyl-1H-pyrazolo[2,3-b][1,2,4]triazol-2-yl,
6-(2-fluorophenyl)-1H-pyrazolo[2,3-b][1,2,4]triazol-2-yl,
6-(3-fluorophenyl)-1H-pyrazolo[2,3-b][1,2,4]triazol-2-yl,
6-(4-fluorophenyl)-1H-pyrazolo[2,3-b][1,2,4]triazol-2-yl,
5-phenyl-1H-imidazo[1,2-b][1,2,4]triazol-2-yl,
2-phenyl-2,4-dihydroimidazo[4,5-d][1,2,3]triazol-5-yl,
2-(2-fluorophenyl)-2,4-dihydroimidazo[4,5-d][1,2,3]triazol-5-yl,
2-(3-fluorophenyl)-2,4-dihydroimidazo[4,5-d][1,2,3]triazol-5-yl,
2-(4-fluorophenyl)-2,4-dihydroimidazo[4,5-d][1,2,3]triazol-5-yl,
2-phenyl-1H-imidazo[1,2-b]pyrazol-6-yl,
2-phenyl-2,4-dihydroimidazo[4,5-c]pyrazol-5-yl,
2-(2-fluorophenyl)-2,4-dihydroimidazo[4,5-c]pyrazol-5-yl,
2-(3-fluorophenyl)-2,4-dihydroimidazo[4,5-c]pyrazol-5-yl,
2-(4-fluorophenyl)-2,4-dihydroimidazo[4,5-c]pyrazol-5-yl,
6-phenyl-1H-[1,2,4]triazolo[2,3-b][1,2,4]triazol-2-yl and the like, and especially preferred are
4-(3-trifluoromethylphenyl)-1H-imidazol-2-yl, 4-(2-naphthyl)-1H-imidazol-2-yl,
4-(3-biphenylyl)-1H-imidazol-2-yl,
2-(3-trifluoromethylphenyl)-1H-imidazol-4-yl,
2-(2-naphthyl)-1H-imidazol-4-yl,
2-(3-biphenylyl)-1H-imidazol-4-yl,
5-(3,5-difluorophenyl)-1H-pyrazol-3-yl,
5-(3-chlorophenyl)-1H-pyrazol-3-yl,
5-(3-bromophenyl)-1H-pyrazol-3-yl,
3-(4-bromophenyl)-1H-pyrazol-3-yl,
5-(3-trifluoromethylphenyl)-1H-pyrazol-3-yl,
5-(3-difluoromethoxyphenyl)-1H-pyrazol-3-yl,
5-(2-naphthyl)-1H-pyrazol-3-yl,
5-(1-phenylpyrazol-3-yl)-1H-pyrazol-3-yl,
5-(2-phenylpyridin-4-yl)-1H-pyrazol-3-yl,
5-(2-phenylpyrimidin-4-yl)-1H-pyrazol-3-yl,
5-[2-(2-fluorophenyl)pyrimidin-4-yl]-1H-pyrazol-3-yl,
5-[2-(4-fluorophenyl)pyrimidin-4-yl]-1H-pyrazol-3-yl,
5-(6-phenylpyrazin-2-yl)-1H-pyrazol-3-yl,
5-(2-quinolyl)-1H-pyrazol-3-yl,
5-(3-quinolyl)-1H-pyrazol-3-yl,
5-(3-isoquinolyl)-1H-pyrazol-3-yl,
5-(3-biphenylyl)-1H-pyrazol-3-yl,
5-(3-trifluoromethylphenyl)-1H-1,2,4-triazol-3-yl,
5-(2-naphthyl)-1H-1,2,4-triazol-3-yl,
5-(3-biphenylyl)-1H-1,2,4-triazol-3-yl,
6-phenyl-1H-pyrazolo[2,3-b][1,2,4]triazol-2-yl,
6-(2-fluorophenyl)-1H-pyrazolo[2,3-b][1,2,4]triazol-2-yl,
6-(3-fluorophenyl)-1H-pyrazolo[2,3-b][1,2,4]triazol-2-yl,
6-(4-fluorophenyl)-1H-pyrazolo[2,3-b][1,2,4]triazol-2-yl,
2-phenyl-2,4-dihydroimidazo[4,5-d][1,2,3]triazol-5-yl,
2-phenyl-2,4-dihydroimidazo[4,5-c]pyrazol-5-yl, and the like.

X is nitrogen atom or methine.

T, U, V and W are independently methine or nitrogen atom, said methine being optionally substituted by a substituent selected from the group consisting of halogen, lower alkyl, halo-lower alkyl, hydroxy, lower alkoxy and halo-lower alkoxy, and at least two of T, U, V and W are said methine groups.

"Methine which is optionally substituted by a substituent selected from the group consisting of halogen, lower alkyl, halo-lower alkyl, hydroxy, lower alkoxy and halo-lower alkoxy" refers to an unsubstituted methine group or a methine group having a substituent selected from the group consisting of halogen, lower alkyl, halo-lower alkyl, hydroxy, lower alkoxy and halo-lower alkoxy.

Halogen as said substituent preferably includes, for example, fluorine, chlorine and the like.

Lower alkyl as said substituent preferably includes, for example, methyl, ethyl and the like.

Halo-lower alkyl as said substituent preferably includes, for example, difluoromethyl, trifluoromethyl and the like.

Lower alkoxy as said substituent preferably includes, for example, methoxy, ethoxy and the like.

Halo-lower alkoxy as said substituent preferably includes, for example, fluoromethoxy, difluoromethoxy, trifluoromethoxy and the like.

Said substituent includes, for example, halogen, lower alkyl, hydroxy, lower alkoxy and the like, and preferably halogen and the like.

The preferred embodiment of T, U, V and W includes the case where T, U, V and W are independently a methine group optionally having a substituent selected from halogen, lower alkyl, hydroxy, and lower alkoxy, and preferably halogen, or more preferably the case where they are an unsubstituted methine group; or the case where at least one of T, U, V and W is nitrogen.

Further, in the formula (I), a group represented by the formula (c):

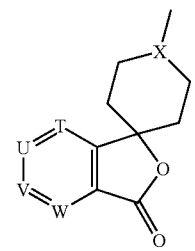

(wherein T, U, V, W and X have each the same meaning as defined above) includes, for example, groups represented by the following formula ($c_1$):

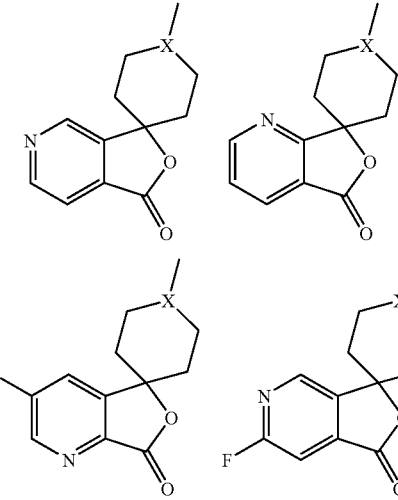

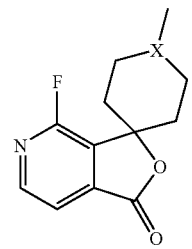

(wherein X has the same meaning as defined above), preferably groups represented by the following formula ($C_2$):

(c2)

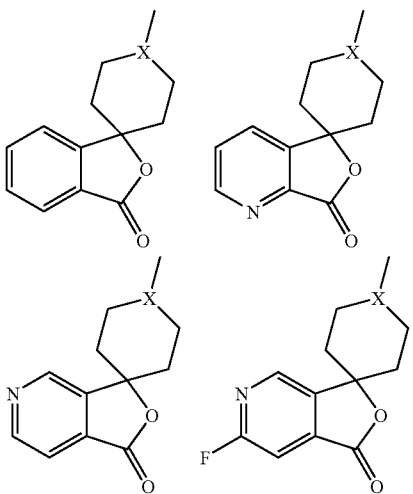

and the like.

The compounds of the present invention may include stereoisomers such as optical isomers, diastereoisomers and geometrical isomers, or tautomers depending upon the mode of substituents. The compounds of the present invention include all the stereoisomers, tautomers and their mixtures.

For example, compounds of the formula (I) wherein X is methine include stereoisomers such as a trans-form compound of the formula (I-1):

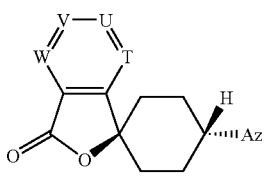
(I-1)

(wherein Az, T, U, V and W have each the same meaning as defined above) and a cis-form compound of the formula (I-2):

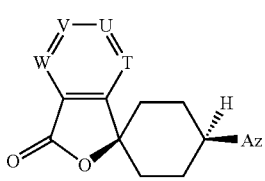
(I-2)

(wherein Az, T, U, V and W have each the same meaning as defined above), and trans-form compounds are preferable.

Also included within the scope of the invention are polymorphs, hydrates and solvates of the compounds of the present invention.

The present, invention also includes prodrugs of the compounds of this invention within its scope. In general, such prodrugs are functional derivatives of the compounds of the present invention which can be readily converted in vivo into the required compound. Thus, in the treatment methods for various diseases according to the present invention, the term "administering" shall encompass not only administration of the compound specified in this disclosure but also administration of a compound which is converted in vivo into the specified compound when administered to a patient. Conventional procedures for selection and preparation of suitable prodrug derivatives are described, for example, in "Design of Prodrugs," ed. H. Bundgaard, Elsevier (1985), which are entirely incorporated by reference in this specification. Metabolites of these compounds include active compounds produced upon introduction of compounds of the present invention into the biological milieu, and are encompassed in the scope of the present invention.

Specific compounds of the formula (I) preferably include, for example, 4-(2-naphthyl)-2-[3-oxospiro[isobenzofuran-1(3H),4'-piperidin]-1'-yl]-1H-imidazole,
4-(4-bromophenyl)-2-[3-oxospiro[isobenzofuran-1(3H),4'-piperidin]-1'-yl]-1H-imidazole,
2-[3-oxospiro[isobenzofuran-1(3H),4'-piperidin]-1'-yl]-4-(3-trifluoromethylphenyl)-1H-imidazole,
4-(4-biphenylyl)-2-[3-oxospiro[isobenzofuran-1(3H),4'-piperidin]-1'-yl]-1H-imidazole,
4-(3-biphenylyl)-2-[3-oxospiro[isobenzofuran-1(3H),4'-piperidin]-1'-yl]-1H-imidazole,
2-[3-oxospiro[isobenzofuran-1(3H),4'-piperidin]-1'-yl]-4,5-diphenyl-1H-imidazole,
4-(4-fluorophenyl)-5-(3-pyridyl)-2-[3-oxospiro[isobenzofuran-1(3H),4'-piperidin]-1'-yl]-1H-imidazole,
4-methyl-2-[3-oxospiro[isobenzofuran-1(3H),4'-piperidin]-1'-yl]-5-phenyl-1H-imidazole,
4-(3-methoxyphenyl)-2-[3-oxospiro[isobenzofuran-1(3H),4'-piperidin]-1'-yl]-1H-imidazole,
trans-4-(2-naphthyl)-2-[3'-oxospiro[cyclohexane-1,1'(3'H)-isobenzofuran]-4-yl]-1H-imidazole,
trans-2-[3'-oxospiro[cyclohexane-1,1'(3'H)-isobenzofuran]-4-yl]-4-(3-trifluoromethylphenyl)-1H-imidazole,
trans-2-(2-naphthyl)-4-[3-oxospiro[6-azaisobenzofuran-1(3H),1-cyclohexan]-4'-yl]-1H-imidazole,
3-[3-oxospiro[isobenzofuran-1(3H),4'-piperidin]-1'-yl]-5-(3-trifluoromethylphenyl)-1H-pyrazole,
3-[3-oxospiro[isobenzofuran-1(3H),4'-piperidin]-1'-yl]-5-(2-phenylpyridin-4-yl)-1H-pyrazole,
3-(3-biphenylyl)-5-[3-oxospiro[isobenzofuran-1(3H),4'-piperidin]-1'-yl]-1H-pyrazole,
3-(3-bromophenyl)-5-[3-oxospiro[isobenzofuran-1(3H),4'-piperidin]-1'-yl]-1H-pyrazole,
3-(3-biphenylyl)-5-[3-oxospiro[6-azaisobenzofuran-1(3H),4'-piperidin]-1'-yl]-1H-pyrazole,
3-[3-oxospiro[6-azaisobenzofuran-1(3H),4'-piperidin]-1'-yl]-5-(2-phenylpyridine-4-yl)-1H-pyrazole,
3-[3-oxospiro[isobenzofuran-1(3H),4'-piperidin]-1'-yl]-5-(2-phenylpyrimidin-4-yl)-1H-pyrazole,
trans-3-(3-biphenylyl)-5-[3'-oxospiro[cyclohexane-1,1'(3'H)-isobenzofuran-4-yl]-1H-pyrazole,
trans-3-[3'-oxospiro[cyclohexane-1,1'(3'H)-isobenzofuran]-4-yl]-5-(2-phenylpyridin-4-yl)-1H-pyrazole,
trans-3-[3'-oxospiro[cyclohexane-1,1'(3'H)-isobenzofuran]-4-yl]-5-(1-phenylpyrazol-3-yl)-1H-pyrazole,
trans-3-[3'-oxospiro[cyclohexane-1,1'(3'H)-isobenzofuran]-4-yl]-5-(2-phenylpyrimidin-4-yl)-1H-pyrazole,
trans-3-[3'-oxospiro[cyclohexane-1,1'(3'H)-isobenzofuran]-4-yl]-5-(6-phenylpyrazin-2-yl)-1H-pyrazole,
trans-3-(3-chlorophenyl)-5-[3'-oxospiro[cyclohexane-1,1'(3'H)-isobenzofuran]-4-yl]-1H-pyrazole,
trans-3-[3'-oxospiro[cyclohexane-1,1'(3'H)-isobenzofuran]-4-yl]-5-(2-quinolyl)-1H-pyrazole, trans-3-(3-biphenylyl)-5-[3-oxospiro[6-azaisobenzofuran-1 (3H),1'-cyclohexan]-4'-yl]-1H-pyrazole,
trans-3-(3-biphenylyl)-5-[3-oxospiro[5-azaisobenzofuran-1 (3H),1'-cyclohexan]-4'-yl]-1H-pyrazole,
trans-3-[3-oxospiro[6-azaisobenzofuran-1(3H),1'-cyclohexan]-4'-yl]-5-(2-phenylpyrimidin-4-yl)-1H-pyrazole,
3-(2-naphthyl)-5-[3-oxospiro[isobenzofuran-1(3H),4'-piperidin]-1'-yl]-1H-1,2,4-triazole,
3-[3-oxospiro[isobenzofuran-1(3H),4'-piperidin]-1'-yl]-5-(3-trifluoromethylphenyl)-1H-1,2,4-triazole,
trans-6-(4-fluorophenyl)-2-[3-oxospiro[6-azaisobenzofuran-1(3H),1'-cyclohexan]-4'-yl]-1H-pyrazolo[2,3-b][1,2,4]triazole,
cis-6-(4-fluorophenyl)-2-[3-oxospiro[6-azaisobenzofuran-1 (3H),1'-cyclohexan]-4'-yl]-1H-pyrazolo[2,3-b][1,2,4]triazole,
trans-6-(3-fluorophenyl)-2-[3-oxospiro[6-azaisobenzofuran-1(3H),1'-cyclohexan]-4'-yl]-1H-pyrazolo[2,3-b][1,2,4]triazole,
cis-6-(3-fluorophenyl)-2-[3-oxospiro[6-azaisobenzofuran-1 (3H),1'-cyclohexan]-4'-yl]-1H-pyrazolo[2,3-b][1,2,4]triazole,
trans-6-(2-fluorophenyl)-2-[3-oxospiro[6-azaisobenzofuran-1(3H),1'-cyclohexan]-4'-yl]-1H-pyrazolo[2,3-b][1,2,4]triazole,
trans-2-[3-oxospiro[6-azaisobenzofuran-1(3H),1'-cyclohexan]-4'-yl]-6-phenyl-1H-pyrazolo[2,3-b][1,2,4]triazole,
trans-2-[3'-oxospiro[cyclohexane-1,1'(3'H)-isobenzofuran]-4-yl]-6-phenyl-1H-pyrazolo[2,3-b][1,2,4]triazole,
cis-2-[3'-oxospiro[cyclohexane-1,1'(3'H)-isobenzofuran]-4-yl]-6-phenyl-1H-pyrazolo[2,3-b][1,2,4]triazole,
trans-2-[3'-oxospiro[cyclohexane-1,1'(3'H)-isobenzofuran]-4-yl]-5-phenyl-1H-imidazo[1,2-b][1,2,4]triazole,
trans-2-[3'-oxospiro[cyclohexane-1,1'(3'H)-isobenzofuran]-4-yl]-6-phenyl-1H-[1,2,4]triazolo[2,3-b][1,2,4]triazole,
trans-5-[3'-oxospiro[cyclohexane-1,1'(3'H)-isobenzofuran]-4-yl]-2-phenyl-2,4-dihydroimidazo[4,5-d][1,2,3]triazole,
trans-2-(2-fluorophenyl)-5-[3'-oxospiro[cyclohexane-1,1' (3'H)-isobenzofuran]-4-yl]-2,4-dihydroimidazo[4,5-d][1,2,3]triazole,
trans-2-(4-fluorophenyl)-5-[3'-oxospiro[cyclohexane-1,1' (3'H)-isobenzofuran]-4-yl]-2,4-dihydroimidazo[4,5-d][1,2,3]triazole,
trans-5-[3-oxospiro[6-azaisobenzofuran-1(3H),1'-cyclohexan]-4'-yl]-2-phenyl-2,4-dihydroimidazo[4,5-c]pyrazole,
trans-6-[3-oxospiro[6-azaisobenzofuran-1(3H),1'-cyclohexan]-4'-yl]-2-phenyl-1H-imidazo[1,2-b]pyrazole,
3-[3-oxospiro[6-azaisobenzofuran-1(3H),4'-piperidin-1'-yl]-5-(2-phenylpyrimidin-4-yl)-1H-pyrazole,
3-[3-oxospiro[6-azaisobenzofuran-1(3H),4'-piperidin-1'-yl]-5-[2-(2-fluorophenyl)pyrimidin-4-yl]-1H-pyrazole, or
3-[3-oxospiro[6-azaisobenzofuran-1(3H),4'-piperidin]-1'-yl]-5-[2-(4-fluorophenyl)pyrimidin-4-yl]-1H-pyrazole.

Among those compounds, preferred are
4-(2-naphthyl)-2-[3-oxospiro[isobenzofuran-1(3H),4'-piperidin]-1'-yl]-1H-imidazole,
3-[3-oxospiro[isobenzofuran-1(3H),4'-piperidin]-1'-yl]-5-(2-phenylpyridin-4-yl)-1H-pyrazole,
3-[3-oxospiro[isobenzofuran-1(3H),4-piperidin]-1'-yl]-5-(2-phenylpyrimidin-4-yl)-1H-pyrazole,
trans-3-[3'-oxospiro[cyclohexane-1,1'(3'H)-isobenzofuran]-4-yl]-5-(2-phenylpyrimidin-4-yl)-1H-pyrazole,
trans-3-[3'-oxospiro[cyclohexane-1,1'(3'H)-isobenzofuran]-4-yl]-5-(6-phenylpyrazin-2-yl)-1H-pyrazole,
trans-3-[3-oxospiro[6-azaisobenzofuran-1(3H),1'-cyclohexan]-4'-yl]-5-(2-phenylpyrimidin-4-yl)-1H-pyrazole,
3-(2-naphthyl)-5-[3-oxospiro[isobenzofuran-1(3H),4'-piperidin]-1'-yl]-1H-1,2,4-triazole,
trans-6-(2-fluorophenyl)-2-[3-oxospiro[6-azaisobenzofuran-1(3H),1'-cyclohexan]-4'-yl]-1H-pyrazolo[2,3-b][1,2,4]triazole,
trans-2-[3-oxospiro[6-azaisobenzofuran-1(3H),1'-cyclohexan]-4'-yl]-6-phenyl-1H-pyrazolo[2,3-b][1,2,4]triazole,
trans-2-[3'-oxospiro[cyclohexane-1,1'(3'H)-isobenzofuran]-4-yl]-6-phenyl-1H-pyrazolo[2,3-b][1,2,4]triazole,
3-[3-oxospiro[6-azaisobenzofuran-1(3H),4'-piperidin-1'-yl]-5-(2-phenylpyrimidin-4-yl)-1H-pyrazole,
3-[3-oxospiro[6-azaisobenzofuran-1(3H),4'-piperidin-1'-yl]-5-[2-(2-fluorophenyl)pyrimidin-4-yl]-1H-pyrazole,
3-[3-oxospiro[6-azaisobenzofuran-1(3H),4'-piperidin]-1'-yl]-5-[2-(4-fluorophenyl)pyrimidin-4-yl]-1H-pyrazole, and the like.

The process for producing compounds of the present invention is illustrated as follows.

Compounds (I) of the present invention can be prepared, for example, by the following Production Processes or the processes shown in Examples, but these embodiments are not intended to restrict the process for producing compounds (I) of this invention.

Production Process 1

A compound of the formula (I-1):

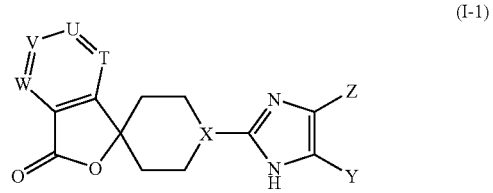

(I-1)

(wherein Z is hydrogen atom, halogen, cyano, lower alkyl, halo-lower alkyl, hydroxy, lower alkoxy, halo-lower alkoxy, lower alkoxycarbonyl, lower alkylsulfonyl, lower alkylsulfonyloxy, —N(R$^1$)R$^2$ or -Q$^1$-Ar$^1$; and Ar$^1$, Q$^1$, R$^1$, R$^2$, T, U, V, W, X and Y have the same meaning as defined above), can be prepared by reacting a compound of the formula (II):

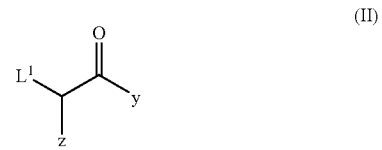

(II)

(wherein L$^1$ is a leaving group;

y and z are independently hydrogen atom, halogen, cyano, lower alkyl, halo-lower alkyl, lower alkoxy, halo-lower alkoxy, lower alkoxycarbonyl, lower alkylsulfonyl, lower alkylsulfonyloxy, —N(R$^{1P}$)R$^{2P}$, -Q$^{1P}$-Ar$^{1P}$ or optionally protected hydroxy;

Ar$^{1P}$ is aryl or heteroaryl, any of which is optionally substituted by a substituent selected from the group consisting of halogen, nitro, lower alkyl, halo-lower alkyl, cyclo-lower alkyl, lower alkenyl, lower alkoxy, halo-lower alkoxy, lower alkylthio, lower alkylsulfonyl, lower alkanoyl, lower alkoxycarbonyl, lower alkanoylamino, -Q²ᴾ-Ar²ᴾ, optionally protected oxo, optionally protected hydroxy, optionally protected hydroxy-lower alkyl and optionally protected carboxyl;

Ar²ᴾ is aryl or heteroaryl, any of which is optionally substituted by a substituent selected from the group consisting of halogen, cyano, lower alkyl, halo-lower alkyl, lower alkoxy, halo-lower alkoxy, di-lower alkylamino, lower alkanoyl, aryl, optionally protected hydroxy-lower alkyl, optionally protected hydroxy and optionally protected lower alkylamino;

Q¹ᴾ and Q²ᴾ are independently a single bond, oxygen atom, optionally protected carbonyl or —N(R³)—;

R¹ᴾ and R²ᴾ are independently an amino-protecting group, an imino-protecting group, hydrogen atom or lower alkyl, or R¹ᵖ and R²ᵖ, taken together, form lower alkylene which may be interrupted by oxygen atom, sulfur atom or optionally protected imino; and R³ is hydrogen atom or lower alkyl)

with a compound of the formula (III):

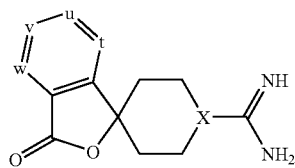

(III)

(wherein t, u, v and w are independently methine or nitrogen atom, said methine being optionally substituted by a substituent selected from the group consisting of halogen, lower alkyl, halo-lower alkyl, lower alkoxy, halo-lower alkoxy and optionally protected hydroxy, and at least two of t, u, v and w are said methine groups; and X is nitrogen atom or methine) or its salt to give a compound of the formula (IV):

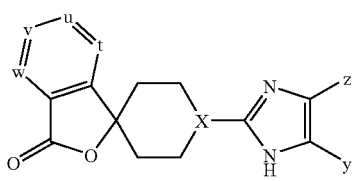

(IV)

(wherein t, u, v, w, X, y and z have each the same meaning as defined above), and optionally removing the protecting group(s) therefrom.

The present process refers to a process for preparing a compound of the formula (I) wherein Az is an optionally substituted 2-imidazolyl group, namely a compound of the formula (I-1).

The leaving groups represented by L¹ include, for example, halogen (e.g. chlorine, bromine, iodine), organic sulfonyl (e.g. methanesulfonyl, ethanesulfonyl, benzenesulfonyl), organic sulfonyloxy (e.g. methanesulfonyloxy, trifluoromethanesulfonyloxy, p-toluenesulfonyloxy) and the like.

In the above reaction, when a reactant has an amino, imino, hydroxy, carboxyl, oxo, carbonyl or the like which does not participate in the reaction, the reaction may be carried out after protecting the amino, imino, hydroxy, carboxyl, oxo, or carbonyl with an amino- or imino-protecting group, a hydroxy-protecting group, a carboxyl-protecting group, an oxo-protecting group or a carbonyl-protecting group, followed by deprotection after completion of the reaction.

The "amino- or imino-protecting group" is not particularly restricted, so long as it has such protective function. There are employed, for example, aralkyl (e.g. benzyl, p-methoxybenzyl, 3,4-dimethoxybenzyl, o-nitrobenzyl, p-nitrobenzyl, benzhydryl, trityl); lower alkanoyl (e.g. formyl, acetyl, propionyl, butyryl, pivaloyl); benzoyl; arylalkanoyl (e.g. phenylacetyl, phenoxyacetyl); lower alkoxycarbonyl(e.g. methoxycarbonyl, ethoxycarbonyl, propyloxycarbonyl, tert-butoxycarbonyl); aralkyloxycarbonyl (e.g. benzyloxycarbonyl, p-nitrobenzyloxycarbonyl, phenethyloxycarbonyl); lower alkylsilyl (e.g. trimethylsilyl, tert-butyldimethylsilyl); tetrahydropyranyl; trimethylsilylethoxymethyl; lower alkylsulfonyl (e.g. methylsulfonyl, ethylsulfonyl); arylsulfonyl (e.g. benzenesulfonyl, toluenesulfonyl) and the like, among which particularly preferred are acetyl, benzoyl, tert-butoxycarbonyl, trimethylsilylethoxymethyl, methylsulfonyl and the like.

The "hydroxy-protecting group" is not particularly restricted, so long as it has such protective function for hydroxy groups. There are employed, for example, lower alkyl (e.g. methyl, ethyl, propyl, isopropyl, tert-butyl); lower alkylsilyl (e.g. trimethylsilyl, tert-butyldimethylsilyl); lower alkoxymethyl (e.g. methoxymethyl, 2-methoxyethoxymethyl); tetrahydropyranyl; trimethylsilylethoxymethyl; aralkyl (e.g. benzyl, p-methoxybenzyl, 2,3-dimethoxybenzyl, o-nitrobenzyl, p-nitrobenzyl, trityl); and acyl (e.g. formyl, acetyl), among which particularly preferred are methyl, methoxymethyl, tetrahydropyranyl, trityl, trimethylsilylethoxymethyl, tert-butyldimethylsilyl, acetyl and the like.

The "carboxyl-protecting group" is not particularly; restricted, so long as it has such protective function for carboxyl groups. There are employed, for example, lower alkyl (e.g. methyl, ethyl, propyl, isopropyl, tert-butyl); halo-lower alkyl (e.g. 2,2,2-trichloroethyl); lower alkenyl (e.g. 2-propenyl); aralkyl (e.g. benzyl, p-methoxybenzyl, p-nitrobenzyl, benzhydryl, trityl) and the like, among which particularly preferred are methyl, ethyl, tert-butyl, 2-propenyl, benzyl, p-methoxybenzyl, benzhydryl and the like.

The "oxo- or carbonyl-protecting group" is not particularly limited, so long as it has such protective function for oxo or carbonyl groups. There are employed, for example, acetals or ketals, such as ethylene ketal, trimethylene ketal, and dimethyl ketal and the like.

The reaction between a compound of the formula (II) and a compound of the formula (III) is usually carried out by employing 0.5 moles to excessive moles, preferably an equivalent to 1.5 moles, of compound (III) relative to 1 mole of compound (II).

The reaction is usually carried out in an inert solvent. Preferable examples of such solvent are methylene chloride, chloroform, tetrahydrofuran, dioxane, dimethylformamide, N-methylpyrrolidone, dimethyl sulfoxide and the like, or a mixture thereof and the like.

The reaction is preferably carried out in the presence of, a base such as organic bases (e.g. triethylamine, diisopropylethylamine, pyridine, 4-dimethylaminopyridine), inorganic bases (e.g. sodium hydrogen carbonate, sodium carbonate, potassium carbonate, cesium carbonate, sodium hydroxide, potassium hydroxide) and the like.

The base is used in equimolar amount or in excess moles, preferably 1 to 5 moles, relative to 1 mole of the compound of the formula (II).

The reaction temperature is usually from 0° C. to 200° C., preferably 20° C. to 150° C.

The reaction time is usually 5 minutes to 7 days, preferably 30 minutes to 24 hours.

A usual treatment is carried out after completion of the reaction to obtain a crude product of a compound of the formula (IV). The resulting compound of the formula (IV) is, with or without purification according to the common method, subjected to optional removal of the protecting group for the amino, hydroxy, carboxyl, oxo carbonyl or the like, thereby to produce a compound of the formula (I-1).

Although the method for the removal of said protecting groups depends upon the kind of the protecting groups, the stability of a desired compound (I-1) and the like, it is carried out by, for example, a solvolysis using an acid or a base, that is, a method wherein for example 0.01 mole to a large excess of acid, preferably trifluoroacetic acid, formic acid, hydrochloric acid and the like, or an equivalent mole to a large excess of base, preferably potassium hydroxide, calcium hydroxide and the like is acted; a chemical reduction using a metal hydride complex; or a catalytic reduction using a palladium-carbon catalyst, a Raney-nickel catalyst, etc.; and the like, according to, for example, a method described in the literature (Protective Groups in Organic Synthesis, T. W. Greene, John Wiley & Sons, (1981)) or its similar method.

Production Process 2

A compound of the formula (I-2):

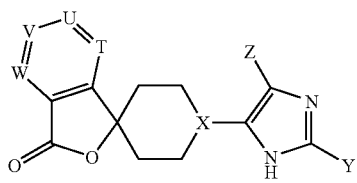
(I-2)

(wherein T, U, V, W, X, Y and Z are the same meaning as defined above), can be prepared by reacting a compound of the formula (V):

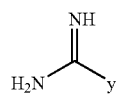
(V)

(wherein y is the same meaning as defined above) or its salt, with a compound of the formula (VI):

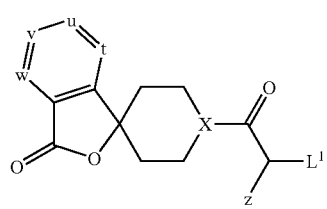
(VI)

(wherein $L^1$, t, u, v, w, X and z are the same meaning as defined above) or its salt to give a compound of the formula (VII):

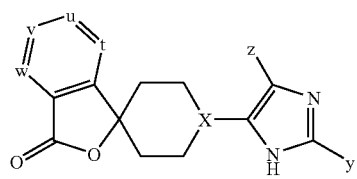
(VII)

(wherein t, u, v, w, X, y and z have each the same meaning as defined above), and optionally removing the protecting group(s) therefrom.

The present process refers to a process for preparing a compound of the formula (I) wherein Az is an optionally substituted 4-imidazolyl group, namely a compound of the formula (I-2).

The reaction between a compound of the formula (V) and a compound of the formula (VI) is usually carried out by employing 0.5 moles to excessive moles, preferably 1 to 1.5 moles of the compound (VI), relative to 1 mole of a compound of the formula (V).

The reaction is usually carried out in an inert solvent. Preferable examples of such solvent are methylene chloride, chloroform, tetrahydrofuran, dioxane, dimethylformamide, N-methylpyrrolidone, dimethyl sulfoxide, and a mixture thereof and the like.

The reaction is preferably carried out in the presence of a base such as organic bases (e.g. triethylamine, diisopropylethylamine, pyridine, 4-dimethylaminopyridine), inorganic bases (e.g. sodium hydrogen carbonate, sodium carbonate, potassium carbonate, cesium carbonate, sodium hydroxide, potassium hydroxide) and the like.

The base is used in equimolar amount or in excess moles, preferably 1 to 5 moles, relative to 1 mole of the compound of the formula (VI).

The reaction temperature is usually from 0° C. to 200° C., preferably 20° C. to 150° C.

The reaction time is usually 5-minutes to 7 days, preferably 5 minutes to 24 hours.

A compound of the formula (I-2) can be produced by treating a reaction mixture in the usual way after removal of the said protecting group(s) when the product has a protecting group after completion of the reaction, or by treating the mixture directly in the usual way when the protecting group is absent.

The deprotection and post-treatment may be carried out according to a method similar to the method described in Production Process 1.

Production Process 3

A compound of the formula (I-3):

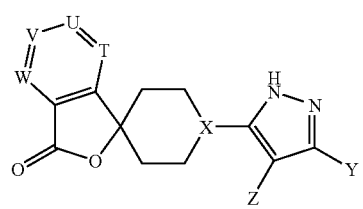
(I-3)

(wherein T, U, V, W, X, Y and Z are the same meaning as defined above), can be prepared by subjecting a compound of the formula (VIII):

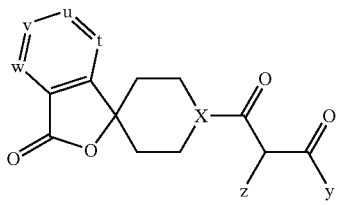

(VIII)

(wherein t, U, v, w, X, y and z are the same meaning as defined above) and hydrazine to dehydrative ring closure to give a compound of the formula (IX):

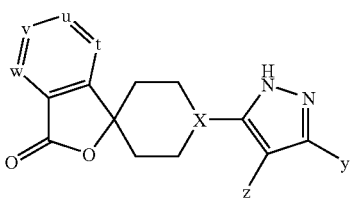

(IX)

(wherein t, u, v, w, X, y and z have each the same meaning as defined above), and optionally removing the protective group(s) therefrom.

The present process refers to a process for preparing a compound of the formula (I) wherein Az is an optionally substituted 3-pyrazolyl group, namely a compound of the formula (I-3).

The reaction between a compound of the formula (VIII) and hydrazine is usually carried out by employing 0.5 to excess moles, preferably 1.0 to 1.5 moles of hydrazine, relative to 1 mole of a compound of the formula (VIII).

The reaction is usually carried out in the presence of an inert solvent. Preferred examples of the inert solvent are ethanol, propanol, butanol, pentanol, 1,4-dioxane, dimethoxyethane, dimethylformamide, dimethyl sulfoxide, benzene, toluene, xylene, and a mixture thereof and the like.

The reaction temperature is usually from 0° C. to 200° C., preferably 20° C. to 150° C.

The reaction time is usually from 5 minutes to 7 days, preferably from 30 minutes to 24 hours.

A compound of the formula (I-3) can be produced by optionally deprotecting the protecting group(s) for the amino, hydroxyl, carboxyl, oxo and carbonyl groups from the resulting compound of the formula (IX) in the usual way using appropriate combination of deprotection methods with or without purification.

The removal of the protecting group(s), and the post-treatment may be conducted according to a method similar to the method described in the above Production Process 1.

Production Process 4

A compound of the formula (I-4):

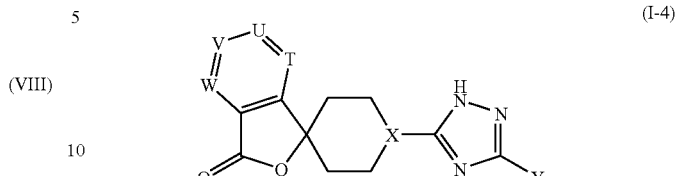

(I-4)

(wherein T, U, V, W, X and Y are the same meaning as defined above), can be prepared by reacting a compound of the formula (X):

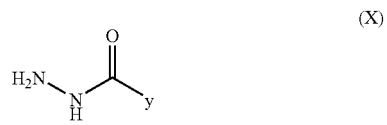

(X)

(wherein y is the same meaning as defined above) or its salt, with a compound of the formula (XI):

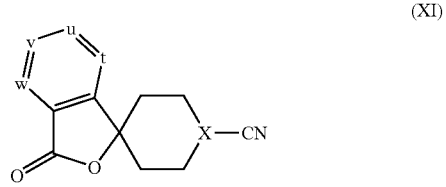

(XI)

(wherein t, u, v, w and X are the same meaning as defined above), or its salt to give a compound of the formula (XII):

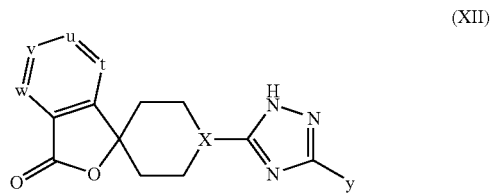

(XII)

(wherein t, u, v, w, X and y have each the same meaning as defined above), and optionally removing the protecting group(s) therefrom.

The present process refers to a process for preparing a compound of the formula (I) wherein. Az is an optionally substituted 1,2,4-triazol-3-yl group, namely a compound of the formula (I-4).

The reaction between a compound of the formula (X) and a compound of the formula (XI) is usually carried out by employing 0.5 to 5 moles, preferably 0.7 to 3 moles of the compound (XI), relative to 1 mole of the compound (X)

The reaction is usually carried out in the absence or presence of an inert solvent. Preferred examples of the inert solvent are benzene, toluene, xylene, methylene chloride, chloroform, hexane, and a mixture thereof and the like.

The reaction temperature is usually from −20° C. to the boiling point of the solvent used, preferably 20° C. to 200° C.

The reaction time is usually from 30 minutes to 7 days, preferably from 3 hours to 3 days.

It is preferred to perform the above reaction in the presence of a Lewis acid. As the Lewis acid, there are exemplified by zinc dichloride, titanium tetrachloride, scandium trifluoromethanesulfonate, yttrium trifluoromethanesulfonate, lanthanum trifluoromethanesulfonate, and the like.

The amount of the Lewis acid to be used is usually 10 to 200 mole %, preferably 20 to 100 mole %, relative to 1 mole of a compound of the formula (X).

When the reaction is carried out in the presence of a Lewis acid, it may be conducted without any solvent or preferably in the presence of a solvent such as methylene chloride, chloroform, benzene, toluene, xylene, and a mixture thereof.

The reaction temperature is usually from 0° C. to the boiling point of the solvent used, preferably room temperature, to 150° C.

The reaction time is usually from 1 hour to 7 days, preferably from 12 hours to 3 days.

A compound of the formula (I-4) can be produced by treating a reaction mixture in the usual way after removal of the said protecting group(s) when the product has a protecting group after completion of the reaction, or by treating the mixture directly in the usual way when the protecting group is absent.

The removal of the protecting group(s), and the post-treatment may be conducted according to a method similar to the method described in the above Production Process 1.

Production Process 5

A compound of the formula (I-5):

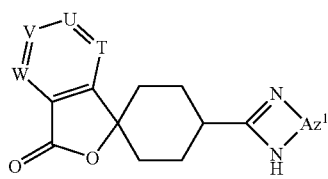

(I-5)

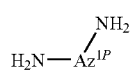

(wherein $Az^1$ is a group comprising a monocyclic azole having bonds attached respectively to the adjacent ring atoms, said monocyclic azole being optionally substituted by a substituent selected from the group consisting of halogen, cyano, lower alkyl, halo-lower alkyl, hydroxy, lower alkoxy, halo-lower alkoxy, lower alkoxycarbonyl, lower alkylsulfonyl, lower alkylsulfonyloxy, —N($R^1$)$R^2$ and -$Q^1$-$Ar^1$; and $Ar^1$, $Q^1$, $R^1$, $R^2$, T, U, V and W are the same meaning as defined above), can be prepared by reacting a compound of the formula (XIII):

(XIII)

(wherein $Az^{1P}$ is a group comprising a monocyclic azole having bonds attached respectively to the adjacent ring atoms, said monocyclic azole being optionally substituted by a substituent selected from the group consisting of halogen, cyano, lower alkyl, halo-lower alkyl, lower alkoxy, halo-lower alkoxy, lower alkoxycarbonyl, lower alkylsulfonyl, lower alkylsulfonyloxy, —N($R^{1P}$)$R^{2P}$, $Q^{1P}$-$Ar^{1P}$, and optionally protected hydroxy; and $Ar^{1P}$, $Q^{1P}$, $R^{1P}$ and $R^{2P}$ are the same meaning as defined above) or its salt with a compound of the formula (XIV)

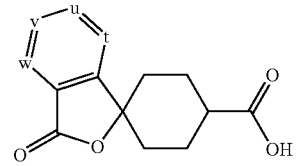

(XIV)

(wherein t, u, v and w are the same meaning as defined above) or its salt or reactive derivative to give a compound of the formula (XV):

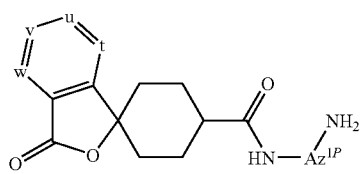

(XV)

(wherein $Az^{1P}$, t, u, v and w have each the same meaning as defined above), followed by subjecting the compound (XV) to intramolecular dehydrative ring closure to give a compound of the formula (XVI):

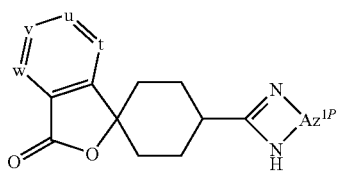

(XVI)

(wherein $Az^{1P}$, t, u, v and w have each the same meaning as defined above), and optionally removing the protecting group(s).

The present process refers to a process for preparing a compound of the formula (I) wherein Az is an optionally substituted bicyclic aromatic ring wherein the same or different azoles are fused, and X is methine, namely a compound of the formula (I-5).

The reaction between a compound of the formula (XIII) and a compound of the formula (XIV) is usually carried out by employing 0.5 to 5 moles, preferably 0.7 to 3 moles of the compound (XIV), relative to 1 mole of the compound (XIII).

The reaction is usually carried out in an inert solvent. Preferred examples of the inert solvent are methylene chloride, chloroform, tetrahydrofuran, dimethylformamide, pyridine, and a mixture thereof.

The above reaction is preferably carried out in the presence of a condensing agent including, for example, N,N'-dicyclohexylcarbodiimide, N,N'-diisopropylcarbodiimide, 1-(3-dimethylaminopropyl)-3-ethylcarbodiimide, 1-(3-dimethylaminopropyl)-3-ethylcarbodiimide hydrochloride, benzotriazol-1-yloxy-tris-(dimethylamino)phosphonium hexafluorophosphate, benzotriazol-1-yloxy-tris-pyrrolidinophosphonium hexafluorophosphate, bromotris(dimethylamino)phosphonium hexafluorophosphate, diphenylphosphoric azide, 1,1'-carbonyldiimidazole and the like.

Such condensing agent can be usually used in 1 to excess moles, preferably 1 to 1.5 moles, relative to 1 mole of a compound of the formula (XIV).

The reaction temperature is usually from −50° C. to 100° C., preferably −20° C. to 50° C.

The reaction time is usually from 30 minutes to 7 days, preferably from 1 to 24 hours.

In place of the carboxylic acid of the formula (XIV), a reactive derivative of said carboxylic acid may be reacted with a compound of the formula (XIII), thereby to produce a compound of the formula (XV) can be prepared.

Examples of such activated derivatives of the carboxylic acid of the formula (XIV) are acid halides, mixed anhydrides, active esters, active amides and the like.

The acid halides of the carboxylic acid of the formula (XIV) can be prepared by reacting a carboxylic acid of the formula (XIV) with a halogenating agent in a conventional manner. The halogenating agent used includes, for example, thionyl chloride, phosphorus trichloride, phosphorus pentachloride, phosphorus oxychloride, phosphorus tribromide, oxalyl chloride, phosgene and the like.

The mixed anhydrides of the carboxylic acid of the formula (XIV) can be prepared by reacting a carboxylic acid of the formula (XIV) with an alkyl chlorocarbonate (e.g. ethyl chlorocarbonate), an aliphatic carboxylic acid chloride (e.g. pivaloyl chloride) and the like according to the conventional method.

The active esters of the carboxylic acid of the formula (XIV) can be prepared by reacting a carboxylic acid of the formula (XIV) with an N-hydroxy compound (e.g. N-hydroxysuccinimide, N-hydroxyphthalimide, 1-hydroxybenzotriazole); a phenol compound (e.g. 4-nitrophenol, 2,4-dinitrophenol, 2,4,5-trichlorophenol, pentachlorophenol) and the like in the presence of a condensing agent (e.g. N,N'-dicyclohexylcarbodiimide, 1-(3-dimethylaminopropyl)-3-ethylcarbodiimide) according to the conventional method.

The active amides of the carboxylic acid of the formula (XIV) can be prepared by reacting a carboxylic acid of the formula (XIV) with 1,1'-carbonyldiimidazole, 1,1'-carbonylbis(2-methyl-imidazole) and the like according to the conventional method.

The reaction between a compound of the formula (XIII) and a reactive derivative of the carboxylic acid of the formula (XIV) is usually carried out by employing 0.5 moles to excess moles, preferably 1 to 1.5 moles of the reactive derivative of the carboxylic acid (XIV), relative to 1 mole of compound (XIII).

The reaction is usually carried out in an inert solvent. Preferable examples of such inert solvent are methylene chloride, chloroform, tetrahydrofuran, dimethylformamide, pyridine, and a mixture thereof and the like.

The above reaction may proceed in the absence of a base, but it is preferable to carry out the reaction in the presence of a base to promote the reaction smoothly.

The bases include organic bases (e.g., triethylamine, diisopropylethylamine, pyridine, 4-dimethylaminopyridine), or inorganic bases (e.g. sodium hydroxide, potassium hydroxide, sodium carbonate, potassium carbonate, sodium hydrogen carbonate).

It is preferable to employ 1 to excessive moles of said base to 1 mole of a compound of the formula (XIII). When the base is liquid, such base can also be used as a solvent.

The reaction temperature is usually −50° C. to 100° C. preferably −20° C. to 50° C.

The reaction time is usually 5 minutes to 7 days, preferably 30 minutes to 24 hours.

A usual treatment is carried out after completion of the reaction to obtain a crude product of a compound of formula (XV). The resulting compound of the formula (XV) may be, with or without purification according to the conventional manner, subjected to optional intramolecular ring closure condensation.

The intramolecular ring closure condensation for preparing a compound of the formula (XVI) from the compound (XV) is usually carried out in the presence of an inert solvent or without any solvent.

Preferred examples of such inert solvents are ethanol, propanol, butanol, pentanol, 1,4-dioxane, dimethoxyethane, dimethylformamide, dimethyl sulfoxide, benzene, toluene, xylene, and a mixture thereof and the like.

The reaction temperature is usually from room temperature to the boiling point of the solvent used, preferably 80° C. to 190° C.

The reaction time is usually from 5 hours to 7 days, preferably from 12 hours to 3 days.

The above ring closure may be carried out in the presence of a dehydrating agent or a catalytic amount of Lewis acid. The dehydrating agent includes, for example, cesium fluoride, phosphorus oxychloride, phosphorus pentachloride, polyphosphoric acid, thionyl chloride and the like. As the Lewis acid, there are exemplified by scandium trifluoromethanesulfonate, yttrium trifluoromethanesulfonate, lanthanum trifluoromethanesulfonate, lanthanide trifluoromethanesulfonate and the like. The ring closure is carried out preferably without any solvent, or in the presence of a solvent such as methylene chloride, chloroform, benzene, toluene, xylene and the like or a mixture thereof.

The amount of the dehydrating agent to be used is usually 1 mole to excessive moles, preferably 2 to 10 moles, relative to 1 mole of a compound of the formula (XV), and that of the Lewis acid is 10 to 50 mole %, preferably 10 to 30 mole %.

In general, the reaction temperature is preferably from room temperature to the boiling point of the solvent used.

The reaction time is from 1 hour to 7 days, preferably from 5 hours to 3 days.

A compound of the formula (I-5) can be produced by treating the reaction mixture in the usual way after removal of the said protecting group(s) when the product has a protecting group after completion of the reaction, or by treating the mixture directly in the usual way when the protecting group is absent.

The removal of the protecting group(s), and the post-treatment may be conducted according to a method similar to the method described in the above Production Process 1.

Production Process 6

A compound of the formula (I-6):

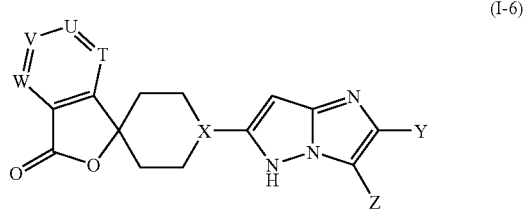

(I-6)

(wherein T, U, V, W, X, Y and Z are the same meaning as defined above), can be prepared by reacting a compound of the formula (II):

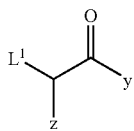

(II)

(wherein L¹, y and z are the same meaning as defined above), with a compound of the formula (XVII):

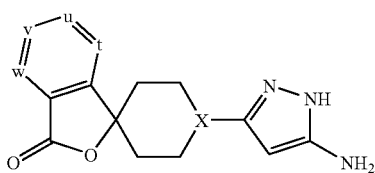

(XVII)

(wherein t, u, v, w and X are the same meaning as defined above) or its salt to give a compound of the formula (XVIII):

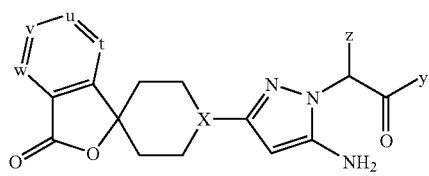

(XVIII)

(wherein t, u, v, w, X, y and z have each the same meaning as defined above), followed by subjecting the compound of the formula (XVIII) to intramolecular dehydrative ring closure to give a compound of the formula (XIX):

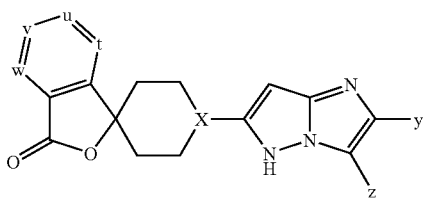

(XIX)

(wherein t, u, v, w, X, y and z have each the same meaning as defined above), and optionally removing the protecting group(s).

The present process refers to a process for preparing a compound of the formula (I) wherein Az is an optionally substituted 5H-imidazo[1,2-b]pyrazol-6-yl group, namely a compound of the formula (I-6).

The reaction between a compound of the formula (II) and a compound of the formula (XVII) is usually carried out by employing 0.5 moles to excessive moles, preferably 0.5 to 1.5 moles of the compound (XVII), relative to 1 mole of the compound (II).

The reaction is usually carried out in an inert solvent. Preferred examples of such inert solvent are methylene chloride, chloroform, tetrahydrofuran, dioxane, dimethylformamide, N-methylpyrrolidone, dimethyl sulfoxide, and a mixture thereof and the like.

The above reaction may be carried out preferably in the presence of a base. The bases used include organic bases (e.g. triethylamine, diisopropylethylamine, pyridine, 4-dimethylaminopyridine), or inorganic bases (e.g. sodium hydrogen carbonate, sodium carbonate, potassium carbonate, cesium carbonate, sodium hydroxide, potassium hydroxide).

The amount of the base to be used is usually equivalent mole to excessive moles, preferably 1 to 5 moles, of a compound of the formula (II).

The reaction temperature is usually 0° C. to 200° C. preferably 20° C. to 150° C.

The reaction time is usually 5 minutes to 7 days, preferably 30 minutes to 24 hours.

A usual treatment is carried out after completion of the reaction to obtain a crude product of a compound of the formula (XVIII). The resulting compound of the formula (XVIII) may be subjected, with or without purification according to the conventional manner, to optional intramolecular ring closure condensation.

The intramolecular ring closure condensation for preparing a compound of the formula (XIX) from the compound (XVIII) is usually carried out in the presence of an inert solvent or without any solvent.

Preferred examples of such inert solvents are ethanol, propanol, butanol, pentanol, 1,4-dioxane, dimethoxyethane, dimethylformamide, dimethyl sulfoxide, benzene, toluene, xylene, and a mixture thereof and the like.

The reaction temperature is usually from room temperature to the boiling point of the solvent used, preferably 80° C. to 190° C.

The reaction time is usually from 5 hours to 7 days, preferably from 12 hours to 3 days.

The above ring closure may be carried out in the presence of a dehydrating agent or a catalytic amount of Lewis acid. The dehydrating agent includes, for example, cesium fluoride, phosphorus oxychloride, phosphorus pentachloride, polyphosphoric acid, thionyl chloride and the like. As the Lewis acid, there are exemplified by scandium trifluoromethanesulfonate, yttrium trifluoromethanesulfonate, lanthanum trifluoromethanesulfonate, lanthanide trifluoromethanesulfonate and the like. The ring closure is carried out preferably without any solvent, or in the presence of a solvent such as methylene chloride, chloroform, benzene, toluene, xylene and the like or a mixture thereof.

The amount of the dehydrating agent to be used is usually 1 mole to excessive moles, preferably 2 to 10 moles, relative to 1 mole of a compound of the formula (XVIII), and that of the Lewis acid is 10 to 50 mole %, preferably 10 to 30 mole %.

In general, the reaction temperature is preferably from room temperature to the boiling point of the solvent used.

The reaction time is from 1 hour to 7 days, preferably from 5 hours to 3 days.

A compound of the formula (I-6) can be produced by treating the reaction mixture in the usual way after removal of the said protecting group(s) when the product has a protecting group after completion of the reaction, or by treating the mixture directly in the usual way when the protecting group is absent.

The removal of the protecting group(s), and the post-treatment may be conducted according to a method similar to the method described in the above Production Process 1.

The compounds of the formula (I-1), (I-2), (I-3), (I-4), (I-5) or (I-6) may be readily isolated and purified by the conventional separation technique, and examples of such technique are solvent extraction, recrystallization, column chromatography, preparative thin layer chromatography and the like.

These compounds may be converted into the pharmaceutically acceptable salts or esters by the conventional method, and on the contrary, the conversion of the salts or esters into free compounds may also be carried out according to the conventional method.

The compounds of the formulae (II), (III), (V), (VI), (VIII), (X), (XI), (XIII), (XIV) and (XVII) are commercially available, or can be prepared according to the common methods or analogous methods thereto, or the methods shown in Examples and Reference Examples, optionally employed in combination.

Although there is no particular limitation to "salts" of compounds of the formulae (III), (V), (VI), (X), (XI), (XIII), (XIV) and (XVII) so long as they do not affect the reaction, such salts, include the common salts, for example, base addition salt to the carboxyl group when the compound has a carboxyl group, or acid addition salt to the amino or basic heterocyclic group when the compound has amino or basic heterocyclic group(s), and the like.

Aforesaid base addition salts include salts with alkali metals (for example sodium, potassium); alkaline earth metals (for example calcium, magnesium); ammonium or organic amines (for example trimethylamine, triethylamine, dicyclohexylamine, ethanolamine, diethanolamine, triethanolamine, procaine, N,N'-dibenzylethylenediamine), and the like.

Aforesaid acid addition salts include inorganic acid salts (for example hydrochloride, sulfate, nitrate, phosphate, perchlorate), organic acid salts (for example maleate, fumarate, tartarate, citrate, ascorbate, trifluoroacetate), sulfonates (for example methanesulfonate, isethionate, benzenesulfonate, p-toluenesulfonate), and the like.

The utility of compounds of the present invention as a medicament is proved by the following pharmacological tests.

Pharmacological Test 1 (NPY Binding Inhibition Test)

cDNA sequence encoding human NPY Y5 receptor (cf. International patent publication number WO96/16542) was cloned into expression vectors pcDNA3, pRc/RSV (made by invitrogen Inc.) and pCI-neo (made by Promega Inc.). The expression vectors thus obtained were transfected to host cells COS-7, CHO and LM(tk-) (American Type Culture Collection) by cationic lipid method (Proceedings of the National Academy of Sciences of the United States of America, 84: 7413 (1987)) to give NPY Y5 receptor expression cells.

A membrane sample prepared from the cells which expressed NPY Y5 receptor was incubated together with a test compound and [$^{125}$I]peptideYY (made by NEN) (20,000 cpm) in man assay buffer (25 mM Tris buffer, pH 7.4, containing 10 mM magnesium chloride, 1 mM phenylmethylsulfonyl fluoride, 0.1% bacitracin and 0.5% bovine serum albumin) at 25° C. for 2 hours, then filtered through a glass filter GF/C and washed with 5 mM Tris buffer (pH7.4) containing 0.3% BSA. The radioactivity of the cake on the glass filter was measured. Non-specific binding was measured in the presence of 1 μM peptide YY, and a 50% Inhibitory Concentration ($IC_{50}$) of the test compound against specific peptide YY binding was determined (Endocrinology; 131: 2090 (1992)). The results are shown in Table 1.

TABLE 1

| Compounds | IC50(nM) |
|---|---|
| Example 1 | 1.7 |
| Example 14 | 1.7 |
| Example 19 | 1.6 |
| Example 23 | 2.7 |
| Example 24 | 3.9 |
| Example 29 | 3.9 |
| Example 30 | 4.2 |
| Example 34 | 3.5 |
| Example 35 | 3.3 |
| Example 36 | 1.8 |
| Example 45 | 1.5 |
| Example 46 | 1.5 |
| Example 47 | 2.2 |

As shown above, the compounds of this invention potently inhibited peptide YY (NPY homologue) binding to NPY Y5 receptors.

Pharmacological Test 2 (Brain/Cerebrospinal Fluid Transport Test)

A test compound was orally or intravenously administered to male SD rats (7-10 weeks old, 200-400 g), and whole blood was collected from the abdominal aorta of said rats anesthetized with ether at predetermined time, using a heparin-treated syringe. Then, the head skin was cut open, and a dental 30 G needle was inserted between the cervical vertebrae, and it was further inserted into the cavum subarachnoideale. After 50 to 100 μL cerebrospinal fluid had been collected by a 1 ml-syringe through a tube connected to said dental 30 G needle, the brain was extracted. The blood sample was centrifuged (4° C., 6,000 r.p.m., 10 minutes) to collect the plasma, to which was added 3-fold amount of ethanol containing an internal standard, and the mixture was stirred. The brain sample was homogenized after addition of 2 ml water, an aliquot of the homogenate was taken and 3-fold amount of ethanol containing an internal standard was added thereto and stirred. The cerebrospinal fluid was stirred after adding 3-fold amount of ethanol containing an internal standard. The samples thus obtained were allowed to stand at −20° C. for 20 minutes, and then centrifuged (4° C., 12,000 g, 10 minutes). The supernatant was analyzed by LC/MS/MS, and the concentration of the test compound in the plasma, brain, and cerebrospinal fluid were measured by the method using a relative calibration curve.

The results revealed that concentrations of the compound of Example 29 in the brain, cerebrospinal fluid and plasma were 3.01 nmol/g, 0.015 μM and 1.162 μM respectively, 2 hours after oral administration (10 mg/kg).

The compounds of the formula (I) can be administered orally or parenterally and, by formulating into a suitable administrable form, may be administered as an agent for treating or preventing various diseases including, for example, cardiovascular disorders such as angina, acute or congestive heart failure, myocardial infarction, hypertension, nephropathy, electrolyte abnormality, vasospasm, arteriosclerosis, etc.; central nervous system disorders such as bulimia, depression, anxiety, seizure, epilepsy, dementia, pain, alcoholism, drug withdrawal, circadian rhythm disorders, schizophrenia, memory impairment, sleep disorders, cognitive impairment, etc.; metabolic diseases such as obesity, diabetes, hormone abnormality, hypercholesterolemia, hyperlipidemia, gout, fatty liver, etc.; genital or reproductive disorders such as infertility, preterm labor, sexual dysfunction, etc.; gastro-intestinal disorders; respiratory disorder; inflammatory diseases; glaucoma; atherosclerosis; hypogonadism; hyperandrogenism; polycystic ovary syndrome; hirsutism; gastro-intestinal motility disorder; obesity-related gastro-esophageal reflux; obesity hypoventilation (Pickwickian syndrome); sleep apnea; inflammation; systemic inflammation of the vasculature; osteoarthritis; insulin resistance; bronchoconstriction; alcohol preference; metabolic syndrome (syndrome X); Alzheimer's disease; cardiac hypertrophy; left ventricular hypertrophy; hypertriglyceridemia; low HDL cholesterol; cardiovascular disorders such as coronary heart disease (CHD), cerebrovascular disease, stroke, peripheral vascular disease, and sudden death; gallbladder diseases; cancers (breast cancer, endometrial cancer, colon cancer); breathlessness; hyperuricemia; impaired fertility; low back pain; increased anesthetic risk; renal system diseases; renal abnormalities such as dysfunction in body fluid flow, abnormalities of material transportation, and renal failure; shock; arrhythmia; symptoms related to surge in sympathomimetic activity during or after operation on coronary artery or gastrointestinal tracts; diseases related to brain or central nervous system, such as cerebral infarction, neurodegeneration, cerebral stroke, cerebrovascular spasm or cerebral hemorrhage; symptoms related to pain or nociception; diseases related to abnormalities in gastrointestinal motility or secretion, such as various ileuses, urinary incontinence, and Crohn's disease; eating disorders such as anorexia and bulimia; inflammatory symptoms or diseases; asthma; bronchiole constriction; or diseases related to abnormal secretion of hormones such as luteinizing hormone, growth hormone, insulin, and luteotropic hormone.

In clinical use, the compounds of this invention may be administered after being formulated, together with pharmaceutically acceptable additives, into an appropriate preparation according to the mode of administration. As for said additives, those which are usually used in the field of pharmaceutical formulation may be used, for example, gelatin, lactose, sucrose, titanium oxide, starch, crystalline cellulose, hydroxypropyl methylcellulose, carboxymethylcellulose, corn starch, microcrystalline wax, white petrolatum, magnesium methasilicate aluminate, anhydrous calcium phosphate, citric acid, trisodium citrate, hydroxypropyl cellulose, sorbitol, sorbitan fatty acid ester, polysorbate, sucrose fatty acid ester, polyoxyethylene, hydrogenated castor oil, polyvinylpyrrolidone, magnesium stearate, light silicic anhydride, talc, vegetable oil, benzyl alcohol, gum arabic, propylene glycol, polyalkylene glycol, cyclodextrin or hydroxypropyl cyclodextrin and the like.

A mixture with said additives may be formulated into the form of solid preparations (for example tablets, capsules, granules, powder, suppositories); or liquid preparations (for example syrups, elixirs, injections). Such preparations may be formulated according to the techniques well known in the art of pharmaceutical formulation. Liquid preparations may be in the form of preparations which are dissolved or suspended in water or other appropriate media when used, and injectable preparations in particular may be dissolved or suspended in physiological saline or glucose solution if necessary, optionally together with a buffer and a preservative.

The compounds of the present invention are effective for humans or mammals other than humans in need of treatment or prevention of diseases. Mammals preferably include humans which may be male or female. As the mammal other than humans, there are exemplified by companion animals such as dog, cat and the like. The compounds of the present invention are effective against obesity or diseases related to obesity. An ordinarily skilled physician, veterinarian or clinician can readily determine whether or not treatment with the compound of the present invention is required.

When compounds of this invention are used clinically, for example, a daily dose for an adult is 0.01-100 mg/kg, preferably 0.03-1 mg/kg with simultaneous or divided administration when administered orally, and 0.001-10 mg/kg, preferably 0.001-0.1 mg/kg, more preferably 0.01-0.1 mg/kg with simultaneous or divided administration when administered parenterally, though the dose and the frequency of dosage may vary depending upon the sex, age, body weight, the degree of symptoms and the kind and range of the desired treatment effects.

An ordinarily skilled physician, veterinarian or clinician can readily determine and prescribe the effective amount of the drug required to prevent, suppress or arrest the progress of diseases.

All the said preparations may contain 1.0 to 100 wt. %, preferably 1.0 to 60 wt. % of compounds of this invention and may also contain other therapeutically effective compounds.

The compounds of the present invention can be used in combination with other agents useful for treating metabolic disorders and/or eating disorders. The individual component of such combinations can be administered separately at different times or concurrently in divided or single combination forms during the course of therapy. The instant invention is therefore to be understood as embracing all such regimes of simultaneous or divided administration and the term "administering" is to be interpreted accordingly. The scope of combinations of the compounds of this invention with other agents useful for treating metabolic disorders and/or eating disorders includes in principle any combination of any pharmaceutical composition useful for treating metabolic disorders and/or eating disorders.

Diabetes is caused by multiple factors and is most simply characterized by elevated levels of plasma glucose (hyperglycemia) in the fasting state. There are two generally recognized forms of diabetes: type 1 diabetes, or insulin-dependent diabetes mellitus (IDDM), in which patients produce little or no insulin, the hormone which regulates glucose utilization, and type 2 diabetes, or noninsulin-dependent diabetes mellitus (NIDDM), wherein patients produce insulin and even exhibit hyperinsulinemia (plasma insulin levels that are the same or even elevated in comparison with non-diabetic subjects), while at the same time demonstrating hyperglycemia. Type 1 diabetes is typically treated with exogenous insulin administered via injection. However, type 2 diabetics often develop "insulin-resistance", such that the effect of insulin in stimulating glucose and lipid metabolism in the main insulin-sensitive tissues, namely, muscle, liver and adipose tissues, is diminished. Patients who are insulin resistant but not diabetic have elevated insulin-levels that compensate for their insulin resistance, so that serum glucose levels are not elevated. In patients with NIDDM, the plasma insulin levels, even when they are elevated, are insufficient to overcome the pronounced insulin resistance, resulting in hyperglycemia. Thus, it is difficult to treat patients with NIDDM by single administration of foreign insulin.

Insulin resistance is primarily due to a receptor binding defect that is not yet completely understood. Resistance to insulin results in insufficient activation of glucose uptake, diminished oxidation of glucose and storage of glycogen in muscle, inadequate insulin repression of lipolysis in adipose tissue and inadequate glucose production and secretion by the liver. The persistent or uncontrolled hyperglycemia that occurs in diabetics is associated with increased morbidity and premature mortality. Type 2 diabetics are at increased risk of developing cardiovascular complications, e.g., atherosclerosis, coronary heart disease, stroke, peripheral vascular disease, hypertension, nephropathy, neuropathy and retinopathy.

Non-insulin dependent diabetes is also associated with cardiac hypertrophy, in particular left ventricular hypertrophy (Devereux, R. B., Circulation, 101:2271-2276 (2000)). Cardiac hypertrophy, such as left ventricular hypertrophy, is due to the response of the heart to chronic pressure or volume overload. Left ventricular hypertrophy (LVH) is characterized by thickening of the left ventricular wall, including increased left ventricular mass and increased left ventricular wall thickness, and is defined as a left ventricular mass index exceeding 131 $g/m^2$ of the body surface area in men, and 100 $g/m^2$ in women (Savage et al., The Framingham Study, Circulation, 75 (1 Pt 2): 26-33 (1987).

Left ventricular hypertrophy is independently associated with increased incidence of cardiovascular disease, such as congestive heart failure, ischaemic heart disease, cardiovascular and all-cause mortality, sudden death, and stroke. Regression of left ventricular hypertrophy has been associated with a reduction in cardiovascular risk. It has also been found that the incidence of morbid events in patients with progression of left ventricular hypertrophy is greater than in patients with regression of left ventricular hypertrophy.

Current treatments for hypertrophy include non-pharmacological interventions, such as weight reduction, sodium restriction, and aerobic physical exercise can reduce left ventricular mass (Ghali, J. K. et al., American Journal of Geriatric Cardiology, 6:38-49 (1997).

Many patients who have insulin resistance but have not yet developed type 2 diabetes are also at a risk of developing metabolic syndrome, also referred to as syndrome X, insulin resistance syndrome, or plurimetabolic syndrome. The period of 5 to 10 years preceding the development of impaired glucose tolerance is associated with a number of hormonal imbalances, which give rise to an enlargement of visceral fat mass, hypertension, insulin resistance, and hyperlipidemia (Bjornstop, P., Current Topics in Diabetes Research, eds. Belfore, F., Bergman, R. N., and Molinath, G. M., Front Diabetes, Basel, Karger, 12:182-192 (1993)). Similarly, metabolic syndrome is characterized by insulin resistance, along with abdominal obesity, hyperinsulinemia, hyperglycemia, syndrome X, low HDL and high VLDL. Although the causal relationship between the various components of metabolic syndrome remains to be confirmed, insulin resistance appears to play an important role (Requen, G. M., et al., N. Eng. J. Med. 334:374-381 (1996); Despres, J-P., et al., N. Engl. J. Med. 334:952-957 (1996); Wajchenberg, B. L., et al., Diabetes –Metabolism Rev. 10:19-29 (1994)). Metabolic syndrome patients, whether or not they develop overt diabetes mellitus, are at increased risk of developing the cardiovascular complications listed above. Associations have also been found between left ventricular hypertrophy and metabolic syndrome (Marcus, R. et. al. Circulation, 90:928-936 (1994); Lind, L. et al., J Hypertens. 13:433-38 (1995); Paolisso, G et al., Am J Hypertens., 10:1250-1256 (1997).

Diabetes is treated with a variety of therapeutic agents including insulin sensitizers, such as PPARγ agonists, such as glitazones; biguanides; protein tyrosine phosphatase-1B inhibitors; dipeptidyl peptidase IV inhibitors; insulin; insulin mimetics; sulfonylureas; meglitinides; α-glucoside hydrolase inhibitors; and α-amylase inhibitors.

Increasing the plasma level of insulin by administration of sulfonylureas (e.g. tolbutamide and glipizide) or meglitinides, which stimulate the pancreatic β-cells to secrete more insulin, and/or by injection of insulin when sulfonylureas or meglitinides become ineffective, can result in insulin concentrations high enough to stimulate insulin-resistant tissues. However, dangerously low levels of plasma glucose can result, and increasing insulin resistance due to the even higher plasma insulin levels can occur. The biguanides increase insulin sensitivity resulting in some correction of hyperglycemia. Alpha-amylase inhibitors inhibit the enzymatic degradation of starch or glycogen into maltose, which also reduces the amounts of bioavailable sugars. Metformin monotherapy is often used for treating type 2 diabetic patients who are also obese and/or dyslipidemic. Lack of appropriate response to metformin is often followed by treatment with sulfonylureas, thiazolidinediones, insulin, or alpha glucosidase inhibitors. However, the two biguanides, phenformin and metformin, can also induce lactic acidosis and nausea/diarrhea, respectively. Alpha glucosidase inhibitors, such as acarbose, work by delaying absorption of glucose in the intestine.

The glitazones, also known as thiazolidinediones (i.e. 5-benzylthiazolidine-2,4-diones), are a more recently described class of compounds with potential for a novel mode of action in ameliorating many symptoms of type 2 diabetes. These agents substantially increase insulin sensitivity in muscle, liver and adipose tissue in several animal models of type 2 diabetes resulting in partial or complete correction of the elevated plasma levels of glucose without occurrence of hypoglycemia. The glitazones that are currently marketed are agonists of the peroxisome proliferator activated receptor (PPAR) gamma subtype. PPAR-gamma agonism is generally believed to be responsible for the improved insulin sensitization that is observed with the glitazones. Newer PPAR agonists that are being developed for treatment of Type 2 diabetes and/or dyslipidemia are agonists of one or more of the PPAR alpha, gamma and delta subtypes.

However, treatment of diabetes with PPAR γ agonists has been associated with cardiac hypertrophy, or an increase in heart weight. Recent labeling revisions for Avandia (rosiglitazone maleate), a PPARγ agonist, indicate that patients may experience fluid accumulation and volume-related events such as edema and congestive heart failure. Cardiac hypertrophy related to PPARγ agonist treatment is typically treated by withdrawing PPAR treatment.

Treatment of type 2 diabetes also typically includes physical exercise, weight control and dieting. While physical exercise and reductions in dietary intake of calories will dramatically improve the diabetic condition, compliance with this treatment is very poor because of well-entrenched sedentary lifestyles and excess food consumption, especially of foods containing high amounts of saturated fat. However, weight reduction and increased exercise are difficult for most people with diabetes.

Abnormal glucose homeostasis is also associated both directly and indirectly with, obesity, hypertension and dyslipidemias. Obesity increases the likelihood of insulin resistance, and increases the likelihood that the resulting insulin resistance will increase with increasing body weight. Therefore, therapeutic control of glucose homeostasis, lipid metabolism, obesity and hypertension are critically important in the clinical management and treatment of diabetes mellitus.

Obesity, which can be defined as a body weight more than 20% above the ideal body weight, is a major health concern in Western societies. It is estimated that one person per three adults in the United States are overweight or obese. Obesity is the result of appositive energy balance, as a consequence of increased ratio of caloric intake to energy expenditure. The molecular factors regulating food intake and body weight balance are incompletely understood. [B. Staels et al., J. Biol. Chem. 270 (27), 15958 (1995); F. Lonnquist et al., Nature Medicine 1(9), 950 (1995)]. Although the genetic and/or environmental factors leading to obesity are poorly understood, several genetic factors have been identified.

Epidemiological studies have shown that increasing degrees of overweight and obesity are important predictors of decreased life expectancy. Obesity causes or exacerbates many health problems, both independently and in association with other diseases. The medical problems associated with obesity, which can be serious and life-threatening, include type 2 diabetes mellitus, hypertension, elevated plasma insulin concentrations, insulin resistance, dyslipidemias, hyperlipidemia, endometrial, breast, prostate, kidney and colon cancer, osteoarthritis; respiratory complications, such as obstructive sleep apnea, gallstones, arteriosclerosis, heart disease, abnormal heart rhythms, and heart arrythmias (Kopelman, P. G., Nature 404, 635-643 (2000)). Obesity is also associated with metabolic syndrome, cardiac hypertrophy, in particular left ventricular hypertrophy, premature death, and with a significant increase in mortality and morbidity from stroke, myocardial infarction, congestive heart failure, coronary heart disease, and sudden death.

Abdominal obesity has been linked with a much higher risk of coronary artery disease, and with three of its major risk factors: high blood pressure, diabetes that starts in adulthood, and high levels of fats (lipids) in the blood. Losing weight dramatically reduces these risks. Abdominal obesity is further closely associated with glucose intolerance, hyperinsulinemia, hypertriglyceridemia, and other disorders associated with metabolic syndrome (syndrome X), such as raised high blood pressure, decreased levels of high density lipoproteins (HDL) and increased levels of very low density lipoproteins (VLDL) (Montague et al., Diabetes, 2000, 49: 883-888).

Obesity and obesity-related disorders, such as diabetes, are often treated by encouraging patients to lose weight by reducing their food intake or by increasing their exercise level, thereby increasing their energy output. A sustained weight loss of 5% to 10% of body weight has been shown to improve the comorbidities associated with obesity, such as diabetes, and can lead to improvement of obesity-related disorders such as diabetes, left ventricular hypertrophy, osteoarthritis, and pulmonary and cardiac dysfunction.

Weight loss drugs used for the treatment of obesity include orlistat (Davidson, M. H. et al. (1999) JAMA 281:235-42), dexfenfluramine (Guy Grand, B. et al. (1989) Lancet 2:1142-5), sibutramine (Bray, G. A. et al. (1999) Obes. Res. &: 189-98) and phentermine (Douglas, A. et al. (1983) Int. J. Obes. 7:591-5). However, the side effects of these drugs and anti-obesity agents may limit their use. Dexfenfluramine was withdrawn from the market because of suspected heart valvulopathy; orlistat is limited by gastrointestinal side effects; and the use of sibutramine is limited by its cardiovascular side effects which have led to reports of deaths and its withdrawal from the market in Italy.

The term "diabetes," as used herein, includes both insulin-dependent diabetes mellitus (i.e., IDDM, also known as type 1 diabetes) and non-insulin-dependent diabetes mellitus (i.e., NIDDM, also known as Type 2 diabetes). The compositions of the present invention are useful for treating both Type 1 and Type 2 diabetes. The compositions are especially effective for treating Type 2 diabetes. The compositions of the present invention are also useful for treating and/or preventing gestational diabetes mellitus.

Treatment of diabetes mellitus refers to the administration of a compound or combination of the present invention to treat diabetes. One outcome of treatment may be decreasing the glucose level in a subject with elevated glucose levels. Another outcome of treatment may be decreasing insulin levels in a subject with elevated insulin levels. Another outcome of treatment is decreasing plasma triglycerides in a subject with elevated plasma triglycerides. Another outcome of treatment is decreasing LDL cholesterol in a subject with high LDL cholesterol levels. Another outcome of treatment is increasing HDL cholesterol in a subject with low HDL cholesterol levels. Another outcome of treatment is increasing insulin sensitivity. Another outcome of treatment may be enhancing glucose tolerance in a subject with glucose intolerance. Yet another outcome of treatment may be decreasing insulin resistance in a subject with increased insulin resistance or elevated levels of insulin.

The compounds, or combined compositions of the present invention are useful for the prevention of diabetes.

The term "hypertension" as used herein includes essential, or primary, hypertension wherein the cause is not known or where hypertension is due to greater than one cause, such as changes in both the heart and blood vessels; and secondary hypertension wherein the cause is known. Causes of secondary hypertension include, but are not limited to obesity; kidney disease; hormonal disorders; use of certain drugs, such as oral contraceptives, corticosteroids, cyclosporin, and the like. The term "hypertension" encompasses high blood pressure, in which both the systolic and diastolic pressure levels are elevated, and isolated systolic hypertension, in which only the systolic pressure is elevated to greater than or equal to 140 mm Hg, while the diastolic pressure is less than 90 mm Hg. One outcome of treatment is decreasing blood pressure in a subject with high blood pressure.

Dyslipidemias or disorders of lipid metabolism, include various, conditions characterized by abnormal concentrations of one or more lipids (i.e. cholesterol and triglycerides), and/or apolipoproteins (i.e., apolipoproteins A, B, C and E), and/or lipoproteins (i.e., the macromolecular complexes formed by the lipid and the apolipoprotein that allow lipids to circulate in blood, such as LDL, VLDL and IDL). Hyperlipidemia is associated with abnormally high levels of lipids, LDL and VLDL cholesterol, and/or triglycerides.

The term "metabolic syndrome", also known as syndrome X, is defined in the Third Report of the National Cholesterol Education Program Expert Panel on Detection, Evaluation and Treatment of High Blood Cholesterol in Adults (ATP-III). E. S. Ford et al., JAMA, vol. 287 (3), Jan., 16, 2002, pp 356-359. Briefly, a person is defined as having metabolic syndrome if the person has three or more of the following symptoms: abdominal obesity, hypertriglyceridemia, low HDL cholesterol, high blood pressure, and high fasting plasma glucose. The criteria for these are defined in ATP-III.

The term "left venticular hypertrophy" (LVH) as used herein includes three patterns of left ventricular hypertrophy that have been identified based on left ventricular mass index (LVMI=left ventricular mass in grams divided by body surface area in meters2) and relative wall thickness (RWT=2× posterior wall thickness/left ventricular end diastolic diameter). Concentric LVH is typically exemplified by a left ventricular mass index of 144 and a relative wall thickness of 0.52; eccentric LVH is typically exemplified by a left ventricular mass index of 136 and a relative wall thickness of 0.38; and concentric left ventricular remodeling which is typically exemplified by a LVMI of 93 and a relative, wall thickness of 0.49. Normal LVMI are typically 85 and normal RWT approximately 0.36. Patients with concentric left ventricular (LV) remodeling have a cardiovascular risk intermediate between those with normal left ventricular structure and those with left ventricular hypertrophy.

One outcome of treatment of diabetes while minimizing cardiac hypertrophy, or left ventricular hypertrophy, may be a decrease in ventricular mass. Another outcome of treatment of diabetes while minimizing cardiac hypertrophy or left ventricular hypertrophy may be a decrease in the rate of increase of ventricular mass. Another outcome of treatment of diabetes while minimizing cardiac hypertrophy or left ventricular hypertrophy may be a decrease in ventricular wall thickness. Another outcome of treatment of diabetes while minimizing cardiac hypertrophy of left ventricular hypertrophy may be the decrease in the rate of increase in ventricular wall thickness.

The term "obesity" as used herein is a condition in which there is an excess of body fat. The operational definition of obesity is based on the Body Mass Index (BMI), which is calculated as body weight per height in meters squared (kg/m$^2$) "Obesity" refers to a condition whereby an otherwise healthy subject has a Body Mass Index (BMI) greater than or equal to 30 kg/m$^2$, or a condition whereby a subject with at least one co-morbidity has a BMI greater than or equal to 27 kg/m$^2$. An "obese subject" is an otherwise healthy subject with a Body Mass Index (BMI) greater than or equal to 30 kg/m$^2$ or a subject with at least one co-morbidity with a BMI greater than or equal to 27 kg/m$^2$. A "subject at risk of obesity" is an otherwise healthy subject with a BMI of 25 kg/m$^2$ to less than 30 kg/m$^2$ or a subject with at least one co-morbidity with a BMI of 25 kg/m$^2$ to less than 27 kg/m$^2$.

The increased risks associated with obesity occur at a lower Body Mass Index (BMI) in Asians. In Asian countries, including Japan, "obesity" refers to a condition whereby a subject with at least one obesity-induced or obesity-related co-morbidity, that requires weight reduction or that would be improved by weight reduction, has a BMI greater than or equal to 25 kg/m$^2$. In Asian countries, including Japan, an "obese subject" refers to a subject with at least one obesity-induced or obesity-related co-morbidity that requires weight reduction or that would be improved by weight reduction, with a BMI greater than or equal to 25 kg/m$^2$. In Asia-Pacific, a "subject at risk of obesity" is a subject with a BMI of greater than 23 kg/m$^2$ to less than 25 kg/m$^2$.

As used herein, the term "obesity" is meant to encompass all of the above definitions of obesity.

Obesity-induced or obesity-related co-morbidities include, but are not limited to, diabetes, non-insulin dependent diabetes mellitus—type 2, diabetes associated with obesity, impaired glucose tolerance, impaired fasting glucose, insulin resistance syndrome, dyslipidemia, hypertension, hypertension associated with obesity, hyperuricacidemia, gout, coronary artery disease, myocardial infarction, angina pectoris, sleep apnea syndrome, Pickwickian syndrome, fatty liver; cerebral infarction, cerebral thrombosis, transient ischemic attack, orthopedic disorders, arthritis deformans, lumbodynia, emmeniopathy, and infertility. In particular, co-morbidities include: hypertension, hyperlipidemia, dyslipidemia, glucose intolerance, cardiovascular disease, sleep apnea, diabetes mellitus, and other obesity-related conditions.

Treatment of obesity and obesity-related disorders refers to the administration of the compounds or combinations of the present invention to reduce or maintain the body weight of an obese subject. One outcome of treatment may be reducing the body weight of an obese subject relative to that subject's body weight immediately before the administration of the compounds or combinations of the present invention. Another outcome of treatment may be preventing body weight regain of body weight previously lost as a result of diet, exercise, or pharmacotherapy. Another outcome of treatment may be decreasing the occurrence of and/or the severity of obesity-related diseases. The treatment may suitably result in a reduction in food or calorie intake by the subject, including a reduction in total food intake, or a reduction of intake of specific components of the diet such as carbohydrates or fats; and/or the inhibition of nutrient absorption; and/or the inhibition of the reduction of metabolic rate; and in weight reduction in patients in need thereof. The treatment may also result in an alteration of metabolic rate, such as an increase in metabolic rate, rather than or in addition to an inhibition of the reduction of metabolic rate; and/or in minimization of the metabolic resistance that normally results from weight loss.

Prevention of obesity and obesity-related disorders refers to the administration of the compounds or combinations of the present invention to reduce or maintain the body weight of a subject at risk of obesity. One outcome of prevention may be reducing the body weight of a subject at risk of obesity relative to that subject's body weight immediately before the administration of the compounds or combinations of the present invention. Another outcome of prevention may be preventing body weight regain of body weight previously lost as a result of diet, exercise, or pharmacotherapy. Another outcome of prevention may be preventing obesity from occurring if the treatment is administered prior to the onset of obesity in a subject at risk of obesity. Another outcome of prevention may be decreasing the occurrence and/or severity of obesity-related disorders if the treatment is administered prior to the onset of obesity in a subject at risk of obesity. Moreover, if treatment is commenced in already obese subjects, such treatment may prevent the occurrence, progression or severity of obesity-related disorders, such as, but not limited to, arteriosclerosis, Type 2 diabetes, polycystic ovary disease, cardiovascular diseases, osteoarthritis, dermatological disorders, hypertension, insulin resistance, hypercholesterolemia, hypertriglyceridemia, and cholelithiasis.

The term "atherosclerosis" as used herein encompasses vascular diseases and conditions that are recognized and understood by physicians practicing in the relevant fields of medicine. Atherosclerotic cardiovascular disease, coronary heart disease (also known as coronary artery disease or ischemic heart disease), cerebrovascular disease and peripheral vessel disease are all clinical manifestations of atherosclerosis and are therefore encompassed by the terms "atherosclerosis" and "atherosclerotic disease". The combination comprised of a therapeutically effective amount of an anti-obesity agent in combination with a therapeutically effective amount of an anti-diabetic agent may be administered to prevent or reduce the risk of occurrence, or recurrence where the potential exists, of a coronary heart disease event, a cerebrovascular event, or intermittent claudication. Coronary heart disease events are intended to include CHD death, myocardial infarction (i.e., a heart attack), and coronary revascularization procedures. Cerebrovascular events are intended to include ischemic or hemorrhagic stroke (also known as cerebrovascular accidents) and transient ischemic attacks. Intermittent claudication is a clinical manifestation of peripheral vessel disease. The term "atherosclerotic disease event" as used herein is intended to encompass coronary heart disease events, cerebrovascular events, and intermittent claudication. It is intended that persons who have previously experienced one or more non-fatal atherosclerotic disease events are those for whom the potential for recurrence of such an event exists.

Circadian rhythms affect a variety of physiological parameters: rest-activity, sleep-wake cycles, body temperature, rhythms in hormone levels, oscillations in general physiology and the like. When these parameters are out of synchrony with the daily clock, a circadian rhythm imbalance occurs which can affect physiology, performance on a variety of tasks and one's emotional well being. The present invention is useful, for example, in the prevention or treatment of conditions associated with circadian rhythmicity as well as mental and physical disorders associated with travel across time zones and with rotating shift-work schedules.

In another embodiment, the present invention provides a method for the prevention or treatment of a circadian rhythm disorder in a mammal, including time-zone change (jet-lag) syndrome, shift-work sleep disorder, delayed sleep-phase syndrome, advanced sleep-phase syndrome, and non-24-hour sleep-wake disorder, which comprises administering to the mammal an effective amount of a NPY Y5 receptor antagonist.

In another embodiment, the present invention provides a method for shortening the time of re-entrainment (return to normal entrainment of the circadian rhythms; synchronized to the environmental light-dark cycle) in a subject following a shift in the sleep-wake cycle which comprises administering to the subject an appropriate amount of a NPY Y5 antagonist.

In another embodiment, the present invention provides a method for alleviating the effects of jet lag in a traveler, especially a mammal, which comprises administering to the traveler an alertness increasing amount of a NPY Y5 antagonist. The purpose of this embodiment is to assist the body to adjust physiologically to the changes in sleep and feeding patterns when crossing several time zones.

In another more preferred embodiment, the present invention provides a method for resetting the internal circadian clock in a subject to match the subject's current activity/sleep cycle. For example shift workers changing from a day to a night shift or vice versa, which comprises administering to the subject an appropriate amount of a NPY Y5 antagonist.

The present invention is further directed to the use of NPY Y5 antagonist, for enhancing or improving sleep quality as well as preventing and treating sleep disorders and sleep disturbances in a mammal. In particular, the present invention provides a method for enhancing or improving sleep quality by increasing sleep efficiency and augmenting sleep maintenance. In addition, the present invention provides a method for preventing and treating sleep disorders and sleep disturbances in a mammal which comprising the administration of a NPY Y5 antagonist. The present invention further provides a pharmaceutical composition for enhancing or improving sleep quality and increasing sleep efficiency and sleep maintenance. The present invention is useful for the treatment of sleep disorders, including Disorders of Initiating and Maintaining Sleep (insomnias) ("DIMS") which can arise from psychophysiological causes, as a consequence of psychiatric disorders (particularly related to anxiety), from drugs and alcohol use and abuse (particularly during withdrawal stages), childhood onset DIMS, nocturnal myoclonus and restless legs and non specific REM disturbances as seen in ageing.

The following outcomes in a subject which are provided by the present invention may be correlated to enhancement in sleep quality: an increase in the value which is calculated from the time that a subject sleeps divided by the time that a subject is attempting to sleep; a decrease in sleep latency (the time it takes to fall asleep); a decrease in the number of awakenings during sleep; a decrease in the time spent awake following the initial onset of sleep; an increase in the total amount of sleep; an increase the amount and percentage of REM sleep; an increase in the duration and occurrence of REM sleep; a reduction in the fragmentation of REM sleep; an increase in the amount and percentage of slow-wave (i.e. stage 3 or 4) sleep; an increase in the amount and percentage of stage 2 sleep; a decrease in the number of awakenings, especially in the early morning; an increase in daytime alertness; and increased sleep maintenance. Secondary outcomes which may be provided by the present invention include enhanced cognitive function and increased memory retention. A "method for enhancing the quality of sleep" refers to a method that results in outcomes in a subject which may be correlated to enhancement in sleep quality, including, but not limited to, the outcomes correlated to enhancement of sleep quality as defined above.

The present invention is further useful for the prevention and treatment of sleep disorders and sleep disturbances including sleep problems associated with insomnia, hypersomnia, sleep apnea, narcolepsy, nocturnal myoclonus, REM sleep interruptions, jet-lag, shift workers' sleep disturbances, dysomnias, night terror, night eating syndrome, insomnias associated with depression or with emotional/mood disorders, dysfunctions associated with sleep (parasomnias), as well as sleep walking and enuresis, as well as sleep disorders which accompany aging. Sleep disorders and sleep disturbances are generally characterized by difficulty in initiating or maintaining sleep or in obtaining restful or enough sleep.

In addition, certain drugs may also cause reductions in REM sleep as a side effect and the present invention may be used to correct those types of sleeping disorders as well. The present invention would also be of benefit in the treatment of syndromes such as fibromyalgia which are manifested by non-restorative sleep and muscle pain or sleep apnea which is associated with respiratory disturbances during sleep. It will be clear to one skilled in the art that the present invention is not limited to just sleep disorders and sleep disturbances, but is applicable to a wide variety of conditions which result from a diminished quality of sleep.

The present invention is also concerned with treatment and prevention of these conditions, and with the use of a NPY Y5 antagonist, combinations, and compositions thereof, for the manufacture of a medicament useful for treating or preventing these conditions.

In the present invention, it is preferred that the subject mammal is a human. Although the present invention is applicable both old and young people, it may find greater application in elderly people. Further although the invention may be employed to enhance the sleep of healthy people, it may be especially beneficial for enhancing the sleep quality of people suffering from sleep disorders or sleep disturbances.

The compositions of the present invention may be used in combination with other drugs that may also be useful in the treatment, prevention, or control of disorders, such as hypertension, hypertension associated with obesity, hypertension-related disorders, cardiac hypertrophy, left ventricular hypertrophy, and metabolic syndrome, obesity and obesity-related disorders, for which compounds comprising the compositions are useful. Such other drugs may be administered, by a route and in an amount commonly used therefore, contemporaneously or sequentially with a composition of the present invention. When a composition of the present invention is used contemporaneously with one or more other drugs, a pharmaceutical composition in unit dosage form containing such other drugs and the composition of the present invention is preferred. However, the combination therapy also includes therapies in which the composition of the present invention and one or more other drugs are administered on different overlapping schedules. It is also contemplated that when used in combination with one or more other active ingredients, the composition of the present invention and the other active ingredients may be used in lower doses than when each is used singly. Accordingly, the pharmaceutical compositions of the present invention include those that contain one or more other active ingredients, in addition to a composition of the present invention.

Examples of other active ingredients that may be administered in combination with a composition of the present invention, and either administered separately or in the same pharmaceutical composition, include, but are not limited to:

(a) anti-diabetic agents such as (i) PPARγ agonists such as glitazones (e.g. ciglitazone; darglitazone; englitazone; isaglitazone (MCC-555); pioglitazone; rosiglitazone; troglitazone; BRL49653; CLX-0921; 5-BTZD, and the like), and GW-70207, LG-100641, and LY-300512, and the like; (ii) biguanides such as buformin; metformin; and phenformin, and the like; (iii) protein tyrosine phosphatase-1B (PTP-1B) inhibitors; (iv) sulfonylureas such as acetohexamide; chlorpropamide; diabinese; glibenclamide; glipizide; glyburide; glimepiride; gliclazide; glipentide; gliquidone; glisolamide; tolazamide; and tolbutamide, and the like; (v) meglitinides such as repaglinide, and nateglinide, and the like; (vi) alpha glucoside hydrolase inhibitors such as acarbose; adiposine; camiglibose; emiglitate; miglitol; voglibose; pradimicin-Q; salbostatin; CKD-711; MDL-25,637; MDL-73,945; and MOR14, and the like; (vii) alpha-amylase inhibitors such as tendamistat, trestatin, and Al-3688, and the like; (viii) insulin secretagogues such as linogliride; and A-4166, and the like; (ix) fatty acid oxidation inhibitors, such as clomoxir, and etomoxir, and the like; (x) A2 antagonists, such as midaglizole; isaglidole; deriglidole; idazoxan; earoxan; and fluparoxan, and the like; (xi) insulin or insulin mimetics, such as biota, LP-100, novarapid, insulin detemir, insulin lispro, insulin glargine, insulin zinc suspension (lente and ultralente); Lys-Proinsulin, GLP-1 (73-7) (insulintropin); and GLP-1 (7-36)-NH$_2$), and the like; (xii) non-thiazolidinediones such as JT-501, and farglitazar (GW-2570/GI-262579), and the like; (xiii) PPARα/γ dual agonists such as MK-0767, CLX-0940, GW-1536, GW1929, GW-2433, KRP-297, L-796449, LR-90, and SB 219994, and the like; (xiv) other insulin sensitizing drugs; and (xv) VPAC2 receptor agonists;

(b) lipid lowering agents such as (i) bile acid sequestrants such as, cholestyramine, colesevelem, colestipol, dialkylaminoalkyl derivatives of a cross-linked dextran; Colestid®; LoCholest®; and Questran®, and the like; (ii) HMG-CoA reductase inhibitors such as atorvastatin, itavastatin, fluvastatin, lovastatin, pravastatin, rivastatin, rosuvastatin, simvastatin, and ZD-4522, and the like; (iii) HMG-CoA synthase inhibitors; (iv) cholesterol absorption inhibitors such as stanol esters, beta-sitosterol, sterol glycosides such as tiqueside; and azetidinones such as ezetimibe, and the like; (v) acyl coenzyme A-cholesterol acyl transferase (ACAT) inhibitors such as avasimibe, eflucimibe, KY505, SMP 797, and the like; (vi) CETP inhibitors such as JTT 705, torcetrapib, CP 532,632, BAY63-2149, SC 591, SC 795, and the like; (vii) squalene synthetase inhibitors; (viii) anti-oxidants such as probucol, and the like; (ix) PPARα agonists such as be clofibrate, benzafibrate, ciprofibrate, clofibrate, etofibrate, fenofibrate, gemcabene, and gemfibrozil, GW 7647, BM 170744, LY518674; and other fibric acid derivatives, such as Atromid®, Lopid® and Tricor®, and the like; (x) FXR receptor modulators such as GW 4064, SR 103912, and the like; (xi) LXR receptor such as GW 3965, T9013137, and XTCO179628, and the like; (xii) lipoprotein synthesis inhibitors such as niacin; (xiii) renin angiotensin system inhibitors; (xiv) PPARδ partial agonists; (xv) bile acid reabsorption inhibitors, such as BARI1453, SC435, PHA384640, S8921, AZD7706, and the like; (xvi) PPARδ agonists such as GW501516, and GW590735, and the like; (xvii) triglyceride synthesis inhibitors; (xviii) microsomal triglyceride transport (MTTP) inhibitors, such as inpltapide, LAB687, and CP346086, and the like; (xix) transcription modulators; (xx) squalene epoxidase inhibitors; (xxi) low density lipoprotein (LDL) receptor inducers; (xxii) platelet aggregation inhibitors; (xxiii), 5-LO or FLAP inhibitors; and (xiv) niacin receptor agonists; and (c) anti-hypertensive agents such as (i) diuretics, such as thiazides, including chlorthalidone, chlorothiazide, dichlorophenamide, hydroflumethiazide, indapamide, and hydrochlorothiazide; loop diuretics, such as bumetanide, ethacrynic acid, furosemide, and torsemide; potassium sparing agents, such as amiloride, and triamterene; and aldosterone antagonists, such as spironolactone, epirenone, and the like; (ii) beta-adrenergic blockers such as acebutolol, atenolol, betaxolol, bevantolol, bisoprolol, bopindolol, carteolol, carvedilol, celiprolol, esmolol, indenolol, metaprolol, nadolol, nebivolol, penbutolol, pindolol, propanolol, sotalol, tertatolol, tilisolol, and timolol, and the like; (iii) calcium channel blockers such as amlodipine, aranidipine, azelnidipine, barnidipine, benidipine, bepridil, cinaldipine, clevidipine, diltiazem, efonidipine, felodipine, gallopamil, isradipine, lacidipine, lemildipine, lercanidipine, nicardipine, nifedipine, nilvadipine, nimodepine, nisoldipine, nitrendipine, manidipine, pranidipine, and verapamil, and the like; (iv) angiotensin converting enzyme (ACE) inhibitors such as benazepril; captopril; cilazapril; delapril; enalapril; fosinopril; imidapril; losinopril; moexipril; quinapril; quinaprilat; ramipril; perindopril; perindropril; quanipril; spirapril; tenocapril; trandolapril, and zofenopril, and the like; (v) neutral endopeptidase inhibitors such as omapatrilat, cadoxatril and ecadotril, fosidotril, sampatrilat, AVE7688, ER4030, and the like; (vi) endothelin antagonists such as tezosentan, A308165, and YM62899, and the like; (vii) vasodilators such as hydralazine, clonidine, minoxidil, and nicotinyl alcohol, and the like; (viii) angiotensin II receptor antagonists such as candesartan, eprosartan, irbesartan, losartan, pratosartan, tasosartan, telmisartan, valsartan, and EXP-3137, FI6828K, and RNH6270, and the like; (ix) α/β adrenergic blockers as nipradilol, arotinolol and amosulalol, and the like; (x) alpha 1 blockers, such as terazosin, urapidil, prazosin, bunazosin, trimazosin, doxazosin, naftopidil, indoramin, WHIP 164, and XEN010, and the like; (xi) alpha 2 agonists such as lofexidine, tiamenidine, moxonidine, rilmenidine and guanobenz, and the like; and (xii) aldosterone inhibitors, and the like; and (d) anti-obesity agents, such as (i) 5HT (serotonin) transporter inhibitors, such as paroxetine, fluoxetine, fenfluramine, fluvoxamine, sertraline, and imipramine; (ii) NE (norepinephrine) transporter inhibitors, such as GW 320659, despiramine, talsupram, and nomifensine; (iii) CB-1 (cannabinoind-1-receptor) antagonist/inverse agonists, such as rimonabant (Sanofi Synthelabo), SR-147778 (Sanofi Synthelabo), BAY-65-2520 (Bayer), and SLV 319 (Solvay), and those disclosed in U.S. Pat. Nos. 5,532,237, 4,973,587, 5,013, 837, 5,081,122, 5,112,820, 5,292,736, 5,624,941 and U.S. Pat. No. 6,028,084; and WO 96/33159, WO 98/33765, WO 98/43636, WO 98/43635, WO 01/09120, WO 01.96330, WO 98/31227, WO 98/41519, WO 98/37061, WO 00/10967, WO 00/10968, WO 97/29079, WO 99/02499, WO 01/58869, WO 02/076949, WO 01/64632, WO 01/64633, WO 01/64634, WO 03/006007, and WO 03/007887; and EPO Application No. EP-658546; (iv) ghrelin antagonists, such as those disclosed in WO 01/87335, and WO 02/08250; (v) H3 (histamine H3) antagonist/inverse agonists, such, as thioperamide, 3-(1H-imidazol-4-yl)propyl N-(4-pentenyl)carbamate, clobenpropit, iodophenpropit, imoproxifan, GT2394 (Gliatech), and A331440, and those disclosed in WO 02/15905; and O-[3-(1H-imidazol-4-yl)propanol]carbamates (Kiec-Kononowicz, K. et al., Pharmazie, 55:349-55 (2000)), piperidine-containing histamine H3-receptor antagonists (Lazewska, D. et al., Pharmazie, 56:927-32 (2001), benzophenone derivatives and related compounds (Sasse, A. et al., Arch. Pharm. (Weinheim) 334:45-52 (2001)), substituted N-phenylcarbamates (Reidemeister, S. et al., Pharmazie, 55:83-6 (2000)), and proxifan derivatives (Sasse, A. et al., J. Med. Chem. 43:3335-43 (2000)); (vi) melanin-concentrating hormone 1 receptor (MCH1R) antagonists, such as T-226296 (Takeda), SNP-7941 (Synaptic), and those disclosed in WO 01/82925, WO 01/87834, WO 02/051809, WO 02/06245, WO 02/076929, WO 02/076947, WO 02/04433, WO 02/51809, WO 02/083134, WO 02/0.094799, WO 03/004027, and Japanese Patent Application No. JP13226269; (vii) MCH2R (melanin concentrating hormone 2R) agonist/antagonists; (viii) NPY1 (neuropeptide Y Y1) antagonists, such as BIBP3226, 2-[1-(5-chloro-3-isopropyloxycarbonylaminophenyl)ethylamino ]-6-[2-(5-ethyl-4-methyl-1,3-thiazol-2-yl)ethyl]-4-morpholinopyridine, BIBO 3304, LY-357897, CP-671906, and GI-264879A; and those disclosed in U.S. Pat. No. 6,001,836; and WO 96/14307, WO 01/23387, WO 99/51600, WO 01/85690, WO 01/85098, WO 01/85173, and WO 01/89528; (ix) NPY5 (neuropeptide Y Y5) antagonists, such as L-152,804, GW-569180A, GW-594884A, GW-587081X, GW-548118X; FR 235,208; FR226928, FR 240.662, FR252384; 1229U91, GI-264879A, CGP71683A, LY-377897, LY366377, PD-160170, SR-120562A, SR-120819A, JCF-104, and H409/22; and those compounds disclosed in U.S. Pat. Nos. 6,140,354, 6,191,160, 6,258,837, 6,313,298, 6,337,332, 6,329,395, and 6,340,683; U.S. Pat. Nos. 6,326,375; 6,329,395; 6,337,332; 6,335,345; European Patent Nos. EP-01010691, and EP-01044970; and PCT International Patent Publication Nos. WO 97/19682, WO 97/20820, WO 97/20821, WO 97/20822, WO 97/20823, WO 98/27063, WO 00/107409, WO 00/185714, WO 00/185730, WO 00/64880, WO 00/68197, WO 00/69849, WO 01/09120, WO 01/14376, WO 01/85714, WO 01/85730, WO 01/07469, WO 01/02379, WO 01/02379, WO 01/23388, WO 01/23389, WO 01/44201, WO 01/62737, WO 01/6.2738, WO 01/09120, WO 02/20488, WO 02/22592, WO 02/48152, WO 02/49648 and WO 02/094789; and Norman et al., J. Med. Chem. 43:4288-4312 (2000); (x) leptin, such as recombinant human leptin (PEG-OB, Hoffman La Roche) and recombinant methionyl human leptin (Amgen); (xi) leptin derivatives, such as those disclosed in U.S. Pat. Nos. 5,552,524; 5,552,523; 5,552,522; 5,521,283; and PCT International Publication Nos. WO 96/23513; WO 96/23514; WO 96/23515; WO 96/23516; WO 96/23517; WO 96/23518; WO 96/23519; and WO 96/23520; (xii) opioid antagonists, such as nalmefene (Revex®), 3-methoxynaltrexone, naloxone, and naltrexone; and those disclosed in WO 00/21509; (xiii) orexin antagonists, such as SB-334867-A; and those disclosed in WO 01/96302, WO 01/68609, WO 02/51232, WO 02/51838, and WO 03/023561; (xiv) BRS3 (bombesin receptor subtype 3) agonists; (xv) CCK-A (cholecystokinin-A) agonists, such as AR-R 15849, GI 181771, JMV-180, A-71378, A-71623 and SR146131, and those disclosed in U.S. Pat. No. 5,739,106; (xvi) CNTF (ciliary neurotrophic factors), such as GI-181771 (Glaxo-SmithKline); SR146131 (Sanofi Synthelabo); butabindide; and PD170,292, PD 149164 (Pfizer); (xvii) CNTF derivatives, such as axokine (Regeneron); and WO 94/09134, WO 98/22128, and WO 99/43813; (xviii) GHS (growth hormone secretagogue receptor) agonists, such as NN703, hexarelin, MK-0677, SM-130686, CP-424,391, L-692,429 and L-163,255, and those disclosed in U.S. Pat. No. 6,358, 951, U.S. Patent Application Nos. 2002/049196 and 2002/ 022637; and WO 01/56592, and WO 02/32888; (xix) 5HT2c (serotonin receptor 2c) agonists, such as BVT933, DPCA37215, IK264; PNU 22394; WAY161503, R-1065, and YM 348; and those disclosed in U.S. Pat. No. 3,914,250; and WO 02/36596, WO 02/48124, WO 02/10169, WO 01/66548, WO 02/44152; WO 02/51844, WO 02/40456, and WO 02/40457; (xx) Mc3r (melanocortin 3 receptor) agonists; (xxi) Mc4r (melanocortin 4 receptor) agonists, such as CHIR86036 (Chiron); ME-10142, and ME-10145 (Melacure), and those disclosed in WO 99/64002, WO 00/74679, WO 01/991752, WO 01/74844, WO 01/70708, WO 01/70337, WO 01/91752, WO 02/059095, WO 02/059107, WO 02/059108, WO 02/059117, WO 02/12166, WO 02/11715, WO 02/12178, WO 02/15909, WO 02/068387, WO 02/068388, WO 02/067869, WO 03/007949, and WO 03/009847; (xxii) monoamine reuptake inhibitors, such as sibutratmine (Meridia®/Reductil®) and a salt thereof, and those compounds disclosed in U.S. Pat. Nos. 4,746,680, 4,806,570, and 5,436,272, and U.S. Patent Publication No. 2002/0006964, and WO 01/27068, and WO 01/62341; (xxiii) serotonin reuptake inhibitors, such as dexfenfluramine, fluoxetine, and those in U.S. Pat. No. 6,365,633, and WO 01/27060, and WO 01/162341; (xxiv) GLP-1 (glucagon-like peptide 1) agonists; (xxv) Topiramate (Topimax®); (xxvi) phytopharm compound 57 (CP 644,673); (xxvii) ACC2 (acetyl-CoA carboxylase-2) inhibitors; (xxviii) β3 (beta adrenergic receptor 3) agonists, such as AD9677/TAK677 (Dainippon/Takeda), CL-316,243, SB 418790, BRL-37344, L-796568, BMS-196085, BRL-35135A, CGP12177A, BTA-243, GW 427353, Trecadrine, Zeneca D7114, and SR 59119A, and those disclosed in U.S. Pat. No. 5,705,515, U.S. Pat. No. 5,451,677; and WO 01/74782, and WO 02/32897; (xxix) DGAT1 (diacylglycerol acyltransferase 1) inhibitors; (xxx) DGAT2 (diacylglycerol acyltransferase 2) inhibitors; (xxxi) FAS (fatty acid synthase) inhibitors, such as Cerulenin and C75; (xxxii) PDE (phosphodiesterase) inhibitors, such as theophylline, pentoxifylline, zaprinast, sildenafil, amrinone, milrinone, cilostamide, rolipram, and cilomilast; (xxxiii) thyroid hormone β agonists, such as KB-2611 (KaroBioBMS), and those disclosed in WO 02/15845; and Japanese Patent Application No. JP 2000256190; (xxxiv) UCP-1 (uncoupling protein 1), 2, or 3 activators, such as phytanic acid, 4-[(E)-2-(5,6,7,8-tetrahydro-5,5,8,8-tetramethyl-2-napthalenyl)-1-propenyl]benzoic acid (TTNPB), and retinoic acid; and those disclosed in WO 99/00123; (xxxv) acyl-estrogens, such as oleoyl-estrone, disclosed in del Mar-Grasa, M. et al., Obesity Research, 9:202-9 (2001); (xxxvi) glucocorticoid antagonists; (xxxvii) 11β HSD-1 (11-beta hydroxy steroid dehydrogenase type 1) inhibitors, such as BVT 3498, BVT 2733, and those compounds disclosed in WO 01/90091, WO 01/90090, WO 01/90092; (xxxviii) SCD-1 (stearoyl-CoA desaturase-1) inhibitors; (xxxix) dipeptidyl peptidase IV (DP-IV) inhibitors, such as isoleucine thiazolidide, valine pyrrolidide, NVP-DPP728, LAF237, P93/01, TSL 225, TMC-2A/2B/2C, FE 999011, P9310/K364, VIP 0177, SDZ 274-444; and the compounds disclosed in WO 03/004498, WO 03/004496, EP 1 258 476, WO 02/083128, WO 02/062764, WO 03/000250, WO 03/602530, WO 03/002531, WO 03/002553, WO 03/002593, WO 03/000180, and WO 03/000181; (xxxx) lipase inhibitors, such as tetrahydrolipstatin (orlistat/Xenical®), Triton WR1339, RHC80267, lipstatin, teasaponin, and diethylumbelliferyl phosphate, FL-386, WAY-1218-98, Bay-N-3176, valilactone, esteracin, ebelactone A, ebelactone B, and RHC 80267, and those disclosed in WO 01/77094, and U.S. Pat. Nos. 4,598,089. 4,452,813, 5,512,565, 5,391,571, 5,602,151, 4,405,644, 4,189,438, and 4,242,453; (xxxxi) fatty acid transporter inhibitors; (xxxxii) dicarboxylate transporter inhibitors; (xxxxiii) glucose transporter inhibitors; (xxxxiv) phosphate transporter inhibitors; (xxxxv) melanocortin agonists, such as Melanotan II or those described in WO 99/64002 and WO 00/746799; (xxxxvi) melanin concentrating hormone antagonists; (xxxxvii) galanin antagonists; (xxxxviii) CCK agonists; (xxxxix) corticotropin-releasing hormone agonists; and (xxxxx) phosphodiesterase-3B (PDE3B) inhibitors; and the like.

The above combinations include combinations of a composition of the present invention not only with one other active compound, but also with two or more other active compounds. Non-limiting examples include combinations of the compositions of the present invention with one, two or more active compounds selected from lipid-lowering agents, and anti-hypertensive agents. Combinations of the compositions of the present invention with one, two or more active compounds selected from lipid lowering agents, and anti-diabetic agents are useful to treat, control or prevent metabolic syndrome. In particular, compositions comprising an anti-obesity agent and an anti-hypertensive agent, in addition to an anti-diabetic agent and/or a lipid lowering agent will be useful to synergistically treat, control or prevent metabolic syndrome.

BEST MODE FOR CARRYING OUT THE INVENTION

The following Examples are provided to illustrate the present invention more concretely, but they should not be construed as limiting the invention in any way. The mass spectrum was determined by electron spray ionization (ESI) method.

EXAMPLE 1

Preparation of 4-(2-naphthyl)-2-[3-oxospiro[isobenzofuran-1(3H),4'-piperidin]-1'-yl]-1H-imidazole hydrochloride (1) Preparation of [3-oxospiro[isobenzofuran-1(3H), 4'-piperidin]-1'-yl]carboxamidine hydrochloride To a solution of spiro[isobenzofuran-1(3H),4'-piperidin]-3-one hydrochloride monohydrate (10.0 g, 38.9 mmol) in N,N-dimethylformamide (100 mL) were added 1H-pyrazole-1-carboxamidine hydrochloride (6.0 g, 40.9 mmol) and diisopropylethylamine (14.2 mL, 81.5 mmol), and the mixture was, stirred at room temperature for 19 hours. The reaction solution was concentrated in vacuo. Ethanol and diethyl ether were added to the resulting residue and the precipitates were collected by filtration and dried to obtain the title compound (9.1 g, 78%).

(2) Preparation of 2-tosyloxy-2'-acetonaphthone

Acetonitrile solution (40 mL) containing 2-acetonaphthone (1.70 g, 9.99 mmol) and [hydroxyl(tosyloxy)iodo]benzene (4.00 mg, 10.2 mmol) was heated under reflux for 3 hours. The reaction mixture was cooled, and ethyl acetate was added thereto. The reaction solution was washed with saturated aqueous sodium bicarbonate solution, dried over anhydrous magnesium sulfate, and concentrated in vacuo to remove the solvent to obtain the title compound (2.33 g, 68.5%).

(3) Preparation of 4-(2-naphthyl)-2-[3-oxospiro [isobenzofuran-1(3H),4'-piperidin]-1'-yl]-1H-imidazole hydrochloride (Method 1)

N,N-Dimethylformamide solution (1 mL) containing [3-oxospiro[isobenzofuran-1(3H),4'-piperidin]-1'-yl]carboxamidine hydrochloride (100 mg, 0.355 mmol) and 2-tosyloxy-2'-acetonaphthone (130 mg, 0.382 mmol) was added to potassium carbonate (150 mg, 1.09 mmol), and the mixture was stirred at 100° C. for 10 minutes. The reaction mixture was cooled, ethyl acetate was added thereto, and it was washed with saturated aqueous sodium bicarbonate solution and saturated aqueous brine, dried over anhydrous magnesium sulfate and concentrated in vacuo to remove the solvent. The resulting residue was dissolved in ethyl acetate (20 mL) and to this solution was added 4N hydrochloric acid/ethylacetate (0.5 mL); the mixture was stirred at room temperature for 30 minutes. The resulting precipitates were collected by filtration and dried to obtain the title compound (70.4 mg, 45.9%).

(Method 2)

N,N-dimethylformamide solution (1 mL) containing [3-oxospiro[isobenazofuran-1(3H),4'-piperidin]-1'-yl]carboxamidine hydrochloride (100 mg, 0.355 mmol) and 2-bromo-2'-acetonaphthone (88.4 mg, 0.355 mmol) was added to potassium carbonate (150 mg, 1.09 mmol), and the mixture was stirred at 100° C. for 20 minutes. After the reaction mixture was cooled, ethyl acetate was added thereto. The mixture was washed with saturated aqueous sodium bicarbonate solution and saturated aqueous brine; and the organic layer was dried over anhydrous magnesium sulfate, and then concentrated in vacuo. The resulting residue was dissolved in ethyl acetate (20 mL), and to this solution was added 4N hydrochloric acid/ethyl acetate (0.5 mL). The solution was stirred at room temperature for 30 minutes, and the resulting precipitates were collected by filtration to obtain the title compound (30.2 mg, 19.7%).

$^1$H NMR (300 MHz, DMSO-$d_6$, $\delta$ppm): 1.8-1.9 (2H, m), 2.4-2.6 (2H, m), 3.5-3.7 (2H, m), 4.2-4.4 (2H, m), 7.5-7.7 (3H, m), 7.7-8.0 (7H, m), 8.01 (1H, d, J=8.8 Hz), 8.36 (1H, s), 12.7 (1H, brs), 13.0 (1H, brs); mass spectrum (ESI): 396 (M+H).

The following compounds were prepared according to a method similar to the procedure of Example 1.

EXAMPLE 2

4-(4-bromophenyl)-2-[3-oxospiro[isobenzofuran-1 (3H), 4'-piperidin]-1'-yl]-1H-imidazole hydrochloride $^1$H NMR (300 MHz, DMSO-$d_6$, $\delta$ppm): 1.76-1.87 (2H, m), 2.35-2.49 (2H, m), 3.46-3.60 (2H, m), 4.17-4.29 (2H, m), 7.60-7.82 (8H, m), 7.82 (1H, d, J=7.6 Hz); mass spectrum (ESI): 424, 426 (M+H)

EXAMPLE 3

2-[3-oxospiro[isobenzofuran-1(3H),4'-piperidin]-1'-yl-4-(3-trifluoromethylphenyl)-1H-imidazole $^1$H NMR (3100 MHz, CDCl$_3$, $\delta$ppm): 1.75-1.87 (2H, m), 2.25-2.40 (2H, m), 3.44-3.58 (2H, m), 3.92-4.03 (2H, m), 7.08 (1H, s), 7.33-7.75 (5H, m), 7.80-7.97 (3H, m); mass spectrum (ESI): 414 (M+H)

EXAMPLE 4

4-(4-biphenylyl)-2-[3-oxospiro[isobenzofuran-1(3H),4'-piperidin]-1'-yl]-1H-imidazole hydrochloride $^1$H NMR (300 MHz, DMSO-d$_6$, δppm): 1.79-1.90 (2H, m), 2.38-2.53 (2H, m), 3.49-3.62 (2H, m), 4.20-4.31 (2H, m), 7.36-7.44 (1H, m), 7.46-7.54 (2H, m), 7.60-7.68 (1H, m), 7.70-7.94 (10H, m); mass spectrum (ESI): 422 (M+H)

EXAMPLE 5

4-(3-biphenylyl)-2-[3-oxospiro[isobenzofuran-1(3H),4'-piperidin]-1'-yl]-1H-imidazole hydrochloride $^1$H NMR (300 MHz, DMSO-d$_6$, δppm): 1.73-1.87 (2H, m) 2.33-2.49 (2H, m), 3.36-3.50 (2H, m), 4.13-4.25 (2H, m), 7.36-7.44 (1H, m), 7.47-7.70 (6H, m), 7.72-7.90 (6H, m), 8.07 (1H, s); mass spectrum (ESI): 422 (M+H)

EXAMPLE 6

2-[3-oxospiro[isobenzofuran-1(3H),4'-piperidin]—1'-yl]-4,5-diphenyl-1H-imidazole hydrochloride $^1$H NMR (300 MHz, DMSO-d$_6$, δppm): 1.68-1.80 (2H, m), 2.23-2.40 (2H, m), 3.15-3.28 (2H, m), 4.07-4.18 (2H, m), 7.09-7.20 (1H, m), 7.21-7.52 (9H, m), 7.58-7.66 (1H, m), 7.77-7.88 (3H, m); mass spectrum (ESI): 422 (M+H)

EXAMPLE 7

4-(4-fluorophenyl)-2-[3-oxospiro[isobenzofuran-1(3H),4'-piperidin]-1'-yl]-5-(3-pyridyl)-1H-imidazole hydrochloride $^1$H NMR (300 MHz, DMSO-d$_6$, δppm): 1.70-1.82 (2H, m), 2.26-2.42 (2H, m), 3.17-3.31 (2H, m), 4.07-4.19 (2H, m), 7.13 (1H, t, J=9.2 Hz), 7.21-7.33 (2H, m), 7.36-7.55 (3H, m), 7.59-7.67 (1H, m), 7.72-7.91 (3H, m), 8.32-8.46 (1H, m), 8.67-8.65 (1H, m); mass spectrum (ESI): 441 (M+H)

EXAMPLE 8

4-methyl-2-[3-oxospiro[isobenzofuran-1-(3H),4'-piperidin]-1'-yl]-5-phenyl-1H-imidazole hydrochloride $^1$H NMR (300 MHz, DMSO-d$_6$, δppm): 1.65-1.77 (2H, m), 2.17-2.40 (5H, m), 3.07-3.23 (2H, m), 3.90-4.10 (2H, m), 7.07-7.18 (1H, m), 7.28-7.48 (3H, m), 7.55-7.66 (2H, m), 7.72-7.90 (3H, m); mass spectrum (ESI): 360 (M+H)

EXAMPLE 9

4-(3-methoxyphenyl)-2-[3-oxospiro[isobenzofuran-1(3H),4'-piperidin]-1'-yl]-1H-imidazole hydrochloride $^1$H NMR (300 MHz, CDCl$_3$, δppm): 1.75-1.90 (2H, m), 2.25-2.40 (2H, m), 3.42-3.59 (2H, m), 3.85 (3H, s), 3.91-4.05 (2H, m), 6.76 (1H, dd, J=2.5 Hz, 9.1 Hz), 7.11-7.35 (3H, m), 7.40 (1H, d, J=7.5 Hz), 7.55 (1H, t, J=7.5H z), 7.68 (1H, t, J=7.5 Hz), 7.91 (1H, d, J=7.5 Hz); mass spectrum (ESI): 376 (M+H)

EXAMPLE 10

Preparation of trans-4-(2-naphthyl)-2-[3'-oxospiro[cyclohexane-1,1'(3'H)-isobenzofuran]-4-yl]-1H-imidazole (1) Preparation of trans-N-(2-naphthoylmethyl)-3'-oxospiro[cyclohexane-1,1'(3'H)-isobenzofuran]-4-carboxamide To a solution of trans-3'-oxospiro[cyclohexane-1,1'(3'H)-isobenzofuran]-4-carboxylic acid (123 mf, 0.5 mmol) in chloroform (5 mL) were added 2-amino-2'-acetonaphthone hydrochloride (111 mg, 0.5 mmol), 1-(3-dimethylaminopropyl)-3-ethylcarbodiimide hydrochloride (192 mg, 1 mmol) and triethylamine (0.139 mL, 1 mmol), and the mixture was stirred at room temperature for 18 hours. The reaction solution was distributed using water and ethyl acetate, and the organic layer was dried over anhydrous magnesium sulfate. After removal of the solvent by evaporation in vacuo, the residue was purified by a silica gel column chromatography (hexane:ethyl acetate=2:1 to 1:1) to obtain the title compound (50.7 mg, 76%).

(2) Preparation of trans-4-(2-naphthyl)-2-[3'-oxospiro[cyclohexane-1,1'(3'H)-isobenzofuran]-4-yl]-1H-imidazole To a solution of trans-N-(2-naphthoylmethyl)-3'-oxospiro[cyclohexane-1,1'(3'H)-isobenzofuran]-4-carboxamide (152 mg, 0.37 mmol) in acetic acid (2 ml) was added ammonium acetate (8.48 mg, 11 mmol), and the mixture was stirred at 110° C. for 16 hours. After the reaction solution was cooled, it was concentrated in vacuo, and the residue was neutralized using saturated aqueous sodium bicarbonate solution, and extracted with ethyl acetate. The organic layer was dried over anhydrous magnesium sulfate and concentrated in vacuo to remove the solvent. The residue was purified by a preparative thin layer chromatography (chloroform:ethyl acetate 2:1) to obtain the title compound (49.9 mg, 34%).

$^1$H NMR (300 MHz, CDCl$_3$, δppm): 1.70-1.90 (2H, m), 2.20-2.50 (6H, m), 3.19-3.30 (1H, m), 7.40-7.53 (5H, m), 7.58-7.65 (1H, m), 7.76-7.93 (5H, m), 8.10-8.40 (1H, m); mass spectrum (ESI): 395 (M+H)

The following compounds were prepared according to a method similar to the procedure of Example 10.

EXAMPLE 11 trans-2-[3'-oxospiro[cyclohexane-1,1'(3'H)-isobenzofuran]-4-yl]-4-(3-trifluoromethylphenyl)-1H-imidazole $^1$H NMR (300 MHz, CDCl$_3$, δppm): 1.70-1.90 (2H, m) 2.17-2.60 (6H, m), 3.20-3.30 (1H, m), 7.36 (1H, s), 7.45-7.55 (4H, m), 7.65 (1H, d, J=7.2 Hz), 7.88 (1H, d, J=7.2 Hz), 7.97 (1H, brs), 8.10 (1H, brs); mass spectrum (ESI): 413 (M+H)

EXAMPLE 12 trans-2-(2-naphthyl)-4-[3-oxospiro[6-azaisobenzofuran-1(3H),1'-cyclohexan]-4'-yl]-1H-imidazole (1) Preparation of methyl trans-[3-oxospiro[6-azaisobenzofuran-1(3H),1'-cyclohexan]-4'-yl]ketone To a solution of trans-3-oxospiro[6-azaisobenzofuran-1(3H),1'-cyclohexane]-4'-carboxylic acid (308 mg, 1.2 mmol) in thionyl chloride (2 mL) was added one drop of N,N-dimethylformamide, and the mixture was stirred for 4 hours at reflux under a nitrogen atmosphere. The reaction solution was concentrated in vacuo, and chloroform was added to the residue. The solution was concentrated in vacuo and dried to obtain a crude acid chloride (453 mg). Diethyl ether solution (0.62 mL, 1.9 mmol) containing, 3N methyl magnesium bromide was added dropwise to tetrahydrofuran solution (6 mL) containing the crude acid chloride (226 mg) and copper(I) iodide (118 mg, 0.62 mmol) at −78° C. over 30 minutes under a nitrogen atmosphere, and then the temperature was raised to 0° C., and the mixture was stirred for one hour. Saturated aqueous ammonium chloride solution was added to the reaction solution, followed by extraction with chloroform. After the organic layer was washed successively with saturated aqueous ammonium chloride, saturated aqueous sodium carbonate and saturated brine, it was dried over anhydrous magnesium sulfate. The residue obtained by evaporation of the solvent in vacuo was purified by a silica gel column chromatography (C-300, ethyl acetate:hexane=2:1) to obtain the title compound (119 mg, 78% yield of two steps).

(2) Preparation of bromomethyl trans-[3-oxospiro[6-azaisobenzofuran-1(3H),1'-cyclohexan]-4'-yl]ketone To a solution of methyl trans-[3-oxospiro[6-azaisobenzofuran-1(3H),1'-cyclohexan]-4'-yl]ketone (50 mg, 0.20 mmol) in methanol (2 mL) was added dioxane bromide (76 mg, 0.31 mmol), and the mixture was stirred at room temperature for 15 hours under a nitrogen atmosphere. The reaction solution was diluted with ethyl acetate, washed with water and aqueous sodium sulfite, and dried over anhydrous magnesium sulfate. The solvent was removed by evaporation in vacuo to obtain the title compound (75 mg). The product was used in the subsequent step without further purification.

(3) Preparation of trans-2-(2-naphthyl)-4-[3-oxospiro[6-azaisobenzofuran-1(3H),1'-cyclohexan]-4'-yl]-1H-imidazole Potassium carbonate, (21 mg, 0.16 mmol) was added to dioxane solution (0.77 mL) containing 2-naphthamidine (18 mg, 0.077 mmol) and bromomethyl trans-[3-oxospiro[6-azaisobenzofuran-1(3H),1'-cyclohexan]-4'-yl]ketone (25 mg), and the mixture was stirred at room temperature for 45 minutes under a nitrogen atmosphere, and at 100° C. for further 2 hours. The reaction solution was cooled to room temperature, diluted with ethyl acetate, and washed with water and saturated brine. After the solution was dried over anhydrous magnesium sulfate, it was concentrated in vacuo to remove the solvent, and the resulting residue was purified by a silica gel column chromatography (C-300, ethyl acetate:hexane=2:1) and a preparative thin layer chromatography (ethyl acetate:hexane=2:1) to obtain the title compound (6.4 mg, 21%).

$^1$H NMR (400 MHz, CD$_3$OD, δppm): 2.05-2.20 (4H, m), 2.21-2.40 (4H, m), 3.08-3.20 (1H, m), 7.16 (1H, s), 7.46-7.54 (2H, m), 7.83-7.89 (2H, m), 7.90-7.96 (2H, m), 7.99-8.04 (1H, m), 8.34 (1H, s), 8.83 (1H, d, J=4.8 Hz), 9.17 (1H, s); mass spectrum (ESI): 396 (M+H)

EXAMPLE 13

Preparation of 3-[3-oxospiro[isobenzofuran-1(3H),4'-piperidin]-1'-yl]-5-(3-trifluoromethylphenyl)-1H-pyrazole (1) Preparation of 3,3-bis(methylthio)-1-(3-trifluoromethylphenyl)-2-propen-1-one Potassium t-butoxide (6.56 g, 58.5 mmol) was added to tetrahydrofuran solution (60 mL) containing 3'-(trifluoromethyl)acetophenone (5.00 g, 26.6 mmol) and carbon disulfide (3.52 mL, 58.5 mmol) at 0° C., and the mixture was stirred at room temperature for 30 minutes under a nitrogen atmosphere. After that, iodomethane, (8.27 mL, 133 mmol) was added thereto, and the mixture was stirred at room temperature for 30 minutes under a nitrogen atmosphere. After water was added thereto, the solution was extracted with ethyl acetate. The organic layer was washed with saturated aqueous ammonium chloride solution and saturated brine, dried over anhydrous sodium sulfate and concentrated in vacuo. The residue was separated and purified by a silica gel column chromatography (Biotage, Si+40M, hexane:ethyl acetate=7:1) to obtain the title compound (3.27 g, 42%).

(2) Preparation of 3-[3-oxospiro[isobenzofuran-1(3H),4'-piperidin]-1'-yl]-5-(3-trifluoromethylphenyl)-1H-pyrazole Triethylamine (0.10 mL, 0.72 mmol) was added to ethanol solution (5.0 mL) of 3,3-bis(methylthio)-1-(3-trifluoromethylphenyl)-2-propen-1-one (200 mg, 0.68 mmol) and 3-oxospiro[isobenzofuran-1(3H),4'-piperidine]monohydrate hydrochloride (177 mg, 0.69 mmol), and the mixture was stirred at 80° C. for 24 hours under a nitrogen atmosphere. After that, hydrazine monohydrate (0.083 mL, 1.7 mmol) was added thereto, the mixture was stirred at 80° C. for 6 hours. The reaction mixture was concentrated, and water was added thereto, followed by extraction with ethyl acetate. The organic layer was washed with saturated brine, dried over anhydrous sodium sulfate and concentrated in vacuo. The residue was separated and purified by a silica gel column chromatography (Biotage, Si+12M, hexane:ethyl acetate=1:1) to obtain the title compound (86 mg, 30%).

$^1$H NMR (400 MHz, CDCl$_3$, δppm): 1.75-1.84 (2H, m), 2.31 (2H, dt, J=13.2 Hz, 4.8 Hz), 3.38 (2H, dt, J=12.8 Hz, 2.2 Hz), 3.76-3.84 (2H, m), 6.07 (1H, s), 7.39 (1H, d, J=7.3 Hz), 7.46-7.60 (3H, m), 7.62-7.71 (1H, m), 7.76 (1H, d, J=7.7 Hz), 7.83 (1H, s), 7.90 (1H, d, J=7.7 Hz); mass spectrum (ESI): 414.1 (M+H)

The following compounds were prepared according to a method similar to the procedure of Example 13.

EXAMPLE 14

3-[3-oxospiro[isobenzofuran-1(3H),4'-piperidin]-1'-yl]-5-(2-phenylpyridin-4-yl)-1H-pyrazole $^1$H NMR (400 MHz, DMSO-d$_6$, δppm): 1.70-1.82 (2H, m), 2.30-2.45 (2H, m), 3.04-3.20 (2H, m), 3.65-3.93 (2H, m), 6.38-6.75 (1H, m), 7.41-7.56 (3H, m), 7.58-7.70 (2H, m), 7.74-7.80 (2H, m), 7.84 (1H, d, J=7.3 Hz), 8.14 (1H, d, J=7.3 Hz), 8.26 (1H, brs), 8.66 (1H, brs); mass spectrum (ESI): 423.1 (M+H)

EXAMPLE 15

3-(3-biphenylyl)-5-[3-oxospiro[isobenzofuran-1(3H),4'-piperidin]1'-yl]-1H-pyrazole $^1$H NMR (400 MHz, CDCl$_3$, δppm): 1.72-1.75 (2H, m), 2.25-2.34 (2H, m), 3.35-3.41 (2H, m), 3.82-4.13 (2H, m), 6.10 (1H, s), 7.32-7.67 (11H, m), 7.89 (1H, s), 7.90 (1H, d, J=7.3 Hz); mass spectrum (ESI): 422.2 (M+H)

EXAMPLE 16

3-(3-bromophenyl)-5-[3-oxospiro[isobenzofuran-1(3H),4'-piperidin]-1'-yl]-1H-pyrazole $^1$H NMR (400 MHz, CDCl$_3$, δppm): 1.74-1.84 (2H, m) 2.32 (2H, dt, J=13.3 Hz, 4.8 Hz), 3.39 (2H, dt, J=12.7 Hz, 2.6 Hz), 3.75-3.86 (2H, m), 6.05 (1H, s), 7.30 (1H, d, J=7.9 Hz), 7.41 (1H, d, J=7.6 Hz), 7.43-7.58 (3H, m), 7.64-7.77 (2H, m), 7.91 (1H, dd, J=7.6 Hz, 1.0 Hz); mass spectrum (ESI): 424.1/426.1

EXAMPLE 17

3-(3-biphenylyl)-5-[3-oxospiro[6-azaisobenzofuran-1(3H),4'-piperidin]-1'-yl]-1H-pyrazole $^1$H NMR (400 MHz, DMSO-d$_6$, δppm): 1.80-1.95 (2H, m), 2.38-2.52 (2H, m), 3.00-3.16 (2H, m), 3.76-3.91 (2H, m), 6.44 (1H, s), 7.36-7.40 (1H, m), 7.43-7.56 (3H, m), 7.57-7.78 (4H, m), 7.83 (1H, d, J=5.1 Hz), 8.01 (1H, s), 8.86 (1H, d, J=5.1 Hz), 9.17 (1H, s); mass spectrum (ESI): 423.1 (M+H)

EXAMPLE 18

3-[3-oxospiro[6-azaisobenzofuran-1(3H),4'-piperidin]-1'-yl]-5-(2-phenylpyridin-4-yl)-1H-pyrazole $^1$H NMR (400 MHz, DMSO-d$_6$, δppm) 1.82-1.96 (2H, m), 2.39-2.55 (2H, m), 3.03-3.20 (2H, m), 3.65-3.92 (2H, m), 6.40-6.79 (1H, m), 7.42-7.56 (3H, m), 7.63 (1H, brs), 7.84 (1H, dd, J=5.1 Hz, 1.1 Hz), 8.14 (2H, d, J=7.7 Hz), 8.26 (1H, brs), 8.66 (1H, brs), 8.86 (1H, d, J=4.8 Hz), 9.18 (1H, s) ;mass spectrum (ESI): 424.1 (M+H)

EXAMPLE 19

3-[3-oxospiro[isobenzofuran-1(3H),4'-piperidin]-1'-yl]-5-(2-phenylpyrimidin-4-yl)-1H-pyrazole $^1$H NMR (400 MHz, CDCl$_3$, δppm): 1.78-1.88 (2H, m), 2.35 (2H, dt, J=4.4 Hz, 13.2 Hz), 3.36-3.48 (2H, m), 6.37 (1H, s), 7.35-7.43 (2H, m), 7.48-7.58 (4H, m), 7.67 (1H, t, J=7.3 Hz), 7.91 (1H, d, J=7.7 Hz), 8.44-8.52 (2H, m), 8.83 (1H, d, J=4.8 Hz); mass spectrum (ESI): 424

EXAMPLE 20

Preparation of trans-3-(3-biphenylyl)-5-[3'-oxospiro[cyclohexane-1,1'(3H)-isobenzofuran]-4-yl]-1H-pyrazole (1) Preparation of trans-3'-oxospiro[cyclohexane-1,1'(3'H)-isobenzofuran]-4-carboxylic acid imidazolide To a solution of trans-3'-oxospiro[cyclohexane-1,1'(3'H)-isobenzofuran-4-carboxylic acid (1.00 g, 4.06 mmol) in tetrahydrofuran (25 mL) was added N,N'-dicarbonyldiimidazole (858 mg, 4.47 mmol), and the mixture was stirred at room temperature for 20 hours under a nitrogen atmosphere. The resulting solid was collected by filtration, washed with tetrahydrofuran, and dried to obtain the title compound (808 mg, 67%).

(2) Preparation of trans-3-(3-biphenylyl)-5-[3'-oxospiro[cyclohexane-1,1'(3'H)-isobenzofuran]-4-yl]-1H-pyrazole To a solution of 3'-phenylacetophenone (100 mg, 0.51 mmol) in tetrahydrofuran (3.0 mL) was added 1.0 M hexane solution (0.51 mL, 0.51 mmol) containing lithium hexamethyldisilazide at −78° C. After that, the mixture was stirred at −78° C. for 5 minutes under a nitrogen atmosphere. Trans-3'-oxospiro[cyclohexane-1,1'(3'H)-isobenzofuran]-4-carboxylic acid imidazolide (151 mg, 0.51 mmol) was added thereto, and then the mixture was stirred at room temperature for 1.5 hours under a nitrogen atmosphere. After saturated aqueous ammonium chloride solution was added thereto, the reaction solution was extracted with ethyl acetate. The organic layer was washed with saturated brine, dried over anhydrous sodium sulfate and concentrated in vacuo. The residue was dissolved in ethanol (4.0 mL), and hydrazine monohydrate (0.037 mL, 1.5 mmol) was added thereto; the mixture was stirred at room temperature for 15 hours. After the reaction solution was concentrated in vacuo, the residue was separated and purified by a silica gel column chromatography (Biotage, Si+25M, hexane:ethyl acetate=2:1 to 1:1) to give the title compound (13.2 mg, 62%).

$^1$H NMR (400 MHz, CDCl$_3$, δppm): 1.75-1.83 (2H, m), 1.95-2.10 (2H, m), 2.14-2.23 (2H, m), 2.25-2438 (2H, m), 3.10-3.18 (1H, m), 6.56 (1H, s), 7.26-7.60 (10H, m), 7.70 (1H, d, J=7.3 Hz), 7.86 (1H, d, J=7.3 Hz), 7.98 (1H, s); mass spectrum (ESI): 421.1 (M+H)

The following compounds were prepared according to a method similar to the procedure of Example 20.

EXAMPLE 21 trans-3-[3'-oxospiro[cyclohexane-1,1'(3'H)-isobenzofuran]-4-yl]-5-(2-phenylpyridin-4-yl)-1H-pyrazole $^1$H NMR (400 MHz, CDCl$_3$, δppm): 1.81-1.93 (2H, m), 1.98-2.10 (2H, m), 2.15-2.25 (2H, m), 2.31-2.43 (2H, m)-3.19-3.28 (2H, m), 6.69 (1H, s), 7.35-7.53 (5H, m), 7.56-7.63 (2H, m), 7.89 (1H, d, J=7.3 Hz), 7.96-8.05 (2H, m), 8.12 (1H, s), 8.72 (1H, d, J=5.1 Hz); mass spectrum (ESI): 422.2 (M+H)

EXAMPLE 22 trans-3-[3'-oxospiro[cyclohexane-1,1'(3'H)-isobenzofuran]-4-yl]-5-(1-phenylpyrazol-3-yl)-1H-pyrazole $^1$H NMR (400 MHz, CDCl$_3$, δppm): 1.80-1.93 (2H, m), 3.03-2.18 (2H, m), 2.19-2.30 (2H, m), 2.31-2.42 (2H, m), 6.61 (1H, s), 6.79 (1H, d, J=2.2 Hz), 6.79 (1H, d, J=2.2 Hz), 7.26-7.35 (1H, m), 7.38-7.53 (4H, m), 7.55-7.62 (1H, m), 7.73 (1H, d, J=8.8 Hz), 7.87 (1H, d, J=7.7 Hz), 7.95 (1H, d, J=2.2 Hz); mass spectrum (ESI): 411.2 (M+H)

EXAMPLE 23 trans-3-[3'-oxospiro[cyclohexane-1,1'(3'H)-isobenzofuran]-4-yl]-5-(2-phenylpyrimidin-4-yl)-1H-pyrazole $^1$H NMR (400 MHz, CDCl$_3$, δppm): 1.82-1.93 (2H, m), 2.06-2.17 (2H, m), 2.20-2.32 (2H, m), 2.33-2.42 (2H, m), 3.21-3.26 (1H, m), 6.91 (1H, s), 7.40 (1H, d, J=7.7 Hz), 7.4.5-7.52 (4H, m), 7.55-7.60 (2H, m), 7.85-7.89 (1H, m), 8.46-8.51 (2H, m), 8.82 (1H, d, J=5.1 Hz); mass spectrum (ESI): 423.1 (M+H)

EXAMPLE 24 trans-3-[3'-oxospiro[cyclohexane-1,1'(3'H)-isobenzofuran]-4-yl]-5-(6-phenylpyrazin-2-yl)-1H-pyrazole $^1$H NMR (400 MHz, CDCl$_3$, δppm): 1.86-1.92 (2H, m), 2.10-2.18 (2H, m) 2.23-2.31 (2H, m), 2.36-2.44 (2H, m), 3.23-3.30 (1H, m), 6.88 (1H, s), 7.43 (1H, d, J=7.7 Hz), 7.47-7.62 (5H, m), 7.88 (1H, d, J=7.7 Hz), 8.06-7.10 (2H, m), 8.95 (1H, s), 8.97 (1H, s); mass spectrum (ESI): 423.1 (M+H)

EXAMPLE 25 trans-3-(3-chlorophenyl)-5-[3'-oxospiro[cyclohexane-1,1'(3'H)-isobenzofuran]-4-yl]-1H-pyrazole $^1$H NMR (400 MHz, CDCl$_3$, δppm): 1.80-1.94 (2H, m), 1.98-2.12 (2H, m), 2.13-2.28 (2H, m), 2.30-2.47 (2H, m), 3.16-3.28 (1H, m), 6.53 (1H, s), 7.25-7.43 (3H, m), 7.46-7.68 (3H, m), 7.76 (1H, s), 7.90 (1H, d, J=7.5 Hz); mass spectrum (ESI): 379.1/381.1 (M+H)

EXAMPLE 26 trans-3-[3'-oxospiro[cyclohexane-1,1'(3'H)-isobenzofuran]-4-yl]-5-(2-quinolyl)-1H-pyrazole $^1$H NMR (400 MHz, CDCl$_3$, δppm): 1.83-1.94 (2H, m), 2.10-2.21 (2H, m), 2.24-2.44 (4H, m), 3.22-3.30 (1H, m), 6.85 (1H, s), 7.42-7.62 (4H, m), 7.70-7.76 (1H, m), 7.80-7.90 (3H, m)-18.10 (1H, d, J=8.4 Hz), 8.21 (1H, d, J=8.4 Hz); mass spectrum (ESI): 396.0 (M+H)

EXAMPLE 27 trans-3-(3-biphenylyl)-5-[3-oxospiro[6-azaisobenzofuran-1(3H),1'-cyclohexan]-4'-yl]-1H-pyrazole $^1$H NMR (400 MHz, CDCl$_3$, δppm): 1.78-1.88 (2H, m), 1.90-2.03 (2H, m), 2.05-2.31 (4H, m), 3.01-3.14 (1H, m), 6.54 (1H, s), 7.26-7.45 (4H, m), 7.46-7.56 (3H, m), 7.60-7.78 (2H, m), 7.92 (1H, s), 8.78 (1H, d, J=5.1 Hz), 8.82 (1H, s); mass spectrum (ESI): 422.2 (M+H)

EXAMPLE 28 trans-3-(3-biphenylyl)-5-[3-oxospiro[5-azaisobenzofuran-1(3H),1'-cyclohexan]-4'-yl]-1H-pyrazole $^1$H NMR (400 MHz, CDCl$_3$, δppm): 1.85-1.97 (2H, m), 2.06-2.17 (2H, m), 2.18-2.38 (2H, m), 2.34-2.43 (2H, m), 3.20-3.28 (1H, m), 6.55 (1H, s), 7.35-7.55 (5H, m), 7.58-7.70 (4H, m), 7.79 (1H, s), 8.78 (1H, d, J=5.1 Hz), 9.15 (1H, d, J=1.1 Hz); mass spectrum (ESI): 422.2 (M+H)

EXAMPLE 29 trans-3-[3-oxospiro[6-azaisobenzofuran-1(3H),1'-cyclohexan]-4'-yl]-5-(2-phenylpyrimidin-4-yl)-1H-pyrazole $^1$H NMR (400 MHz, CDCl$_3$, δppm): 1.92-2.05 (2H, m), 2.16-2.31 (4H, m), 2.35-2.45 (2H, m), 3.21-3.30 (1H, m), 6.88 (1H, s), 7.49-7.55 (4H, m), 7.76-7.79 (1H, m), 8.47-8.53 (2H, m), 8.85 (2H, d, J=5.1 Hz), 8.95 (1H, s); mass spectrum (ESI): 424.1 (M+H)

EXAMPLE 30

3-(2-naphthyl)-5-[3-oxospiro[isobenzofuran-1-(3H),4'-piperidin]-1'-yl]-1H-1,2,4-triazole (1) Preparation of [3-oxospiro[isobenzofuran-1(3H),4'-piperidin]-1'-yl]carbonitrile To a solution of spiro[isobenzofuran-1(3H),4'-piperidin]-3-one hydrochloride monohydrate (1.50 g, 6.26 mmol) in N,N-dimethylformamide (30 mL) were added cyanogen bromide (800 mg, 7.22 mmol) and triethylamine (1.92 mL, 13.8 mmol), and the mixture was stirred overnight at room temperature. The reaction solution was diluted with ethyl acetate and washed with water and saturated brine. The organic layer was dried over anhydrous sodium sulfate, and concentrated in vacuo to obtain the title compound (1.32 g, 92%) as a colorless solid.

(2) Preparation of 3-(2-naphthyl)-5-[3-oxospiro[isobenzofuran-1(3H),4'-piperidin]-1'-yl]-1H-1,2,4-triazole Ytterbium triflate (30 mg, 0.043 mmol) was added to toluene solution (0.5 mL) containing 2-naphthalenecarboxylic acid hydrazide (30 mg, 0.16 mmol) and [3-oxospiro[isobenzofuran-1(3H),4'-piperidin]-1'-yl]carbonitrile (30 mg, 0.13 mmol), and the mixture was stirred at 140° C. for 11 hours in a sealed tube. After saturated aqueous sodium bicarbonate solution was added to the reaction solution, the solution was extracted with ethyl acetate. The organic layer was dried over anhydrous sodium sulfate and concentrated in vacuo. The residue was separated and purified by a silica gel column chromatography (Biotage 12M, chloroform:methanol=40:1) to obtain the title compound (20 mg, 38%) as a colorless solid.

$^1$H NMR (400 MHz, DMSO-d$_6$, δppm): 1.60-1.86 (2H, m), 2.22-2.68 (2H, m), 3.12-3.60 (2H, m), 4.02-4.22 (2H, m), 7.42-8.20 (11H, m); mass spectrum (ESI): 397 (M+H)

The following compounds were prepared according to a method similar to the procedure of Example 30.

EXAMPLE 31

3-[3-oxospiro[isobenzofuran-1(3H),4'-piperidin]-1'-yl]-5-(3-trifluoromethylphenyl)-1H-1,2,4-triazole $^1$H NMR (300 MHz, DMSO-d$_6$, δppm): 1.67-1.82 (2H, m), 2.25-2.43 (2H, m), 3.14-3.45 (2H, m), 4.05-4.20 (2H, m), 7.59-7.93 (6H, m), 8.15-8.30 (2H, m), 12.94 (0.85H, s), 13.83 (0.15H, s); mass spectrum (ESI): 415 (M+H)

EXAMPLE 32

Preparation of trans-6-(4-fluorophenyl)-2-[3-oxospiro[6-azaisobenzofuran-1(3H),1'-cyclohexan]-4'-yl]-1-H-pyrazolo[2,3-b][1,2,4]triazole and cis-6-(4-fluorophenyl)-2-[3-oxospiro[6-azaisobenzofuran-1(3H),1'-cyclohexan]-4'-yl]-1H-pyrazolo[2,3-b][1,2,4]triazole

(1) Preparation of 1,5-diamino-3-(4-fluorophenyl)-1H-pyrazole

Hydroxylamine-O-sulfonic acid (2.26 g, 20-0 nmol) was portionwise added to aqueous solution, (100 mL) containing 5-amino-3-(4-fluorophenyl)-1H-pyrazole (2.0 g, 11.3 mmol) and potassium hydroxide (2.52 g, 45 mmol) while stirring at 80° C. After the mixture was stirred at 80° C. for 30 minutes, potassium hydroxide (2.52 g, 45 mmol) was added thereto, hydroxylamine-O-sulfonic acid (2.26 g, 20.0 mmol) was portionwise added, and the mixture was stirred for further 1 hour. The reaction solution was cooled down to room temperature, and extracted with ethyl acetate. The organic layer was washed with saturated brine, dried over anhydrous potassium carbonate, and concentrated in vacuo. The residue was purified by a silica gel column chromatography (C-300, hexane:ethyl acetate=1:2) to obtain the title compound (324 mg, 14.9%).

(2) Preparation of trans-N-[(1-amino-3-(4-fluorophenyl)-1H-pyrazol-5-yl]-3-oxospiro[6-azaisobenzofuran-1(3H),1-cyclohexane]-4'-carboxamide and trans-N-[5-amino-3-(4-fluorophenyl)-1H-pyrazol-1-yl]-3-oxospiro[6-azaisobenzofuran-1(3H),1'-cyclohexane]-4'-carboxamide 3-Ethyl-1-(3-dimethylaminopropyl)carbodiimide hydrochloride (220 mg, 1.17 mmol) was added to pyridine, solution (2 mL) containing trans-3-oxospiro[6-azaisobenzofuran-1(3H),1'-cyclohexane]-4'-carboxylic acid (247 mg, 1.0 mmol) and 1,5-diamino-3-(4-fluorophenyl)-1H-pyrazole (192 mg, 1.0 mmol), and the mixture was stirred overnight at room temperature under a nitrogen atmosphere. The reaction solution was diluted with ethyl acetate, and washed with water and saturated brine. The organic layer was dried over anhydrous magnesium sulfate and concentrated in vacuo. The residue was separated and purified by a silica gel column chromatography (C-300, methanol:chloroform=1:50 to 1:20) to obtain the title compounds (137 mg, 32.6% and 107 mg, 25.5%, respectively).

(3) Preparation of trans-6-(4-fluorophenyl)-2-[3-oxospiro[6-azaisobenzofuran-1(3H),1'-cyclohexan]-4'-yl]-1H-pyrazolo[2,3-b][1,2,4]triazole and cis-6-(4-fluorophenyl)-2-[3-oxospiro[6-azaisobenzofuran-1(3H),1'-cyclohexan]-4'-yl]-1H-pyrazolo[2,3-b][1,2,4]triazole Trans-N-[5-amino-3-(4-fluorophenyl)-1H-pyrazol-1-yl]-3-oxospiro[6-azaisobenzofuran-1(3H),1'-cyclohexan]-4'-carboxamide (101 mg, 0.24 mmol) was suspended in phosphorous oxychloride (1 mL), and the suspension was stirred overnight at 100° C. The reaction solution was cooled down to room temperature and poured portionwise into water. After the solution was adjusted to pH 7 with saturated aqueous sodium bicarbonate solution, it was extracted with ethyl acetate. The organic layer was washed with saturated brine, dried over anhydrous magnesium sulfate and concentrated in vacuo. The residue was separated and purified by silica gel column chromatography (C-300, methanol:chloroform=1:100 to 1:10, and C-300, hexane:ethyl acetate=2:1 to ethyl acetate alone) to obtain the title compound (18.3 mg, 18.9% and 7.4 mg, 7.6%, respectively) as a white solid.

Trans Form:
$^1$H NMR (300 MHz, DMSO-$d_6$, δppm): 1.9-2.1 (2H, m), 2.1-2.3 (6H, m), 3.2-3.4 (1H, m), 6.32 (1H, s), 7.23 (2H, t, J=8.9 Hz), 7.8-7.9 (3H, m), 8.88 (1H, d, J=5.0 Hz), 9.23 (1H, s), 12.74 (1H, s); mass spectrum (ESI): 404 (M+H)

Cis Form:
$^1$H NMR (300 MHz, DMSO-$d_6$, δppm): 1.84-1.95 (2H, m), 1.96-2.09 (2H, m), 2.1-2.2 (2H, m), 2.29-2.43 (2H, m), 3.05-3.18 (1H, m), 6.27 (1H, s), 7.21 (2H, t, J=8.9 Hz), 7.8-7.9 (3H, m), 8.88 (1H, d, J=5.0 Hz), 9.16 (1H, s), 12.75 (1H, brs); mass spectrum (ESI): 404 (M+H)

EXAMPLE 33

Preparation of trans-6-(3-fluorophenyl)-2-[3-oxospiro[6-azaisobenzofuran-1(3H),1'-cyclohexan]-4'-yl]-1H-pyrazolo[2,3-b][1, 2-14]triazole and cis-6-(3-fluorophenyl)-2-[3-oxospiro[6-azaisobenzofuran-1(3H),1'-cyclohexan]-4'-yl]-1H-pyrazolo[2,3-b][1,2,4]triazole The title compounds were prepared according to a method similar to the procedure of Example 32(3), using trans-N-[1-amino-3-(3-fluorophenyl)-1H-pyrazol-5-yl]-3-oxospiro[6-azaisobenzofuran-1(3H),1'-cyclohexane]-4'-carboxamide which had been, synthesized according to a method similar to the method of Examples 32(1) and 32(2).

Trans Form:
$^1$H NMR (300 MHz, DMSO-$d_6$, δppm): 1.95-2.05 (2H, m), 2.1-2.4 (6H, m), 3.2-3.4 (1H, m), 6.42 (1H, s), 7.05-7.15 (1H, m), 7.4-7.5 (1H, m), 7.6-7.7 (1H, m), 7.71 (1H, d, J=7.7 Hz), 7.85 (1H, d, J=5.0 Hz), 8.88 (1H, d, J=5.0 Hz), 9.23 (1H, s), 12.80 (1H, brs); mass spectrum (ESI): 404 (M+H)

Cis Form:
$^1$H NMR (300 MHz, DMSO-$d_6$, δppm): 1.84-1.96 (2H, m), 1.96-2.09 (2H, m), 2.1-2.2 (2H, m), 2.29-2.43 (2H, m), 3.05-3.18 (1H, m), 6.38 (1H, s), 7.05-7.15 (1H, m), 7.38-7.48 (1H, m), 7.58-7.65 (1H, m), 7.69 (1H, d, J=7.9 Hz), 7.84 (1H, d, J=5.0 Hz), 8.88 (1H, d, J=5.0 Hz), 9.16 (1H, s), 12.8 (1H, brs); mass spectrum (ESI): 404 (M+H)

The following compounds were prepared according to a method similar to the method of Example 32 or 33.

EXAMPLE 34 trans-6-(2-fluorophenyl)-2-[3-oxospiro[6-azaisobenzofuran-1(3H),1'-cyclohexan]-4'-yl]-1H-pyrazolo[2, 3-b][1,2,4]-triazole $^1$H NMR (300 MHz, DMSO-$d_6$, δppm): 1.95-2.05 (2H, m), 2.1-2.4 (6H, m), 3.2-3.4 (1H, m), 6.21 (1H, d, J=3.9 Hz), 7.2-7.4 (3H, m), 7.86 (1H, d, J=5.1 Hz), 7.9-8.1 (1H, m), 8.88 (1H, d, J=5.1 Hz), 9.23 (1H, s), 12.8 (1H, br s); mass spectrum (ESI): 404 (M+H)

EXAMPLE 35 trans-2-[3-oxospiro[6-azaisobenzofuran-1(3H),1'-cyclohexan]-4'-yl]-6-phenyl-1H-pyrazolo[2,3-b][1,2,4]triazole $^1$H NMR (300 MHz, DMSO-$d_6$, δppm): 1.95-2.05 (2H, m), 2.1-2.4 (6H, m), 3.2-3.4 (1H, m), 6.32 (1H, s), 7.25-7.35 (1H, m), 7.35-7.45 (2H, m), 7.8-7.9 (3H, m), 8.88 (1H, d, J=5.0 Hz), 9.23 (1H, s), 12.7 (1H, brs); mass spectrum (ESI): 386 (M+H)

EXAMPLE 36 trans-2-[3'-oxospiro[cyclohexane-1,1'(3'H)-isobenzofuran]-4-yl]-6-phenyl-1H-pyrazolo[2,3-b][1,2,4]triazole $^1$H NMR (300 MHz, DMSO-$d_6$, δppm): 1.75-1.95 (2H, m), 2.1-2.4 (6H, m), 3.2-3.4 (1H, m), 6.31 (1H, s), 7.25-7.35 (1H, m), 7.35-7.45 (2H, m), 7.55-7.65 (1H, m), 7.7-7.8 (2H, m), 7.8-7.9 (3H, m), 12.7 (1H, brs); mass spectrum (ESI): 385 (M+H).

EXAMPLE 37 cis-2-[3'-oxospiro[cyclohexane-1,1'(3'-H)-isobenzofuran]-4-yl]-6-phenyl-1H-pyrazolo[2,3-b][1,2,4]triazole $^1$H NMR (300 MHz, DMSO-$d_6$, δppm): 1.75-1.85 (2H, m), 1.96-2.2 (4H, m), 2.2-2.4 (2H, m), 3.0-3.2 (1H, m), 6.27 (1H, s), 7.2-7.3 (1H, m), 7.3-7.4 (2H, m), 7.55-7.65 (1H, m), 7.7-7.9 (5H, m), 12.7 (1H, brs); mass spectrum (ESI): 385 (M+H)

EXAMPLE 38 trans-2-[3'-oxospiro[cyclohexane-1,1'(3'H)-isobenzofuran]-4-yl]-5-phenyl-1H-imidazo[1,2-b][1,2,4]triazole $^1$H NMR (300 MHz, DMSO-$d_6$, δppm): 1.7-1.8 (2H, m), 2.1-2.4 (6H, m), 3.15-3.25 (1H, m), 7.29-7.37 (1H, m), 7.4-7.5 (2H, m), 7.55-7.65 (2H, m), 7.7-7.8 (3H, m), 7.80-7.86 (3H, m), 8.16 (1H, s), 12.3 (1H, brs); mass spectrum (ESI): 385 (M+H)

EXAMPLE 39 trans-2-[3'-oxospiro[cyclohexane-1,1'(3'H)-isobenzofuran]-4-yl]-6-phenyl-1H-[1,2,4]triazolo[2,3-b][1,2,4]triazole $^1$H NMR (300 MHz, DMSO-$d_6$, δppm): 1.6-1.85 (2H, m), 2.1-2.4 (6H, m), 3.1-3.8 (1H, m), 7.3-7.4 (1H, m), 7.4-7.5 (2H, m), 7.55-7.63 (1H, m), 7.64-7.7 (1H, m), 7.70-7.78 (1H, m), 7.8-7.86 (1H, m), 7.88-8.06 (2H, m), 13.2 (1H, brs); mass spectrum (ESI): 386 (M+H)

EXAMPLE 40 trans-5-[3'-oxospiro[cyclohexane-1,1'(3'H)-isobenzofuran]-4-yl]-2-phenyl-2,4-dihydroimidazo[4,5-d][1,2,3]triazole $^1$H NMR (300 MHz, DMSO-$d_6$, δppm): 1.74-1.86 (2H, m), 2.14-2.40 (6H, m), 3.14-3.24 (1H, m), 7.36 (1H, t, J=7.5 Hz), 7.52-7.64 (3H, m), 7.66-7.79 (2H, m), 7.52 (1H, d, J=7.5 Hz), 8.03 (2H, d, J=8.2 Hz), 12.68 (1H, brs); mass spectrum (ESI): 386 (M+H)

EXAMPLE 41 trans-2-(2-fluorophenyl)-5-[3'-oxospiro[cyclohexane-1,1'(3'H)-isobenzofuran]-4-yl]-2,4-dihydroimidazo[4,5-d][1,2,3]triazole 4,5-Diamino-2-(2-fluorophenyl)-2H-[1,2,3]triazole was synthesized according to a method similar to the procedure described in Andrianov, V. G.; Semenikhina, V. G.; Eremeev, A. V.; Chem. Heterocycl. Compd., vol. 28, pages 803-807 (1992).

$^1$H NMR (300 MHz, CD$_3$OD/CDCl$_3$=4/1, δppm): 1.86-1.97 (2H, m), 2.20-2.48 (6H, m), 3.38-3.46 (1H, m), 7.31-7.90 (8H, m); mass spectrum (ESI): 404 (M+H)

EXAMPLE 42 trans-2-(4-fluorophenyl)-5-[3'-oxospiro[cyclohexane-1,1'(3'H)-isobenzofuran]-4-yl]-2,4-dihydroimidazo[4,5-d][1,2,3]triazole 4,5-Diamino-2-(4-fluorophenyl)-2H-[1,2,3]triazole was synthesized according to a method similar to the procedure of Example 40.

$^1$H NMR (300 MHz, CD$_3$OD/CDCl$_3$=4/1, δppm): 1.86-1.98 (2H, m), 2.20-2.45 (6H, m), 3.35-3.45 (1H, m), 7.23 (2H, t, J=8.9 Hz), 7.55-7.63 (1H, m), 7.65-7.74 (2H, m), 7.85-7.90 (1H, m), 8.09 (2H, dd, J=4.7 Hz, 8.9 Hz); mass spectrum (ESI): 404 (M+H)

EXAMPLE 43 trans-5-[3-oxospiro[6-azaisobenzofuran-1(3H),1'-cyclohexan]-4'-yl]-2-phenyl-2,4-dihydroimidazo[4,5-c]pyrazole

(1) Preparation of methyl 4-nitro-1H-pyrazole-3-carboxylate

Thionyl chloride (5.1 mL, 70.0 mmol) was added portionwise to a solution of 4-nitro-1H-pyrazole-3-carboxylic acid (10.0 g, 63.7 mmol) in methanol (100 mL). After the mixture was stirred overnight at room temperature, the solvent was evaporated in vacuo. After the residue was dissolved in ethyl acetate, the solution was washed with water and saturated aqueous brine, dried over anhydrous magnesium sulfate, and concentrated in vacuo to obtain the title compound (10.43 g, 95.8%).

(2) Preparation of methyl 4-nitro-1-phenyl-1H-pyrazole-3-carboxylate

To a solution of 4-nitro-1H-pyrazole-3-carboxylate (1.0 g, 5.84 mmol) in methylene chloride (20 mL) were added phenylboric acid (1.43 g, 11.7 mmol), copper(II) acetate (1.60 g, 8.76 mmol) and pyridine (2 mL, 23.4 mmol), and the mixture was stirred overnight at room temperature under an air atmosphere. After removal of the insolubles by filtration, the filtrate was washed with water (twice) and saturated brine, dried over anhydrous magnesium sulfate and concentrated in vacuo to obtain the title compound (1.21 g, 83.5%).

(3) Preparation of 4-nitro-1-phenyl-1H-pyrazole-3-carboxylic acid

Methyl 4-nitro-1-phenyl-1H-pyrazole-3-carboxylate (1.14 g, 4.63 mmol) was suspended in 1N sodium hydroxide (11 mL), and the solution was stirred at room temperature for 2 hours under a nitrogen atmosphere. The precipitates formed upon addition of 1N hydrochloric acid (12 mL) were collected by filtration, washed with water and dried to obtain the title compound (1.00 g, 93.2%).

(4) Preparation of 3-amino-4-nitro-1-phenyl-1H-pyrazole

To a solution of 4-nitro-1-phenyl-1H-pyrazole-3-carboxylic acid (1.00 g, 4.29 mmol) in 1,4-dioxane (15 mL) were added diphenylphosphoryl azide (1.44 mL, 6.65 mmol), triethylamine (1.79 mL, 12.9 mmol) and 2-methyl-2-propanol (7.2 mL, 75.3 mmol), and the mixture was heated under reflux for 2 hours under a nitrogen atmosphere. The reaction solution was cooled down to room temperature, and ethyl acetate was added thereto. The mixture was washed successively with water, saturated aqueous sodium bicarbonate solution and saturated brine, dried over anhydrous magnesium sulfate and concentrated in vacuo. The resulting residue was dissolved in chloroform (10 mL), and then trifluoroacetic acid (5 mL) was added thereto. The solution was stirred at room temperature for 1 hour under a nitrogen atmosphere. After the reaction solution was concentrated, ethyl acetate was added to the resulting residue. The solution was washed with saturated aqueous sodium bicarbonate solution and saturated aqueous brine, dried over anhydrous magnesium sulfate, and concentrated in vacuo. Diisopropyl ether was added to the resulting residue, and the precipitates were collected by filtration and dried to obtain the title compound (827 mg, 94%).

(5) Preparation of 3,4-diamino-1-phenyl-1H-pyrazole

To a solution of 3-amino-4-nitro-1-phenyl-1H-pyrazole (200 mg, 0.98 mmol) in methanol (30 mL) were added conc. hydrochloric acid (0.5 mL) and 10% palladium-carbon (20 mg), and the mixture was stirred for 1.5 hours at room temperature under a hydrogen atmosphere. After removal of the catalyst by filtration, the filtrate was concentrated, and aqueous sodium bicarbonate solution was added to the resulting residue. The solution was extracted 5 times with chloroform, and the chloroform layer was dried over anhydrous magnesium sulfate, and then concentrated in vacuo. Diisopropyl ether was added to the resulting residue, and the precipitates were collected by filtration and dried to obtain the title compound (101 mg, 58.6%).

(6) Preparation of trans-N-(4-mino-1-phenyl-1H-pyrazol-3-yl)-3-oxospiro[6-azaisobenzofuran-1(3H), 1'-cyclohexane]-4'-carboxamide To a solution of trans-3-oxospiro[6-azaisobenzofuran-1 (3H),1'-cyclohexane]-4'-carboxylic acid (100 mg, 0.404 mmol) and 3,4-diamino-1-phenyl-1H-pyrazole (70 mg, 0.404 mmol) in pyridine (2 mL) was added 3-ethyl-1-(3-dimethylaminopropyl) carbodiimide hydrochloride (90 mg, 0.53 mmol), and the mixture was stirred overnight at room temperature under a nitrogen atmosphere. The reaction solution was diluted with ethyl acetate, and washed with water and saturated brine. The organic layer was dried over anhydrous magnesium sulfate and concentrated in vacuo. Diisopropyl ether was added to the resulting residue, and the precipitates were collected by filtration and dried to obtain the title compound (121 mg, 74.2%).

(7) Preparation of trans-5-[3-oxospiro[6-azaisobenzofuran-1(3H),1'-cyclohexan]-4'-yl]-2-phenyl-2,4-dihydroimidazo[4.5-c]pyrazole Trans-N-(4-amino-1-phenyl-1H-pyrazol-3-yl)-3-oxspiro [6-azaisobenzofuran-1(3H),1'-cyclohexane]-4'-carboxamide (121 mg, 0.30 mmol) was suspended in phosphorous oxychloride (1 mL), and the suspension was stirred at 120° C. for 2 hours. The reaction solution was cooled down to room temperature, and then poured into water portionwise. The solution was adjusted to pH 6 using 5N sodium hydroxide aqueous solution, and then extracted with ethyl acetate. The organic layer was washed with saturated aqueous sodium bicarbonate solution and saturated brine, dried over anhydrous magnesium sulfate, and concentrated in vacuo. The residue was separated and purified by a silica gel column chromatography (C-300, methanol:chloroform=1:100 to 1:20) to obtain the title compound (4.5 mg, 3.9%) as a white solid.

$^1$H NMR (300 MHz, DMSO-d$_6$, δppm): 1.9-2.1 (2H, m), 2.1-2.4 (6H, m), 3.2-3.4 (1H, m), 7.25 (1H, t, J=6.8 Hz –, 7.44-7.52 (2H, m), 7.84-7.92 (3H, m), 8.36 (1H, brs), 8.89 (1H, d, J=5.1 Hz), 9.18 (1H, s), 11.8 (1H, s) mass spectrum (ESI): 386 (M+H)

EXAMPLE 44

Preparation of trans-6-[3-oxospiro[6-azaisobenzofuran-1(3H),1'-cyclohexan]-4'-yl]-2-phenyl-1H-imidazo[1,2-b]pyrazole (1) Preparation of methyl trans-3-oxospiro[6-azaisobenzofuran-1(3H),1'-cyclohexane]-4'-carboxylate 1-(3-Dimethylaminopropyl)-3-ethylcarbodiimide hydrochloride (220 mg, 1.17 mmol) was added to pyridine solution (4 mL) containing trans-3-oxospiro[6-azaisobenzofuran-1 (3H),1'-cyclohexane]-4'-carboxylic-acid (500 mg, 2.02 mmol) and methanol (1 mL), and the mixture was stirred at room temperature for 20 hours under a nitrogen atmosphere. After addition of ethyl acetate, the reaction solution was washed successively with water, 10% citric acid solution, saturated aqueous sodium bicarbonate solution and saturated brine, dried over anhydrous magnesium sulfate and concentrated in vacuo to remove the solvent, thereby to obtain the title compound (521.4 mg, 98.7%).

(2) Preparation of trans-[3-oxospiro[6-azaisobenzofuran-1-(3H),1'-cyclohexan]-4'-yl]-3-oxo-3-propionitrile 2.66 M n-butyl lithium/hexane solution (1.125 mL, 2.99 mmol) was added to tetrahydrofuran (10 mL) at −78° C. and subsequently acetonitrile (0.2 mL) was added at −78° C.; the mixture was stirred for 30 minutes. Methyl trans-3-oxospiro [6-azaisobenzofuran-1(3H),1'-cyclohexane]-4'-carboxylate (5.21 mg, 1.99 mmol) was added thereto, and the mixture was stirred for 2 hours while gradually raising the temperature from −78° C. to room temperature. After addition of 10% citric acid solution, the reaction solution was extracted with ethyl acetate. The organic layer was washed with saturated aqueous sodium bicarbonate solution and saturated brine, dried over anhydrous magnesium sulfate and concentrated in vacuo. The residue was purified by silica gel column chromatography (C-300, hexane:ethyl acetate=1:2 to 4:1) to obtain the title compound (210 mg, 39%).

(3) Preparation of 3-amino-5-[3-oxospiro[6-azaisobenzofuran-1(3H),1'-cyclohexan]-4'-yl]-1H-pyrazole After trans-[3-oxospiro[6-azaisobenzofuran-1(3H),1'-cyclohexan]-4'-yl]-3-oxo-3-propionitrile (210 mg) was dissolved in ethanol (8 mL), hydrazine monohydrate (0.045 mL, 0.93 mmol) was added thereto, and the solution was stirred at reflux for 4 hours. Hydrazine monohydrate (0.045 mL, 0.93 mmol) was further added thereto, and the solution was stirred at reflux for 2 hours. The solution was adjusted to pH 2 using conc. hydrochloric acid, and stirred for one hour. After saturated aqueous sodium bicarbonate solution was added to the solution to adjust the pH to 8, it was extracted with ethyl acetate four times. The extract was dried over anhydrous magnesium sulfate and concentrated in vacuo to obtain the title compound (184 mg, 83%) as a cis and trans mixture (2:3).

(4) Preparation of 3-amino-5-[3-oxospiro[6-azaisobenzofuran-1(3H),1'-cyclohexan]-4'-yl]-2-phenacyl-2-H-pyrazole 3-Amino-5-[3-oxospiro[6-azaisobenzofuran-1(3H),1'-cyclohexan]-4'-yl]-1H-pyrazole (180 mg, 0.633 mmol), phenacyl chloride (150 mg, 0.94 mmol) and potassium carbonate (180 mg, 1.27 mmol) were stirred overnight at room temperature in N,N-dimethylformamide (10 mL). The mixture was stirred for further 1 hour at 80° C. The reaction solution was cooled down to room temperature and ethyl acetate was added thereto. The reaction solution was washed with water and saturated brine, and the organic layer was dried over anhydrous magnesium sulfate and concentrated in vacuo to remove the solvent. The residue was separated and purified by a silica gel column chromatography (C-300, methanol:chloroform=1:50 to 1:30) to obtain the title compound (26.5 mg, 10.4%) as a cis and trans mixture.

(5) Preparation of trans-6-[3-oxospiro[6-azaisobenzofuran-1(3H),1'-cyclohexan]-4'-yl]-2-phenyl-1H-imidazo[1,2-b]pyrazole A solution of 3-amino-5-[3-oxospiro[6-azaisobenzofuran-1(3H),1'-cyclohexan]-4'-yl]-2-phenacyl-2H-pyrazole (26.5 mg, 0.058 mmol) in ethanol (0.5 mL) was refluxed overnight. The solvent was evaporated in vacuo, and the residue was separated and purified by a silica gel column chromatography (C-300, ethyl acetate:hexane=1:1 to 2:1 and methanol:chloroform=1:50) to obtain the title compound (2.3 mg, 10.3%).
$^1$H NMR (300 MHz, DMSO-$d_6$, δppm): 1.8-2.3 (8H, m), 3.0-3.4 (1H, m), 5.72 (1H, s), 7.2-7.8 (5H, m), 7.86 (1H, dd, J=1.1 Hz, 4.9 Hz), 8.06 (1H, s), 8.87 (1H, d, J=4.9 Hz), 9.08 (1H, d, J=1.1 Hz), 11.4 (1H, brs); mass spectrum (ESI): 385 (M+H)

The following compounds were synthesized according to a method similar to the procedure of Example 13.

EXAMPLE 45

3-[3-oxospiro[6-azaisobenzofuran-1(3H),4'-piperidin]-1'-yl]-5-(2-phenylpyrimidin-4-yl)-1H-pyrazole $^1$H NMR (400 MHz, DMSO-$d_6$, δppm): 1.82-1.94 (2H, m), 2.39-2.57 (2H, m), 3.05-3.20 (2H, m), 3.78-3.85 (2H, m), 6.78 (1H, s), 7.48-7.58 (3H, m), 7.67-7.77 (1H, m), 7.84 (1H, dd, J=1.1 Hz, 5.1 Hz), 8.50-8.64 (2H, m), 8.84-8.95 (1H, m), 8.86 (1H, d, J=5.1 Hz), 9.18 (1H, s); mass spectrum (ESI): 425

EXAMPLE 46

3-[3-oxospiro[6-azaisobenzofuran-1(3H),4'-piperidin]-1'-yl]-5-[2-(2-fluorophenyl)pyrimidin-4-yl]-1H-pyrazole $^1$H NMR (400 MHz, DMSO-$d_6$, δppm): 1.80-1.94 (2H, m), 2.39-2.57 (2H, m), 3.05-3.20 (2H, m), 3.70-3.95 (2H, m), 6.65 (1H, s), 7.20-7.36 (2H, m), 7.45-7.55 (1H, m), 7.65-7.80 (1H, m), 7.78 (1H, d, J=5.1 Hz), 8.20 (1H, s), 8.83 (1H, d, J=5.1 Hz), 8.83-8.95 (1H, m), 9.12 (1H, s); mass spectrum (ESI): 443

EXAMPLE 47

3-[3-oxospiro[6-azaisobenzofuran-1(3H),4'-piperidin]-1'-yl]-5-[2-(4-fluorophenyl)pyrimidin-4-yl]-1H-pyrazole $^1$H NMR (400 MHz, DMSO-$d_6$, δppm): 1.83-1.95 (2H, m), 2.39-2.60 (2H, m), 3.05-3.20 (2H, m), 3.70-3.95 (2H, m), 6.77 (1H, s), 7.30-7.39 (2H, m), 7.65-7.85 (2H, m), 8.50-8.70 (2H, m), 8.80-8.94 (2H, m), 9.18 (1H, s); mass spectrum (ESI): 443

Formulation Example 1

The compound (20.0 g) of Example 1, lactose (417 g), crystalline cellulose (80 g) and partial α-starch (80 g) were blended using a V cone blender. To the mixture was added magnesium stearate (3.0 g), and the whole was blended. The blended powder was compressed into 3,000 tablets by conventional procedure so that each tablet has a diameter of 7.0 mm and a weight of 150 mg.

Content Per Tablet (150 mg)

| | |
|---|---|
| The Compound of Example 1 | 5.0 mg |
| Lactose | 104.25 mg |
| Crystalline cellulose | 20.0 mg |
| Partial α-starch | 20.0 mg |
| Magnesium stearate | 0.75 mg |

Formulation Example 2

Hydroxypropyl cellulose 2910 (10.8 g) and polyethylene glycol 6000 (2.1 g) were dissolved in purified water (172.5 g). To the solution was dispersed titanium dioxide (2.1 g) to provide a coating liquid. 2,500 tablets separately prepared according to Formulation Example 1 were subjected to spray-coating with the coating liquid using HICOATER-MINI to provide film coated tablets with a weight of 155 mg.

Content Per Tablet (155 mg)

| The tablets of Formulation Example 1 | 150 mg |
|---|---|
| Hydroxypropyl cellulose 2910 | 3.6 mg |
| Polyethylene glycol 6000 | 0.7 mg |
| Titanium dioxide | 0.7 mg |

INDUSTRIAL APPLICABILITY

Since compounds of the present invention exhibit NPY antagonistic effects especially on NPY Y5 receptors and show excellent pharmacokinetics such as transport into brain or transport to cerebrospinal fluid, etc., and they are highly safe, they are useful for the treatment of various diseases related to NPY, for example, cardiovascular disorders such as angina, acute or congestive heart failure; myocardial infarction, hypertension, nephropathy, electrolyte abnormality, vasospasm, atherosclerosis, etc., central nervous system disorders such as bulimia, depression, anxiety, seizure, epilepsy, dementia, pain, alcoholism, drug withdrawal, circadian rhythm disorders, schizophrenia, memory impairment, sleep disorders, cognitive impairment, etc., metabolic diseases such as obesity, diabetes, hormone abnormality, hypercholesterolemia, hyperlipemia, gout, fatty liver, etc., genital or reproductive disorders such as infertility, preterm labor, sexual dysfunction, etc., gastro-intestinal disorders, respiratory disorder, inflammatory diseases or glaucoma, and the like, also for example, atherosclerosis, hypogonadism, hyperandrogenism, polycystic ovary syndrome, hirsutism, gastrointestinal motility disorder, obesity-related gastro-esophageal reflux, obesity hypoventilation (Pickwickian syndrome), sleep apnea, inflammation, systemic inflammation of the vasculature, osteoarthritis, insulin resistance, bronchoconstriction, alcohol preference, metabolic syndrome, (syndrome X), Alzheimer's disease, cardiac hypertrophy, left ventricular hypertrophy, hypertriglyceridemia, low HDL cholesterol, cardiovascular disorders such as coronary heart disease (CHD), cerebrovascular disease, stroke, peripheral vascular disease, sudden death, gallbladder diseases, cancer (breast, endometrial, colon), breathlessness, hyperuricemia, impaired fertility, low back pain, or increased anesthetic risk, and the like; renal system diseases; renal abnormalities such as dysfunction in body fluid flow, abnormalities of material transportation, and renal failure; shock; arrhythmia; symptoms related to surge in sympathomimetic activity during or after operation on coronary artery or gastrointestinal tracts; diseases related to brain or central nervous system, such as cerebral infarction, neurodegeneration, cerebral stroke, cerebrovascular spasm or cerebral hemorrhage; symptoms related to pain or nociception; diseases related to abnormalities in gastrointestinal motility or secretion, such as various ileuses, urinary incontinence, and Crohn's disease; eating disorders such as anorexia and bulimia; inflammatory symptoms or diseases; asthma; bronchiole constriction; or diseases related to abnormal secretion of hormones such as luteinizing hormone, growth hormone, insulin, and luteotropic hormone.

The invention claimed is:

1. A compound of the formula (I):

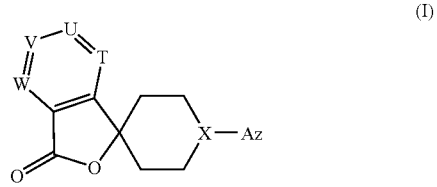

wherein Az is a group comprising a monocyclic azole or a bicyclic aromatic ring of the same or different fused azoles, which is optionally substituted by a substituent selected from the group consisting of halogen, cyano, lower alkyl, halo-lower alkyl, hydroxy, lower alkoxy, halo-lower alkoxy, lower alkoxycarbonyl, lower alkylsulfonyl, lower alkylsulfonyloxy, —N($R^1$)$R^2$ and -$Q^1$-$Ar^1$;

$Ar^1$ is aryl or heteroaryl, any of which is optionally substituted by a substituent selected from the group consisting of halogen, nitro, oxo, hydroxy, lower alkyl, halo-lower alkyl, hydroxy-lower alkyl, cyclo-lower alkyl, lower alkenyl, lower alkoxy, halo-lower alkoxy, lower alkylthio, lower alkylsulfonyl, carboxyl, lower alkanoyl, lower alkoxycarbonyl, lower alkanoylamino and -$Q^2$-$Ar^2$;

$Ar^2$ is aryl or heteroaryl, any of which is optionally substituted by a substituent selected from the group consisting of halogen, cyano, lower alkyl, halo-lower alkyl, hydroxy-lower alkyl, hydroxy, lower alkoxy, halo-lower alkoxy, lower alkylamino, di-lower alkylamino, lower alkanoyl and aryl;

$Q^1$ and $Q^2$ are independently a single bond, oxygen atom, carbonyl or —N($R^3$)—;

$R^1$ and $R^2$ are independently hydrogen atom or lower alkyl, or $R^1$ and $R^2$, taken together, form lower alkylene which may be interrupted by oxygen atom, sulfur atom or imino;

$R^3$ is hydrogen atom or lower alkyl;

T, V and W are methine, said methine being optionally substituted by a substituent selected from the group consisting of halogen, lower alkyl, halo-lower alkyl, hydroxy, lower alkoxy and halo-lower alkoxy; U is nitrogen atom; and X is nitrogen atom, or a salt or ester thereof.

2. The compound, or a salt or ester thereof, as claimed in claim 1, wherein Az is a group comprising a monocyclic azole or a bicyclic aromatic ring of the same or different fused azoles, which is substituted by -$Q^1$-$Ar^1$.

3. The compound, or a salt or ester thereof, as claimed in claim 1, wherein a group comprising a monocyclic azole as Az is selected from the following formulae (a):

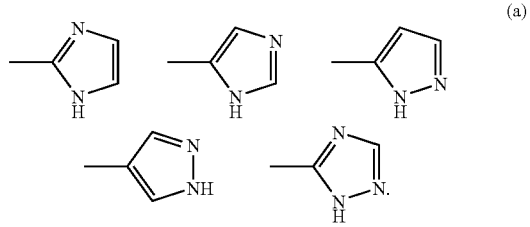

4. The compound, or a salt or ester thereof, as claimed in claim 1, wherein a group comprising a bicyclic aromatic ring of the same or different fused azoles as Az is selected from the following formulae (b):

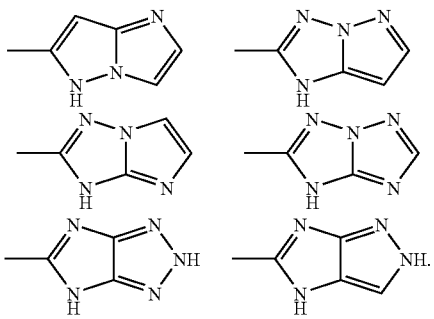

5. The compound, or a salt or ester thereof, as claimed in claim 1, wherein $Q^1$ is a single bond.

6. The compound, or a salt or ester thereof, as claimed in claim 1, wherein $Ar^1$ is phenyl or naphthyl, any of which is optionally substituted by a substituent selected from the group consisting of halogen, nitro, oxo, hydroxy, lower alkyl, halo-lower alkyl, hydroxy-lower alkyl, cyclo-lower alkyl, lower alkenyl, lower alkoxy, halo-lower alkoxy, lower alkylthio, lower alkylsulfonyl, carboxyl, lower alkanoyl, lower alkoxycarbonyl, lower alkanoylamino and $-Q^2-Ar^2$.

7. The compound, or a salt or ester thereof, as claimed in claim 1, wherein $Ar^1$ is heteroaryl which is optionally substituted by a substituent selected from the group consisting of halogen, nitro, oxo, hydroxy, lower alkyl, halo-lower alkyl, hydroxy-lower alkyl, cyclo-lower alkyl, lower alkenyl, lower alkoxy, halo-lower alkoxy, lower alkylthio, lower alkylsulfonyl, carboxyl, lower alkanoyl, lower alkoxycarbonyl, lower alkanoylamino and $-Q^2-Ar^2$.

8. The compound, or a salt or ester thereof, as claimed in claim 7, wherein the heteroaryl is imidazolyl, furyl, thienyl, pyrazolyl, 1,2,3-triazolyl, 1,2,4-triazolyl, thiazolyl, oxazolyl, isoxazolyl, 1,2,4-oxadiazolyl, 1,3,4-oxadiazolyl, 1,2,4-thiadiazolyl, 1,3,4-thiadiazolyl, pyridyl, pyrazinyl, pyrimidinyl, benzofuranyl, quinolyl or isoquinolyl.

9. The compound, or a salt or ester thereof, as claimed in claim 1, wherein Az is a group selected from the following formulae ($a_1$):

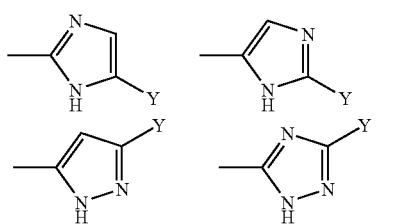

wherein Y is hydrogen atom, halogen, cyano, lower alkyl, halo-lower alkyl, hydroxy, lower alkoxy, halo-lower alkoxy, lower alkoxycarbonyl, lower alkylsulfonyl, lower alkylsulfonyloxy, $-N(R^1)R^2$ or $-Q^1-Ar^1$;

$Ar^1$ is aryl or heteroaryl, any of which is optionally substituted by a substituent selected from the group consisting of halogen, nitro, oxo, hydroxy, lower alkyl, halo-lower alkyl, hydroxy-lower alkyl, cyclo-lower alkyl, lower alkenyl, lower alkoxy, halo-lower alkoxy, lower alkylthio, lower alkylsulfonyl, carboxyl, lower alkanoyl, lower alkoxycarbonyl, lower alkanoylamino and $-Q^2-Ar^2$;

$Ar^2$ is aryl or heteroaryl, any of which is optionally substituted by a substituent selected from the group consisting of halogen, cyano, lower alkyl, halo-lower alkyl, hydroxy-lower alkyl, hydroxy, lower alkoxy, halo-lower alkoxy, lower alkylamino, di-lower alkylamino, lower alkanoyl and aryl;

$Q^1$ and $Q^2$ are independently a single bond, oxygen atom, carbonyl or $-N(R^3)-$;

$R^1$ and $R^2$ are independently hydrogen atom or lower alkyl, or $R^1$ and $R^2$, taken together, form lower alkylene which may be interrupted by oxygen atom, sulfur atom or imino; and $R^3$ is hydrogen atom or lower alkyl, or the following formulae ($b_1$):

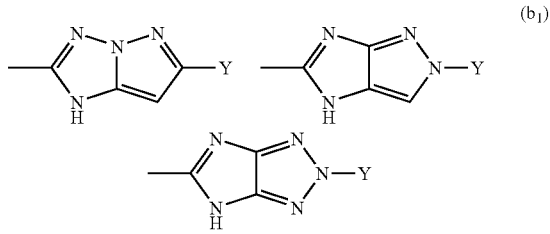

wherein Y has the same meaning as defined above.

10. The compound, or a salt or ester thereof, as claimed in claim 9, wherein Y is $-Q^1-Ar^1$.

11. The compound, or a salt or ester thereof, as claimed in claim 1, wherein T, V and W are independently methine which is optionally substituted by a substituent selected from the group consisting of halogen, lower alkyl, hydroxy and lower alkoxy.

12. The compound, or a salt thereof, as claimed in claim 1, which is
3-(3-biphenylyl)-5-[3-oxospiro[6-azaisobenzofuran-1 (3H),4'-piperidin]-1'-yl]-1H-pyrazole,
3-[3-oxospiro[6-azaisobenzofuran-1(3H),4'-piperidin]-1'-yl]-5-(2-phenylpyridine-4-yl)-1H-pyrazole,
3-[3-oxospiro[6-azaisobenzofuran-1(3H),4'-piperidin-1'-yl]-5-(2-phenylpyrimidin-4-yl)-1H-pyrazole,
3-[3-oxospiro[6-azaisobenzofuran-1(3H),4'-piperidin-1'-yl]-5-[2-(2-fluorophenyl)pyrimidin-4-yl]-1H-pyrazole, or
3-[3-oxospiro[6-azaisobenzofuran-1(3H),4'-piperidin-1'-yl]-5-[2-(4-fluorophenyl)pyrimidin-4-yl]-1H-pyrazole.

13. The compound, or a salt thereof, as claimed in claim 1, which is 3-[3-oxospiro[6-azaisobenzofuran-1(3H),4'-piperidin-1'-yl]-5-(2-phenylpyrimidin-4-yl)-1H-pyrazole.

14. The compound, or a salt thereof, as claimed in claim 1, which is 3-[3-oxospiro[6-azaisobenzofuran-1(3H),4'-piperidin-1'-yl]-5-[2-(2-fluorophenyl)pyrimidin-4-yl]-1H-pyrazole.

15. The compound, or a salt thereof, as claimed in claim 1, which is 3-[3-oxospiro[6-azaisobenzofuran-1(3H),4'-piperidin-1'-yl]-5-[2-(4-fluorophenyl)pyrimidin-4-yl]-1H-pyrazole.

16. A process for preparing a compound of the formula (I-1):

(I-1)

wherein Ar¹ is aryl or heteroaryl, any of which is optionally substituted by a substituent selected from the group consisting of halogen, nitro, oxo, hydroxy, lower alkyl, halo-lower alkyl, hydroxy-lower alkyl, cyclo-lower alkyl, lower alkenyl, lower alkoxy, halo-lower alkoxy, lower alkylthio, lower alkylsulfonyl, carboxyl, lower alkanoyl, lower alkoxycarbonyl, lower alkanoylamino and -$Q^2$-$Ar^2$;

Ar² is aryl or heteroaryl, any of which is optionally substituted by a substituent selected from the group consisting of halogen, cyano, lower alkyl, halo-lower alkyl, hydroxy-lower alkyl, hydroxy, lower alkoxy, halo-lower alkoxy, lower alkylamino, di-lower alkylamino, lower alkanoyl and aryl;

$Q^1$ and $Q^2$ are independently a single bond, oxygen atom, carbonyl or —N($R^3$)—;

$R^1$ and $R^2$ are independently hydrogen atom or lower alkyl, or $R^1$ and $R^2$, taken together, form lower alkylene which may be interrupted by oxygen atom, sulfur atom or imino; and $R^3$ is hydrogen atom or lower alkyl;

T, V and W are methine, said methine being optionally substituted by a substituent selected from the group consisting of halogen, lower alkyl, halo-lower alkyl, hydroxy, lower alkoxy and halo-lower alkoxy;

U is nitrogen atom;

X is nitrogen atom; and

Y and Z are independently hydrogen atom, halogen, cyano, lower alkyl, halo-lower alkyl, hydroxy, lower alkoxy, halo-lower alkoxy, lower alkoxycarbonyl, lower alkylsulfonyl, lower alkylsulfonyloxy, —N($R^1$)$R^2$ or -$Q^1$-$Ar^1$, or a salt or ester thereof, by reacting a compound of the formula (II):

(II)

wherein $L^1$ is a leaving group;

y and z are independently hydrogen atom, halogen, cyano, lower alkyl, halo-lower alkyl, lower alkoxy, halo-lower alkoxy, lower alkoxycarbonyl, lower alkylsulfonyl, lower alkylsulfonyloxy, —N($R^{1P}$)$R^{2P}$, -$Q^{1P}$-$Ar^{1P}$ or optionally protected hydroxy;

$Ar^{1P}$ is aryl or heteroaryl, any of which is optionally substituted by a substituent selected from the group consisting of halogen, nitro, lower alkyl, halo-lower alkyl, cyclo-lower alkyl, lower alkenyl, lower alkoxy, halo-lower alkoxy, lower alkylthio, lower alkylsulfonyl, lower alkanoyl, lower alkoxycarbonyl, lower alkanoylamino, -$Q^{2P}$-$Ar^{2P}$, optionally protected oxo, optionally protected hydroxy, optionally protected hydroxy-lower alkyl and optionally protected carboxyl;

$Ar^{2P}$ is aryl or heteroaryl, any of which is optionally substituted by a substituent selected from the group consisting of halogen, cyano, lower alkyl, halo-lower alkyl, lower alkoxy, halo-lower alkoxy, di-lower alkylamino, lower alkanoyl, aryl, optionally protected hydroxy-lower alkyl, optionally protected hydroxy and optionally protected lower alkylamino;

$Q^{1P}$ and $Q^{2P}$ are independently a single bond, oxygen atom, optionally protected carbonyl or —N($R^3$);

$R^{1P}$ and $R^{2P}$ are independently an amino-protecting group, an imino-protecting group, hydrogen atom or lower alkyl, or $R^{1P}$ and $R^{2P}$, taken together, form lower alkylene which may be interrupted by oxygen atom, sulfur atom or optionally protected imino; and $R^3$ has the same meaning as defined above, with a compound of the formula (III):

(III)

wherein t, v and w are methine, said methine being optionally substituted by a substituent selected from the group consisting of halogen, lower alkyl, halo-lower alkyl, lower alkoxy, halo-lower alkoxy and optionally protected hydroxy; u is nitrogen atom, and X has the same meaning as defined above or its salt to give a compound of the formula (IV):

(IV)

wherein t, u, v, w, X, y and z have each the same meaning as defined above, and optionally removing the protecting group(s) therefrom.

17. A process for preparing a compound of the formula (I-2):

(I-2)

wherein Ar¹ is aryl or heteroaryl, any of which is optionally substituted by a substituent selected from the group consisting of halogen, nitro, oxo, hydroxy, lower alkyl, halo-lower alkyl, hydroxy-lower alkyl, cyclo-lower alkyl, lower alkenyl, lower alkoxy, halo-lower alkoxy, lower alkylthio, lower alkylsulfonyl, carboxyl, lower alkanoyl, lower alkoxycarbonyl, lower alkanoylamino and -Q²-Ar²;
  Ar² is aryl or heteroaryl, any of which is optionally substituted by a substituent selected from the group consisting of halogen, cyano, lower alkyl, halo-lower alkyl, hydroxy-lower alkyl, hydroxy, lower alkoxy, halo-lower alkoxy, lower alkylamino, di-lower alkylamino, lower alkanoyl and aryl;
  $Q^1$ and $Q^2$ are independently a single bond, oxygen atom, carbonyl or —N($R^3$)—;
  $R^1$ and $R^2$ are independently hydrogen atom or lower alkyl, or $R^1$ and $R^2$, taken together, form lower alkylene which may be interrupted by oxygen atom, sulfur atom or imino;
  T, V and W are methine or nitrogen atom, said methine being optionally substituted by a substituent selected from the group consisting of halogen, lower alkyl, halo-lower alkyl, hydroxy, lower alkoxy and halo-lower alkoxy;
  $R^3$ is hydrogen atom or lower alkyl;
  U is nitrogen atom;
  X is nitrogen atom; and
  Y and Z are independently hydrogen atom, halogen, cyano, lower alkyl, halo-lower alkyl, hydroxy, lower alkoxy, halo-lower alkoxy, lower alkoxycarbonyl, lower alkylsulfonyl, lower alkylsulfonyloxy, —N($R^1$)$R^2$ or -$Q^1$-$Ar^1$,
or a salt or ester thereof,
by reacting a compound of the formula (V):

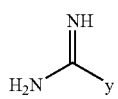

(V)

wherein y is hydrogen atom, halogen, cyano, lower alkyl, halo-lower alkyl, lower alkoxy, halo-lower alkoxy, lower alkoxycarbonyl, lower alkylsulfonyl, lower alkylsulfonyloxy, —N($R^{1P}$)$R^{2P}$, -$Q^{1P}$-$Ar^{1P}$, or optionally protected hydroxy;
  $Ar^{1P}$ is aryl or heteroaryl, any of which is optionally substituted by a substituent selected from the group consisting of halogen, nitro, lower alkyl, halo-lower alkyl, cyclo-lower alkyl, lower alkenyl, lower alkoxy, halo-lower alkoxy, lower alkylthio, lower alkylsulfonyl, lower alkanoyl, lower alkoxycarbonyl, lower alkanoylamino, -$Q^{2P}$-$Ar^{2P}$, optionally protected oxo, optionally protected hydroxy, optionally protected hydroxy-lower alkyl and optionally protected carboxyl;
  $Ar^{2P}$ is aryl or heteroaryl, any of which is optionally substituted by a substituent selected from the group consisting of halogen, cyano, lower alkyl, halo-lower alkyl, lower alkoxy, halo-lower alkoxy, di-lower alkylamino, lower alkanoyl, aryl, optionally protected hydroxy-lower alkyl, optionally protected hydroxy and optionally protected lower alkylamino;
  $Q^{1P}$ and $Q^{2P}$ are independently a single bond, oxygen atom, optionally protected carbonyl or —N($R^3$);
  $R^{1P}$ and $R^{2P}$ are independently an amino-protecting group, an imino-protecting group, hydrogen atom or lower alkyl, or $R^{1P}$ and $R^{2P}$, taken together, form lower alkylene which may be interrupted by oxygen atom, sulfur atom or optionally protected imino; and
  $R^3$ has the same meaning as defined above
or its salt, with a compound of the formula (VI):

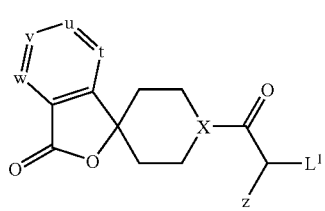

(VI)

wherein $L^1$ is a leaving group;
  t, v and w are methine, said methine being optionally substituted by a substituent selected from the group consisting of halogen, lower alkyl, halo-lower alkyl, lower alkoxy, halo-lower alkoxy, and optionally protected hydroxy; u is nitrogen atom;
  X has the same meaning as defined above;
  z is hydrogen atom, halogen, cyano, lower alkyl, halo-lower alkyl, lower alkoxy, halo-lower alkoxy, lower alkoxycarbonyl, lower alkylsulfonyl, lower alkylsulfonyloxy, —N($R^{1P}$)$R^{2P}$, -$Q^{1P}$-$Ar^{1P}$ or optionally protected hydroxy; and
  $Ar^{1P}$, $Q^{1P}$, $R^{1P}$ and $R^{2P}$ have each the same meaning as defined above
or its salt to give a compound of the formula (VII):

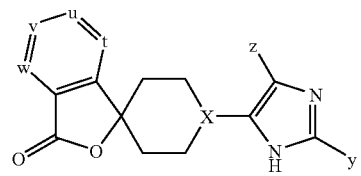

(VII)

wherein t, u, v, w, X, y and z have each the same meaning as defined above), and optionally removing the protecting group(s) therefrom.

18. A process for preparing a compound of the formula (I-3):

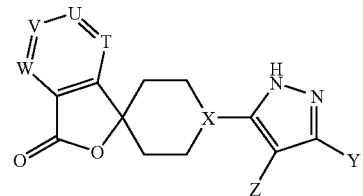

(I-3)

wherein $Ar^1$ is aryl or heteroaryl, any of which is optionally substituted by a substituent selected from the group consisting of halogen, nitro, oxo, hydroxy, lower alkyl, halo-lower alkyl, hydroxy-lower alkyl, cyclo-lower alkyl, lower alkenyl, lower alkoxy, halo-lower alkoxy, lower alkylthio, lower alkylsulfonyl, carboxyl, lower alkanoyl, lower alkoxycarbonyl, lower alkanoylamino and -Q²-Ar²;
  Ar² is aryl or heteroaryl, any of which is optionally substituted by a substituent selected from the group consisting of halogen, cyano, lower alkyl, halo-lower alkyl, hydroxy-lower alkyl, hydroxy, lower alkoxy, halo-lower alkoxy, lower alkylamino, di-lower alkylamino, lower alkanoyl and aryl;

$Q^1$ and $Q^2$ are independently a single bond, oxygen atom, carbonyl or —N(R$^3$)—;

R$^1$ and R$^2$ are independently hydrogen atom or lower alkyl, or R$^1$ and R$^2$, taken together, form lower alkylene which may be interrupted by oxygen atom, sulfur atom or imino;

T, V and W are methine, said methine being optionally substituted by a substituent selected from the group consisting of halogen, lower alkyl, halo-lower alkyl, hydroxy, lower alkoxy and halo-lower alkoxy;

R$^3$ is hydrogen atom or lower alkyl;

U is nitrogen atom;

X is nitrogen atom; and

Y and Z are independently hydrogen atom, halogen, cyano, lower alkyl, halo-lower alkyl, hydroxy, lower alkoxy, halo-lower alkoxy, lower alkoxycarbonyl, lower alkylsulfonyl, lower alkylsulfonyloxy, —N(R$^1$)R$^2$ or -Q$^1$-Ar$^1$, or a salt or ester thereof, by subjecting a compound of the formula (VIII):

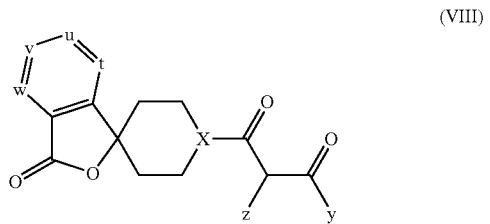

(VIII)

wherein t, v and w are methine, said methine being optionally substituted by a substituent selected from the group consisting of halogen, lower alkyl, halo-lower alkyl, lower alkoxy, halo-lower alkoxy, and optionally protected hydroxy; u is nitrogen atom;

y and z are independently hydrogen atom, halogen, cyano, lower alkyl, halo-lower alkyl, lower alkoxy, halo-lower alkoxy, lower alkoxycarbonyl, lower alkylsulfonyl, lower alkylsulfonyloxy, —N(R$^{1P}$)R$^{2P}$, -Q$^{1P}$-Ar$^{1P}$, or optionally protected hydroxy;

Ar$^{1P}$ is aryl or heteroaryl, any of which is optionally substituted by a substituent selected from the group consisting of halogen, nitro, lower alkyl, halo-lower alkyl, cyclo-lower alkyl, lower alkenyl, lower alkoxy, halo-lower alkoxy, lower alkylthio, lower alkylsulfonyl, lower alkanoyl, lower alkoxycarbonyl, lower alkanoylamino, -Q$^{2P}$-Ar$^{2P}$, optionally protected oxo, optionally protected hydroxy, optionally protected hydroxy-lower alkyl and optionally protected carboxyl;

Ar$^{2P}$ is aryl or heteroaryl, any of which is optionally substituted by a substituent selected from the group consisting of halogen, cyano, lower alkyl, halo-lower alkyl, lower alkoxy, halo-lower alkoxy, di-lower alkylamino, lower alkanoyl, aryl and optionally protected hydroxy-lower alkyl, optionally protected hydroxy and optionally protected lower alkylamino;

Q$^{1P}$ and Q$^{2P}$ are independently a single bond, oxygen atom, optionally protected carbonyl or —N(R$^3$)—;

R$^{1P}$ and R$^{2P}$ are independently an amino-protecting group, an imino-protecting group, hydrogen atom or lower alkyl, or R$^{1P}$ and R$^{2P}$, taken together, form lower alkylene which may be interrupted by oxygen atom, sulfur atom or optionally protected imino; and X and R$^3$ have each the same meaning as defined above and hydrazine to dehydrative ring closure to give a compound of the formula (IX):

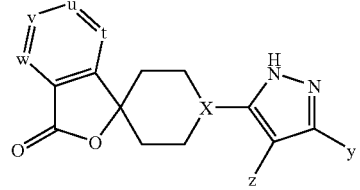

(IX)

wherein t, u, v, w, X, y and z have each the same meaning as defined above, and optionally removing the protective group(s) therefrom.

19. A process for preparing a compound of the formula (I-4):

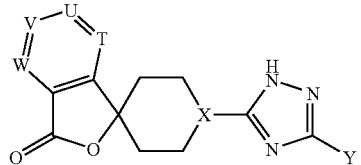

(I-4)

wherein Ar$^1$ is aryl or heteroaryl, any of which is optionally substituted by a substituent selected from the group consisting of halogen, nitro, oxo, hydroxy, lower alkyl, halo-lower alkyl, hydroxy-lower alkyl, cyclo-lower alkyl, lower alkenyl, lower alkoxy, halo-lower alkoxy, lower alkylthio, lower alkylsulfonyl, carboxyl, lower alkanoyl, lower alkoxycarbonyl, lower alkanoylamino and -Q$^2$-Ar$^2$;

Ar$^2$ is aryl or heteroaryl, any of which is optionally substituted by a substituent selected from the group consisting of halogen, cyano, lower alkyl, halo-lower alkyl, hydroxy-lower alkyl, hydroxy, lower alkoxy, halo-lower alkoxy, lower alkylamino, di-lower alkylamino, lower alkanoyl and aryl;

Q$^1$ and Q$^2$ are independently a single bond, oxygen atom, carbonyl or —N(R$^3$)—;

R$^1$ and R$^2$ are independently hydrogen atom or lower alkyl, or R$^1$ and R$^2$, taken together, form lower alkylene which may be interrupted by oxygen atom, sulfur atom or imino;

R$^3$ is hydrogen atom or lower alkyl;

T, V and W are methine, said methine being optionally substituted by a substituent selected from the group consisting of halogen, lower alkyl, halo-lower alkyl, hydroxy, lower alkoxy and halo-lower alkoxy;

U is nitrogen atom;

X is nitrogen atom; and

Y is hydrogen atom, halogen, cyano, lower alkyl, halo-lower alkyl, hydroxy, lower alkoxy, halo-lower alkoxy, lower alkoxycarbonyl, lower alkylsulfonyl, lower alkylsulfonyloxy, —N(R$^1$)R$^2$ or -Q$^1$-Ar$^1$, or a salt or ester thereof, by reacting a compound of the formula (X):

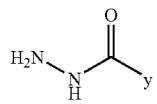

wherein y is hydrogen atom, halogen, cyano, lower alkyl, halo-lower alkyl, lower alkoxy, halo-lower alkoxy, lower alkoxycarbonyl, lower alkylsulfonyl, lower alkylsulfonyloxy, —N(R$^{1P}$)R$^{2P}$, -Q$^{1P}$-Ar$^{1P}$, or optionally protected hydroxy;

Ar$^{1P}$ is aryl or heteroaryl, any of which is optionally substituted by a substituent selected from the group consisting of halogen, nitro, lower alkyl, halo-lower alkyl, cyclo-lower alkyl, lower alkenyl, lower alkoxy, halo-lower alkoxy, lower alkylthio, lower alkylsulfonyl, lower alkanoyl, lower alkoxycarbonyl, lower alkanoylamino, -Q$^{2P}$-Ar$^{2P}$, optionally protected oxo, optionally protected hydroxy, optionally protected hydroxy-lower alkyl and optionally protected carboxyl;

Ar$^{2P}$ is aryl or heteroaryl, any of which is optionally substituted by a substituent selected from the group consisting of halogen, cyano, lower alkyl, halo-lower alkyl, lower alkoxy, halo-lower alkoxy, di-lower alkylamino, lower alkanoyl, aryl, optionally protected hydroxy-lower alkyl, optionally protected hydroxy and optionally protected lower alkylamino;

Q$^{1P}$ and Q$^{2P}$ are independently a single bond, oxygen atom, optionally protected carbonyl or —N(R$^3$);

R$^{1P}$ and R$^{2P}$ are independently an amino-protecting group, an imino-protecting group, hydrogen atom or lower alkyl, or R$^{1P}$ and R$^{2P}$, taken together, form lower alkylene which may be interrupted by oxygen atom, sulfur atom or optionally protected imino; and R$^3$ has the same meaning as defined above or its salt, with a compound of the formula (XI):

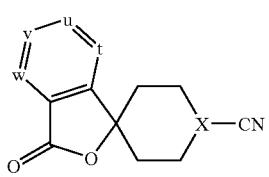

wherein t, v and w are methine, said methine being optionally substituted by a substituent selected from the group consisting of halogen, lower alkyl, halo-lower alkyl, lower alkoxy, halo-lower alkoxy, and optionally protected hydroxy; u is nitrogen atom;

X has the same meaning as defined above, or its salt to give a compound of the formula (XII):

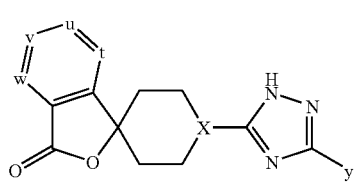

wherein t, u, v, w, X and y have each the same meaning as defined above, and optionally removing the protecting group(s) therefrom.

20. A process for preparing a compound of the formula (I-6):

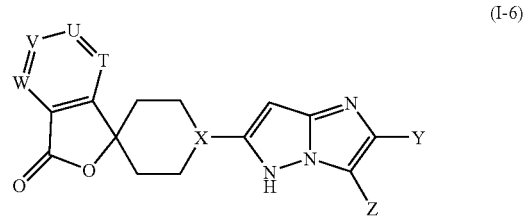

wherein Ar$^1$ is aryl or heteroaryl, any of which is optionally substituted by a substituent selected from the group consisting of halogen, nitro, oxo, hydroxy, lower alkyl, halo-lower alkyl, hydroxy-lower alkyl, cyclo-lower alkyl, lower alkenyl, lower alkoxy, halo-lower alkoxy, lower alkylthio, lower alkylsulfonyl, carboxyl, lower alkanoyl, lower alkoxycarbonyl, lower alkanoylamino and -Q$^2$-Ar$^2$;

Ar$^2$ is aryl or heteroaryl, any of which is optionally substituted by a substituent selected from the group consisting of halogen, cyano, lower alkyl, halo-lower alkyl, hydroxy-lower alkyl, hydroxy, lower alkoxy, halo-lower alkoxy, lower alkylamino, di-lower alkylamino, lower alkanoyl and aryl;

Q$^1$ and Q$^2$ are independently a single bond, oxygen atom, carbonyl or —N(R$^3$)—;

R$^1$ and R$^2$ are independently hydrogen atom or lower alkyl, or R$^1$ and R$^2$, taken together, form lower alkylene which may be interrupted by oxygen atom, sulfur atom or imino;

R$^3$ is hydrogen atom or lower alkyl;

T, V and W are methine, said methine being optionally substituted by a substituent selected from the group consisting of halogen, lower alkyl, halo-lower alkyl, hydroxy, lower alkoxy and halo-lower alkoxy;

U is nitrogen atom;

X is nitrogen atom; and

Y and Z are independently hydrogen atom, halogen, cyano, lower alkyl, halo-lower alkyl, hydroxy, lower alkoxy, halo-lower alkoxy, lower alkoxycarbonyl, lower alkylsulfonyl, lower alkylsulfonyloxy, —N(R$^1$)R$^2$ or -Q$^1$-Ar$^1$, or a salt or ester thereof, by reacting a compound of the formula (II):

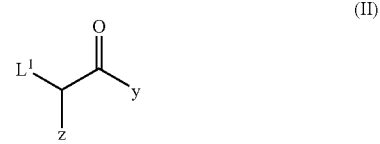

wherein L$^1$ is a leaving group;

y and z are independently hydrogen atom, halogen, cyano, lower alkyl, halo-lower alkyl, lower alkoxy, halo-lower alkoxy, lower alkoxycarbonyl, lower alkylsulfonyl, lower alkylsulfonyloxy, —N(R$^{1P}$)R$^{2P}$, -Q$^{1P}$-Ar$^{1P}$ or optionally protected hydroxy;

Ar$^{1P}$ is aryl or heteroaryl, any of which is optionally substituted by a substituent selected from the group consisting of halogen, nitro, lower alkyl, halo-lower alkyl, cyclo-lower alkyl, lower alkenyl, lower alkoxy, halo-lower alkoxy, lower alkylthio, lower alkylsulfonyl, lower alkanoyl, lower alkoxycarbonyl, lower alkanoylamino, -Q$^{2P}$-Ar$^{2P}$, optionally protected oxo, optionally protected hydroxy, optionally protected hydroxy-lower alkyl and optionally protected carboxyl;

Ar$^{2P}$ is aryl or heteroaryl, any of which is optionally substituted by a substituent selected from the group consisting of halogen, cyano, lower alkyl, halo-lower alkyl, lower alkoxy, halo-lower alkoxy, di-lower alkylamino, lower alkanoyl, aryl, optionally protected hydroxy-lower alkyl, optionally protected hydroxy and optionally protected lower alkylamino;

Q$^{1P}$ and Q$^{2P}$ are independently a single bond, oxygen atom, optionally protected carbonyl or —N(R$^3$);

R$^{1P}$ and R$^{2P}$ are independently an amino-protecting group, an imino-protecting group, hydrogen atom or lower alkyl, or R$^{1P}$ and R$^{2P}$, taken together, form lower alkylene which may be interrupted by oxygen atom, sulfur atom or optionally protected imino; and R$^3$ has the same meaning as defined above, with a compound of the formula (XVII):

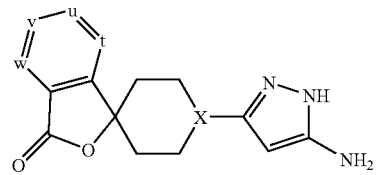

(XVII)

wherein t, v and w are each methine, said methine being optionally substituted by a substituent selected from the group consisting of halogen, lower alkyl, halo-lower alkyl, lower alkoxy, halo-lower alkoxy and optionally protected hydroxy, and u is nitrogen atom;

X has the same meaning as defined above or its salt to give a compound of the formula (XVIII):

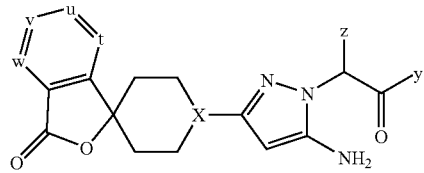

(XVIII)

wherein t, u, v, w, X, y and z have each the same meaning as defined above, followed by subjecting the compound of the formula (XVIII) to intramolecular dehydrative ring closure to give a compound of the formula (XIX):

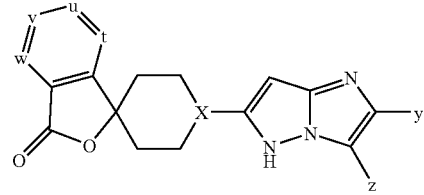

(XIX)

wherein t, u, v, w, X, y and z have each the same meaning as defined above, and optionally removing the protecting group(s) therefrom.

21. A neuropeptide Y receptor antagonist agent comprising a compound of the formula (I):

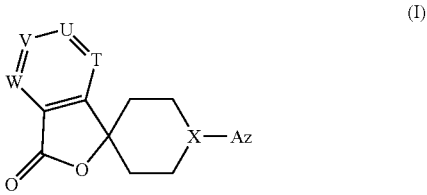

(I)

wherein Az is a group comprising a monocyclic azole or a bicyclic aromatic ring of the same or different fused azoles, which is optionally substituted by a substituent selected from the group consisting of halogen, cyano, lower alkyl, halo-lower alkyl, hydroxy, lower alkoxy, halo-lower alkoxy, lower alkoxycarbonyl, lower alkylsulfonyl, lower alkylsulfonyloxy, —N(R$^1$)R$^2$ and -Q$^1$-Ar$^1$;

Ar$^1$ is aryl or heteroaryl, any of which is optionally substituted by a substituent selected from the group consisting of halogen, nitro, oxo, hydroxy, lower alkyl, halo-lower alkyl, hydroxy-lower alkyl, cyclo-lower alkyl, lower alkenyl, lower alkoxy, halo-lower alkoxy, lower alkylthio, lower alkylsulfonyl, carboxyl, lower alkanoyl, lower alkoxycarbonyl, lower alkanoylamino and -Q$^2$-Ar$^2$;

Ar$^2$ is aryl or heteroaryl, any of which is optionally substituted by a substituent selected from the group consisting of halogen, cyano, lower alkyl, halo-lower alkyl, hydroxy-lower alkyl, hydroxy, lower alkoxy, halo-lower alkoxy, lower alkylamino, di-lower alkylamino, lower alkanoyl and aryl;

Q$^1$ and Q$^2$ are independently a single bond, oxygen atom, carbonyl or —N(R$^3$)—;

R$^1$ and R$^2$ are independently hydrogen atom or lower alkyl, or R$^1$ and R$^2$, taken together, form lower alkylene which may be interrupted by oxygen atom, sulfur atom or imino;

R$^3$ is hydrogen atom or lower alkyl;

T, V and W are methine, said methine being optionally substituted by a substituent selected from the group consisting of halogen, lower alkyl, halo-lower alkyl, hydroxy, lower alkoxy and halo-lower alkoxy; U is nitrogen atom; and X is nitrogen atom, or a salt or ester thereof as an active ingredient.

22. A Pharmaceutical composition for the treatment of bulimia, obesity or diabetes, comprising a compound of the formula (I):

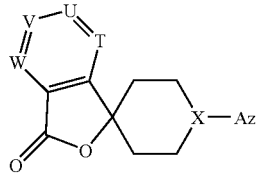

(I)

wherein Az is a group comprising a monocyclic azole or a bicyclic aromatic ring of the same or different fused azoles, which is optionally substituted by a substituent selected from the group consisting of halogen, cyano, lower alkyl, halo-lower alkyl, hydroxy, lower alkoxy, halo-lower alkoxy, lower alkoxycarbonyl, lower alkylsulfonyl, lower alkylsulfonyloxy, —N(R$^1$)R$^2$ and -Q$^1$-Ar$^1$;

Ar$^1$ is aryl or heteroaryl, any of which is optionally substituted by a substituent selected from the group consisting of halogen, nitro, oxo, hydroxy, lower alkyl, halo-lower alkyl, hydroxy-lower alkyl, cyclo-lower alkyl, lower alkenyl, lower alkoxy, halo-lower alkoxy, lower alkylthio, lower alkylsulfonyl, carboxyl, lower alkanoyl, lower alkoxycarbonyl, lower alkanoylamino and -Q$^2$-Ar$^2$;

Ar$^2$ is aryl or heteroaryl, any of which is optionally substituted by a substituent selected from the group consisting of halogen, cyano, lower alkyl, halo-lower alkyl, hydroxy-lower alkyl, hydroxy, lower alkoxy, halo-lower alkoxy, lower alkylamino, di-lower alkylamino, lower alkanoyl and aryl;

Q$^1$ and Q$^2$ are independently a single bond, oxygen atom, carbonyl or —N(R$^3$)—;

R$^1$ and R$^2$ are independently hydrogen atom or lower alkyl, or R$^1$ and R$^2$, taken together, form lower alkylene which may be interrupted by oxygen atom, sulfur atom or imino;

R$^3$ is hydrogen atom or lower alkyl;

T, V and W are methine, said methine being optionally substituted by a substituent selected from the group consisting of halogen, lower alkyl, halo-lower alkyl, hydroxy, lower alkoxy and halo-lower alkoxy; U is nitrogen atom; and X is nitrogen atom, or a salt or ester thereof as an active ingredient.

23. A pharmaceutical composition comprising the compound of claim 1 together with a pharmaceutically acceptable additive.

* * * * *